United States Patent [19]
Garner et al.

[11] Patent Number: 5,639,940
[45] Date of Patent: Jun. 17, 1997

[54] PRODUCTION OF FIBRINOGEN IN TRANSGENIC ANIMALS

[75] Inventors: Ian Garner; Michael L. Dalrymple, both of Edinburgh, Scotland; Donna E. Prunkard; Donald C. Foster, both of Seattle, Wash.

[73] Assignees: Pharmaceutical Proteins Ltd., Edinburgh, Scotland; ZymoGenetics, Inc., Seattle, Wash.

[21] Appl. No.: 206,176

[22] Filed: Mar. 3, 1994

[51] Int. Cl.$^6$ .............. C12N 5/10; C12N 15/06; C12N 15/09; C12P 21/02
[52] U.S. Cl. .............. 800/2; 435/69.1; 435/69.6; 435/69.7; 435/69.8; 435/71.1; 435/172.3; 514/44; 800/DIG. 1; 800/DIG. 4; 800/DIG. 6; 935/47; 935/48; 935/53; 935/55; 935/70
[58] Field of Search .............. 800/2; 435/172.1, 435/172.3, 69.1, 69.6, 69.7, 69.8, 71.1; 536/23.1, 23.4, 23.5, 24.1

[56] References Cited

U.S. PATENT DOCUMENTS

| | | |
|---|---|---|
| 4,873,316 | 10/1989 | Meade .............. 530/412 |
| 5,304,489 | 4/1994 | Rosen .............. 435/320.1 |

FOREIGN PATENT DOCUMENTS

| | | |
|---|---|---|
| 88-00239 | 1/1988 | WIPO . |
| 90-05188 | 5/1990 | WIPO . |
| 91/08216 | 6/1991 | WIPO . |
| 92/11358 | 7/1992 | WIPO . |
| 92-11757 | 7/1992 | WIPO . |

OTHER PUBLICATIONS

Grosschedi et al., *Cell* 38: 647–658, 1984.
Hartwig et al., *J. Biol. Chem.* 266: 6578–6585, 1991.
Roy et al., *J. Biol. Chem.* 266: 4758–4763, 1991.
Lord et al., *Blood* 73: 166–171, 1989.
Bolyard et al., *Blood* 73: 1202–1206, 1989.
Danishefsky et al., *Biochim. Biophys. Acta* 1048: 202–208, 19990.
Bolyard et al., *Gene* 66: 183–192, 1988.
Rixon et al., *Biochemistry* 24: 2077–2086, 1985.
Farrell et al., *Biochemistry* 30: 9414–9420, 1991.
Lord, *DNA* 4: 33–38, 1985.
Whitelaw et al., *Biochem. J.* 286: 31–39, 1992.
Farrell et al. *J., Biol. Chem.* 269: 226–231, 1994.
Palmiter et al., *Cell* 41: 343–345, 1985.
Chung et al., *Adv. Exp. Med. Biol.* 281: 39–48, 1990.
Chung et al., *Biochemistry* 22:3244–3250, 1983.
Lee et al., *Journal of Controlled Release* 29: 213–221, 1994.
*Chemical Abstracts* 115: Abstract No. 202768k: 526, 1991.
Wall, 1996, Themogenology 45:57–68.
Houdebine, 1994, Journal of Biotechnology 34:269–287.
*Genes*, Lewin, ed., John Wiley and Sons, N.Y. pp. 87–96.
D.F. Hosher, "Disorders of Blood Coagulation" in *Cecil Textbook of Medicine*, 18$^{th}$ Ed., Wyngaarden et al., eds., W.B. Saunders Co., Philadelphia, 1988. pp. 1060–1065.
Pursel et al., Science 244: 1281–1288.
Hennighausen, 1990. Protein Expression and Purification 1:3–8.

Primary Examiner—Brian R. Stanton
Attorney, Agent, or Firm—Gary E. Parker; Debra K. Leith; Deborah A. Sawislak

[57] ABSTRACT

Materials and methods for producing fibrinogen in transgenic non-human mammals are disclosed. DNA segments encoding Aα, Bβ and γ chains of fibrinogen are introduced into the germ line of a non-human mammal, and the mammal or its female progeny produces milk containing fibrinogen expressed from the introduced DNA segments. Non-human mammalian embryos and transgenic non-human mammals carrying DNA segments encoding heterologous fibrinogen polypeptide chains are also disclosed.

33 Claims, 5 Drawing Sheets

1

PRODUCTION OF FIBRINOGEN IN TRANSGENIC ANIMALS

BACKGROUND OF THE INVENTION

The final step in the blood coagulation cascade is the thrombin-catalyzed conversion of the soluble plasma protein fibrinogen to insoluble fibrin. Thrombin cleaves a small peptide (fibrinopeptide A) from one of the three component chains (the Aα-chain) of fibrinogen. Fibrin monomers subsequently polymerize and are cross-linked by activated factor XIII to form a stable clot.

Fibrinogen is a key component of biological tissue glues (see, e.g., U.S. Pat. Nos. 4,377,572 and 4,442,655), which mimic the formation of natural blood clots to promote hemostasis and repair damaged tissue. Tissue glues provide an adjunct or alternative to sutures, staples and other mechanical means for wound closure. However, the principal ingredients of these products (fibrinogen, factor XIII and thrombin) are prepared from pooled human plasma by cryoprecipitation (e.g. U.S. Pat. Nos. 4,377,572; 4,362,567; 4,909,251) or ethanol precipitation (e.g. U.S. Pat. No. 4,442,655) or from single donor plasma (e.g. U.S. Pat. No. 4,627,879; Spotnitz et al., *Am. Surg.* 55: 166–168, 1989). The resultant fibrinogen/factor XIII preparation is mixed with bovine thrombin immediately before use to convert the fibrinogen to fibrin and activate the factor XIII, thus initiating coagulation of the adhesive.

Commercially available adhesives are of pooled plasma origin. Because blood-derived products have been associated with the transmission of human immunodeficiency virus (HIV), hepatitis virus and other etiologic agents, the acceptance and availability of such adhesives is limited. At present they are not approved for use in the United States.

While the use of autologous plasma reduces the risk of disease transmission, autologous adhesives can only be used in elective surgery when the patient is able to donate the necessary blood in advance.

As noted above, fibrinogen consists of three polypeptide chains, each of which is present in two copies in the assembled molecule. These chains, designated the Aα, Bβ and γ-chains, are coordinately expressed, assembled and secreted by the liver. While it might be expected that recombinant DNA technology could provide an alternative to the isolation of fibrinogen from plasma, this goal has proven to be elusive. The three fibrinogen chains have been individually expressed in *E. coli* (Lord, DNA 4: 33–38, 1985; Bolyard and Lord, *Gene* 66: 183–192, 1988; Bolyard and Lord, *Blood* 73: 1202–1206), but functional fibrinogen has not been produced in a prokaryotic system. Expression of biologically competent fibrinogen in yeast has not been reported. Cultured transfected mammalian cells have been used to express biologically active fibrinogen (Farrell et al., *Blood* 74: 55a, 1989; Hartwig and Danishefsky, *J. Biol. Chem.* 266: 6578–6585, 1991; Farrell et al., *Biochemistry* 30: 9414–9420, 1991), but expression levels have been so low that production of recombinant fibrinogen in commercial quantities is not feasible. Experimental evidence suggests that lower transcription rates in cultured cells as compared to liver may be a factor in the low expression rates achieved to date, but increasing the amount of fibrinogen chain mRNA in transfected BHK cells did not produce corresponding increases in fibrinogen protein secretion (Prunkard and Foster, XIV Congress of the International Society on Thrombosis and Haemostasis, 1993). These latter results suggest that proper assembly and processing of fibrinogen involves tissue-specific mechanisms not present in common laboratory cell lines.

There remains a need in the art for methods of producing large quantities of high quality fibrinogen for use in tissue adhesives and other applications. There is a further need for fibrinogen that is free of blood-borne pathogens. The present invention fulfills these needs and provides other, related advantages.

SUMMARY OF THE INVENTION

It is an object of the present invention to provide commercially useful quantities of recombinant fibrinogen, particularly recombinant human fibrinogen. It is a further object of the invention to provide materials and methods for expressing fibrinogen in the mammary tissue of transgenic animals, particularly livestock animals such as cattle, sheep, pigs and goats.

Within one aspect, the present invention provides a method for producing fibrinogen comprising (a) providing a first DNA segment encoding a secretion signal operably linked to a fibrinogen Aα chain, a second DNA segment encoding a secretion signal operably linked to a fibrinogen Bβ chain, and a third DNA segment encoding a secretion signal operably linked to a fibrinogen γ chain, wherein each of the first, second and third segments is operably linked to additional DNA segments required for its expression in the mammary gland of a host female mammal; (b) introducing the DNA segments into a fertilized egg of a non-human mammalian species; (c) inserting the egg into an oviduct or uterus of a female of the species to obtain offspring carrying the DNA constructs; (d) breeding the offspring to produce female progeny that express the first, second and third DNA segments and produce milk containing biocompetent fibrinogen encoded by the segments; (e) collecting milk from the female progeny; and (f) recovering the fibrinogen from the milk. Within one embodiment, the egg containing the introduced segments is cultured for a period of time prior to insertion.

Within another aspect, the invention provides a method of producing fibrinogen comprising the steps of (a) incorporating a first DNA segment encoding a secretion signal operably linked to an Aα chain of fibrinogen into a β-lactoglobulin gene to produce a first gene fusion; (b) incorporating a second DNA segment encoding a secretion signal operably linked to a Bβ chain of fibrinogen into a β-lactoglobulin gene to produce a second gene fusion; (c) incorporating a third DNA segment encoding a secretion signal operably linked to a γ chain of fibrinogen into a β-lactoglobulin gene to produce a third gene fusion; (d) introducing the first, second and third gene fusions into the germ line of a non-human mammal so that the DNA segments are expressed in a mammary gland of the mammal or its female progeny and biocompetent fibrinogen is secreted into milk of the mammal or its female progeny; (e) obtaining milk from the mammal or its female progeny; and (f) recovering the fibrinogen from the milk. Within preferred embodiments, the mammal is a sheep, pig, goat or bovine.

Within another aspect, the invention provides a method for producing fibrinogen comprising the steps of (a) providing a transgenic female non-human mammal carrying in its germline heterologous DNA segments encoding Aα, Bβ and γ chains of fibrinogen, wherein the DNA segments are expressed in a mammary gland of the mammal and fibrinogen encoded by the DNA segments is secreted into milk of the mammal; (b) collecting milk from the mammal; and (c) recovering the fibrinogen from the milk.

Within another aspect, the invention provides a non-human mammalian embryo containing in its nucleus heterologous DNA segments encoding Aα, Bβ and γ chains of fibrinogen. Within a related aspect, the invention provides a transgenic non-human female mammal that produces recoverable amounts of human fibrinogen in its milk.

Within another aspect, the invention provides a method for producing a transgenic offspring of a mammal comprising the steps of (a) providing a first DNA segment encoding a fibrinogen Aα chain, a second DNA segment encoding a fibrinogen Bβ chain, and a third DNA segment encoding a fibrinogen γ chain, wherein each of said first, second and third segments is operably linked to additional DNA segments required for its expression in a mammary gland of a host female mammal and secretion into milk of the host female mammal; (b) introducing the DNA segments into a fertilized egg of a mammal of a non-human species; (c) inserting the egg into an oviduct or uterus of a female of the non-human species to obtain an offspring carrying the first, second and third DNA segments. In a related aspect, the invention provides non-human mammals produced according to this process.

Within an additional aspect, the invention provides a non-human mammal carrying its germline DNA segments encoding heterologous Aα, Bβ and γ chains of fibrinogen, wherein female progeny of the mammal express the DNA segments in a mammary gland to produce biocompetent fibrinogen.

These and other aspects of the invention will become evident to the skilled practitioner upon reference to the following detailed description and the attached drawings.

DETAILED DESCRIPTION OF THE INVENTION

Figure 1:
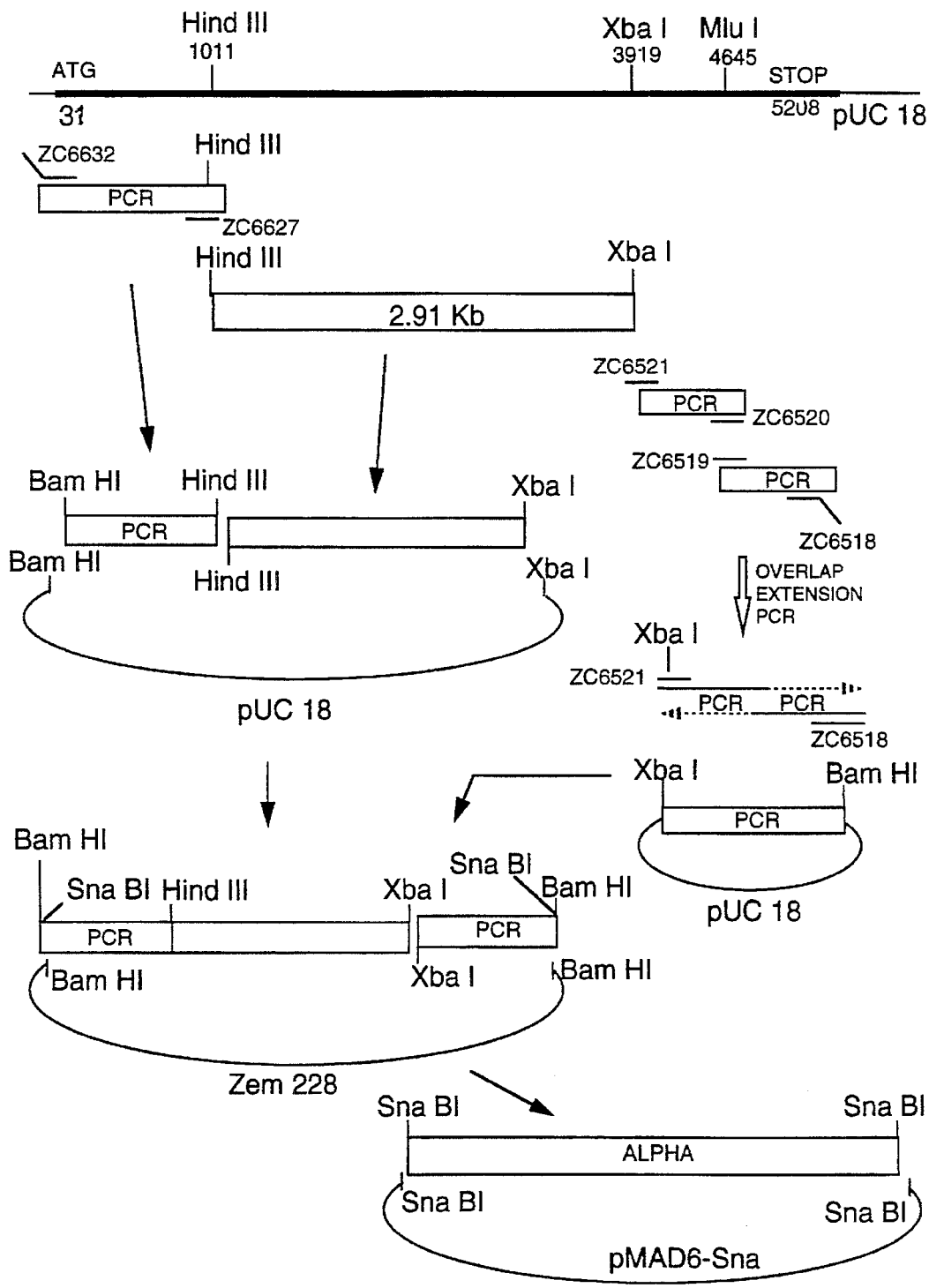
FIG. 1 illustrates the subcloning of a human fibrinogen Aα chain DNA sequence.

Prior to setting forth the invention in detail, it will be helpful to define certain terms used herein:

As used herein, the term "biocompetent fibrinogen" is used to denote fibrinogen that polymerizes when treated with thrombin to form insoluble fibrin.

The term "egg" is used to denote an unfertilized ovum, a fertilized ovum prior to fusion of the pronuclei or an early stage embryo (fertilized ovum with fused pronuclei).

A "female mammal that produces milk containing biocompetent fibrinogen" is one that, following pregnancy and delivery, produces, during the lactation period, milk containing recoverable amounts of biocompetent fibrinogen. Those skilled in the art will recognized that such animals will produce milk, and therefore the fibrinogen, discontinuously.

The term "progeny" is used in its usual sense to include children and descendants.

The term "heterologous" is used to denote genetic material originating from a different species than that into which it has been introduced, or a protein produced from such genetic material.

Within the present invention, transgenic animal technology is employed to produce fibrinogen within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (from about 1 to 15 g/l).

From a commercial point of view, it is clearly preferable to use as the host a species that has a large milk yield. While smaller animals such as mice and rats can be used (and are preferred at the proof-of-concept stage), within the present invention it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

Fibrinogen produced according to the present invention may be human fibrinogen or fibrinogen of a non-human animal. For medical uses, it is preferred to employ proteins native to the patient. The present invention thus provides fibrinogen for use in both human and veterinary medicine. Cloned DNA molecules encoding the component chains of human fibrinogen are disclosed by Rixon et al. (*Biochem.* 22: 3237, 1983), Chung et al. (*Biochem.* 22: 3244, 1983), Chung et al. (Biochem. 22: 3250, 1983), Chung et al. (*Adv. Exp. Med. Biol.* 281: 39–48, 1990) and Chung et al. (*Ann. NY Acad. Sci.* 408: 449–456, 1983). Bovine fibrinogen clones are disclosed by Brown et al. (*Nuc. Acids Res.* 17: 6397, 1989) and Chung et al. (*Proc. Natl. Acad. Sci. USA* 78: 1466–1470, 1981). Other mammalian fibrinogen clones are disclosed by Murakawa et al. (*Thromb. Haemost.* 69: 351–360, 1993). Representative sequences of human Aα, Bβ and γ chain genes are shown in SEQ ID NOS: 1, 3 and 5, respectively. Those skilled in the art will recognize that allelic variants of these sequences will exist; that additional variants can be generated by amino acid substitution, deletion, or insertion; and that such variants are useful within the present invention. In general, it is preferred that any engineered variants comprise only a limited number of amino acid substitutions, deletions, or insertions, and that any substitutions are conservative. Thus, it is preferred to produce fibrinogen chain polypeptides that are at least 90%, preferably at least 95, and more preferably 99% or more identical in sequence to the corresponding native chains. The term "γ chain" is meant to include the alternatively spliced γ' chain of fibrinogen (Chung et al., *Biochem.* 23: 4232–4236, 1984). A human γ' chain amino acid sequence is shown in SEQ ID NO: 6. The shorter γ chain is produced by alternative splicing at nucleotides 9511 and 10054 of SEQ ID NO: 5, resulting in translation terminating after nucleotide 10065 of SEQ ID NO: 5.

To obtain expression in the mammary gland, a transcription promoter from a milk protein gene is used. Milk protein genes include those genes encoding caseins, beta-lactoglobulin (BLG), α-lactalbumin, and whey acidic protein. The beta-lactoglobulin promoter is preferred. In the case of the ovine beta-lactoglobulin gene, a region of at least the proximal 406 bp of 5' flanking sequence of the ovine BLG gene (contained within nucleotides 3844 to 4257 of SEQ ID NO:7) will generally be used. Larger portions of the 5' flanking sequence, up to about 5 kbp, are preferred. A larger DNA segment encompassing the 5' flanking promoter region and the region encoding the 5' non-coding portion of the beta-lactoglobulin gene (contained within nucleotides 1 to 4257 of SEQ ID NO:7) is particularly preferred. See Whitelaw et al., Biochem J. 28: 31–39, 1992. Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836–840, 1988; Palmiter et al., Proc. Natl. Acad. Sci. USA 88: 478–482, 1991; Whitelaw et al., Transgenic Res. 1: 3–13, 1991; WO 89/01343; WO 91/02318). In this regard, it is generally preferred, where possible, to use genomic sequences containing all or some of the native introns of a gene encoding the protein or polypeptide of interest. Within certain embodiments of the invention, the further inclusion of at least some introns from the beta-lactoglobulin gene is preferred. One such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of one or more of the fibrinogen sequences is replaced with corresponding sequences from a milk specific protein gene. Such replacement provides a putative tissue-specific initiation environment to enhance expression. It is convenient to replace the entire fibrinogen chain pre-pro and 5' non-coding sequences with those of, for example, the BLG gene, although smaller regions may be replaced.

For expression of fibrinogen, DNA segments encoding each of the three component polypeptide chains of fibrinogen are operably linked to additional DNA segments required for their expression to produce expression units. Such additional segments include the above-mentioned milk protein gene promoter, as well as sequences which provide for termination of transcription and polyadenylation of mRNA. The expression units will further include a DNA segment encoding a secretion signal operably linked to the segment encoding the fibrinogen polypeptide chain. The secretion signal may be a native fibrinogen secretion signal or may be that of another protein, such as a milk protein. The term "secretion signal" is used herein to denote that portion of a protein that directs it through the secretory pathway of a cell to the outside. Secretion signals are most commonly found at the amino-termini of proteins. See, for example, von Heinje, Nuc. Acids Res. 14: 4683–4690, 1986; and Meade et al., U.S. Pat. No. 4,873,316, which are incorporated herein by reference.

Construction of expression units is conveniently carried out by inserting a fibrinogen chain sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a fibrinogen chain (including a secretion signal), thereby creating a gene fusion that includes the expression control sequences of the milk protein gene. In any event, cloning of the expression units in plasmids or other vectors facilitates the amplification of the fibrinogen sequences. Amplification is conveniently carried out in bacterial (e.g. E. coli) host cells, thus the vectors will typically include an origin of replication and a selectable marker functional in bacterial host cells.

In view of the size of the fibrinogen chain genes it is most practical to prepare three separate expression units, mix them, and introduce the mixture into the host. However, those skilled in the art will recognize that other protocols may be followed. For example, expression units for the three chains can be introduced individually into different embryos to be combined later by breeding. In a third approach, the three expression units can be linked in a single suitable vector, such as a yeast artificial chromosome or phage P1 clone. Coding sequences for two or three chains can be combined in polycistronic expression units (see, e.g., Levinson et al., U.S. Pat. No. 4,713,339).

The expression unit(s) is(are) then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, Science 240: 1468–1474, 1988) or site-directed integration using embryonic stem (ES) cells (reviewed by Bradley et al., Bio/Technology 10: 534–539, 1992). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art. See, for example, Hogan et al., Manipulating the Mouse Embryo: A Laboratory Manual, Cold Spring Harbor Laboratory, 1986; Simons et al., Bio/Technology 6: 179–183, 1988; Wall et al., Biol. Reprod. 32: 645–651, 1985; Buhler et al., Bio/Technology : 140–143, 1990; Ebert et al., Bio/Technology : 835–838, 1991; Krimpenfort et al., Bio/Technology 9: 844–847, 1991; Wall et al., J. Cell. Biochem. 49: 113–120, 1992; and WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., Proc. Natl. Acad. Sci. USA 77: 7380–7384, 1980; Gordon and Ruddle, Science 214: 1244–1246, 1981; Palmiter and Brinster, Cell 41: 343–345, 1985; Brinster et al., Proc. Natl. Acad. Sci. USA 82: 4438–4442, 1985; and Hogan et al. (ibid.). These techniques were subsequently adapted for use with larger animals, including livestock species (see e.g., WIPO publications WO 88/00239, WO 90/05188, and WO 92/11757; and Simons et al., Bio/Technology 6: 179–183, 1988). To summarize, in the most efficient route used to date in the generation of transgenic mice or livestock, several hundred linear molecules of the DNA of interest are injected into one of the pro-nuclei of a fertilized egg. Injection of DNA into the cytoplasm of a zygote can also be employed.

It is preferred to obtain a balanced expression of each fibrinogen chain to allow for efficient formation of the mature protein. Ideally, the three expression units should be on the same DNA molecule for introduction into eggs. This approach, however, may generate technical problems at, for example, the injection and manipulation stages. For example, the size of fibrinogen expression units may necessitate the use of yeast artificial chromosomes (YACs) or phage P1 to amplify and manipulate the DNA prior to injection. If this approach is followed, segments of DNA to be injected, containing all three expression units, would be very large, thus requiring modification of the injection procedure using, for example, larger bore needles. In a more simple approach, a mixture of each individual expression unit is used. It is preferred to combine equimolar amounts of the three expression units, although those skilled in the art will recognize that this ratio may be varied to compensate for the characteristics of a given expression unit. Some expression, generally a reduced level, will be obtained when lesser molar amounts of one or two chains are used, and expression efficiencies can generally be expected to decline in approximate proportion to the divergence from the preferred equimolar ratio. In any event, it is preferred to use a mixture having a ratio of $A\alpha:B\beta:\gamma$ expression units in the range of 0.5–1:0.5–1:0.5–1. When the ratio is varied from equimolar, it is preferred to employ relatively more of the $B\beta$ expression unit. Alternatively, one or a mixture of two of the expression units is introduced into individual eggs. However, animals derived by this approach will express only one or two fibrinogen chains. To generate an intact fibrinogen molecule by this approach requires a subsequent breeding program designed to combine all three expression units in individuals of a group of animals.

In general, female animals are superovulated by treatment with follicle stimulating hormone, then mated. Fertilized eggs are collected, and the heterologous DNA is injected into the eggs using known methods. See, for example, U.S. Pat. No. 4,873,191; Gordon et al., *Proc. Natl. Acad. Sci. USA* 77: 7380–7384, 1980; Gordon and Ruddle, *Science* 214: 1244–1246, 1981; Palmiter and Brinster, *Cell.* 41: 343–345, 1985; Brinster et al., *Proc. Natl. Acad. Sci. USA* 82: 4438–4442, 1985; Hogan et al., *Manipulating the Mouse Embryo: A Laboratory Manual*, Cold Spring Harbor Laboratory, 1986; Simons et al. *Bio/Technology* 6: 179–183, 1988; Wall et al., *Biol. Reprod.* 32: 645–651, 1985; Buhler et al., *Bio/Technology* 8: 140–143, 1990; Ebert et al., *Bio/Technology* 9: 835–838, 1991; Krimpenfort et al., *Bio/Technology* 9: 844–847, 1991; Wall et al., *J. Cell. Biochem.* 49: 113–120, 1992; WIPO publications WO 88/00239, WO 90/05118, and WO 92/11757; and GB 87/00458, which are incorporated herein by reference.

For injection into fertilized eggs, the expression units are removed from their respective vectors by digestion with appropriate restriction enzymes. For convenience, it is preferred to design the vectors so that the expression units are removed by cleavage with enzymes that do not cut either within the expression units or elsewhere in the vectors. The expression units are recovered by conventional methods, such as electro-elution followed by phenol extraction and ethanol precipitation, sucrose density gradient centrifugation, or combinations of these approaches.

DNA is injected into eggs essentially as described in Hogan et al., ibid. In a typical injection, eggs in a dish of an embryo culture medium are located using a stereo zoom microscope (×50 or ×63 magnification preferred). Suitable media include Hepes (N-2-hydroxyethylpiperazine-N'-2-ethanesulphonic acid) or bicarbonate buffered media such as M2 or M16 (available from Sigma Chemical Co., St. Louis, USA) or synthetic oviduct medium (disclosed below). The eggs are secured and transferred to the center of a glass slide on an injection rig using, for example, a drummond pipette complete with capillary tube. Viewing at lower (e.g. ×4) magnification is used at this stage. Using the holding pipette of the injection rig, the eggs are positioned centrally on the slide. Individual eggs are sequentially secured to the holding pipette for injection. For each injection process, the holding pipette/egg is positioned in the center of the viewing field. The injection needle is then positioned directly below the egg. Preferably using ×40 Nomarski objectives, both manipulator heights are adjusted to focus both the egg and the needle. The pronuclei are located by rotating the egg and adjusting the holding pipette assembly as necessary. Once the pronucleus has been located, the height of the manipulator is altered to focus the pronuclear membrane. The injection needle is positioned below the egg such that the needle tip is in a position below the center of the pronucleus. The position of the needle is then altered using the injection manipulator assembly to bring the needle and the pronucleus into the same focal plane. The needle is moved, via the joy stick on the injection manipulator assembly, to a position to the right of the egg. With a short, continuous jabbing movement, the pronuclear membrane is pierced to leave the needle tip inside the pronucleus. Pressure is applied to the injection needle via the glass syringe until the pronucleus swells to approximately twice its volume. At this point, the needle is slowly removed. Reverting to lower (e.g. ×4) magnification, the injected egg is moved to a different area of the slide, and the process is repeated with another egg.

After the DNA is injected, the eggs may be cultured to allow the pronuclei to fuse, producing one-cell or later stage embryos. In general, the eggs are cultured at approximately the body temperature of the species used in a buffered medium containing balanced salts and serum. Surviving embryos are then transferred to pseudopregnant recipient females, typically by inserting them into the oviduct or uterus, and allowed to develop to term. During embryogenesis, the injected DNA integrates in a random fashion in the genomes of a small number of the developing embryos.

Potential transgenic offspring are screened via blood samples and/or tissue biopsies. DNA is prepared from these samples and examined for the presence of the injected construct by techniques such as polymerase chain reaction (PCR; see Mullis, U.S. Pat. No. 4,683,202) and Southern blotting (Southern, *J. Mol. Biol.* 98:503, 1975; Maniatis et al., *Molecular Cloning: A Laboratory Manual*, Cold Spring Harbor Laboratory, 1982). Founder transgenic animals, or G0s, may be wholly transgenic, having transgenes in all of their cells, or mosaic, having transgenes in only a subset of cells (see, for example, Wilkie et al., *Develop. Biol.* 118: 9–18, 1986). In the latter case, groups of germ cells may be wholly or partially transgenic. In the latter case, the number of transgenic progeny from a founder animal will be less than the expected 50% predicted from Mendelian principles. Founder G0 animals are grown to sexual maturity and mated to obtain offspring, or G1s. The G1s are also examined for the presence of the transgene to demonstrate transmission from founder G0 animals. In the case of male G0s, these may be mated with several non-transgenic females to generate many offspring. This increases the chances of observing transgene transmission. Female G0 founders may be mated naturally, artificially inseminated or superovulated to obtain many eggs which are transferred to surrogate mothers. The latter course gives the best chance of observing transmission in animals having a limited number of young. The above-described breeding procedures are used to obtain animals that can pass the DNA on to subsequent generations of offspring in the normal, Mendelian fashion, allowing the development of, for example, colonies (mice), flocks (sheep), or herds (pigs, goats and cattle) of transgenic animals.

The milk from lactating G0 and G1 females is examined for the expression of the heterologous protein using immunological techniques such as ELISA (see Harlow and Lane, *Antibodies, A Laboratory Manual*, Cold Spring Harbor Laboratory, 1988) and Western blotting (Towbin et al., *Proc. Natl. Acad. Sci. USA* 76: 4350–4354, 1979). For a variety of reasons known in the art, expression levels of the heterologous protein will be expected to differ between individuals.

A satisfactory family of animals should satisfy three criteria: they should be derived from the same founder G0 animal; they should exhibit stable transmission of the transgene; and they should exhibit stable expression levels from generation to generation and from lactation to lactation of individual animals. These principles have been demonstrated and discussed (Carver et al., *Bio/Technology* 11: 1263–1270, 1993). Animals from such a suitable family are referred to as a "line." Initially, male animals, G0 or G1, are used to derive a flock or herd of producer animals by natural or artificial insemination. In this way, many female animals containing the same transgene integration event can be quickly generated from which a supply of milk can be obtained.

The fibrinogen is recovered from milk using standard practices such as skimming, precipitation, filtration and protein chromatography techniques.

Fibrinogen produced according to the present invention is useful within human and veterinary medicine, such as in the formulation of surgical adhesives. Adhesives of this type are known in the art. See, for example, U.S. Pat. Nos. 4,377,572; 4,442,655; 4,462,567; and 4,627,879, which are incorporated herein by reference. In general, fibrinogen and factor XIII are combined to form a first component that is mixed just prior to use with a second component containing thrombin. The thrombin converts the fibrinogen to fibrin, causing the mixture to gel, and activates the factor XIII. The activated factor XIII cross links the fibrin to strengthen and stabilize the adhesive matrix. Such adhesives typically contain from about 30 mg/ml to about 100 mg/ml fibrinogen and from about 50 µg/ml to about 500 µg/ml factor XIII. They may also contain additional ingredients, such as aprotinin, albumin, fibronectin, bulking agents, and solubilizers. Methods for producing factor XIII are known in the art. See, for example, U.S. Pat. No. 5,204,447. The fibrinogen is also useful for coating surfaces of polymeric articles, e.g. synthetic vascular grafts, as disclosed in U.S. Pat. No. 5,272,074 (incorporated herein by reference).

The invention is further illustrated by the following non-limiting examples.

EXAMPLES

Example I

The multiple cloning site of the vector pUC18 (Yanisch-Perron et al., *Gene* 33:103–119, 1985) was removed and replaced with a synthetic double stranded oligonucleotide (the strands of which are shown in SEQ ID NO: 8 and SEQ ID NO: 27) containing the restriction sites Pvu I/Mlu I/Eco RV/Xba I/Pvu I/Mlu I, and flanked by 5' overhangs compatible with the restriction sites Eco RI and Hind III. pUC18 was cleaved with both Eco RI and Hind III, the 5' terminal phosphate groups were removed with calf intestinal phosphatase, and the oligonucleotide was ligated into the vector backbone. The DNA sequence across the junction was confirmed by sequencing, and the new plasmid was called pUCPM.

The β-lactoglobulin (BLG) gene sequences from pSS1tgXS (disclosed in WIPO publication WO 88/00239) were excised as a Sal I-Xba I fragment and recloned into the vector pUCPM that had been cut with Sal I and Xba I to construct vector pUCXS. pUCXS is thus a pUC18 derivative containing the entire BLG gene from the Sal I site to the Xba I site of phage SS1 (Ali and Clark, *J. Mol. Biol.* 199: 415–426, 1988).

The plasmid pSS1tgSE (disclosed in WIPO publication WO 88/00239) contains a 1290 bp BLG fragment flanked by Sph I and EcoR I restriction sites, a region spanning a unique Not I site and a single Pvu II site which lies in the 5' untranslated leader of the BLG mRNA. Into this Pvu II site was ligated a double stranded, 8 bp DNA linker (5'-GGATATCC-3') encoding the recognition site for the enzyme Eco RV. This plasmid was called pSS1tgSE/RV. DNA sequences bounded by Sph I and Not I restriction sites in pSS1tgSE/RV were excised by enzymatic digestion and used to replace the equivalent fragment in pUCXS. The resulting plasmid was called pUCXSRV. The sequence of the BLG insert in pUCSXRV is shown in SEQ ID NO: 7, with the unique Eco RV site at nucleotide 4245 in the 5' untranslated leader region of the BLG gene. This site allows insertion of any additional DNA sequences under the control of the BLG promoter 3' to the transcription initiation site.

Using the primers BLGAMP3 (5'-TGG ATC CCC TGC CGG TGC CTC TGG-3'; SEQ ID NO: 9) and BLGAMP4 (5'-AAC GCG TCA TCC TCT GTG AGC CAG-3'; SEQ ID NO: 10) a PCR fragment of approximately 650 bp was produced from sequences immediately 3' to the stop codon of the BLG gene in pUCXSRV. The PCR fragment was engineered to have a BamH I site at its 5' end and an Mlu I site at its 3' end and was cloned as such into BamH I and Mlu I cut pGEM7zf(+) (Promega) to give pDAM200(+).

pUCXSRV was digested with Kpn I, and the largest, vector containing band was gel purified. This band contained the entire pUC plasmid sequences and some 3' non-coding sequences from the BLG gene. Into this backbone was ligated the small Kpn I fragment from pDAM200(+) which, in the correct orientation, effectively engineered a BamH I site at the extreme 5' end of the 2.6 Kbp of the BLG 3' flanking region. This plasmid was called pBLAC200. A 2.6 Kbp Cla I-Xba I fragment from pBLAC200 was ligated into Cla I-Xba I cut pSP72 vector (Promega), thus placing an EcoR V site immediately upstream of the BLG sequences. This plasmid was called pBLAC210.

The 2.6 Kbp Eco RV-Xba I fragment from pBLAC210 was ligated into Eco RV-Xba I cut pUCXSRV to form pMAD6. This, in effect, excised all coding and intron sequences from pUCXSRV, forming a BLG minigene consisting of 4.3 Kbp of 5' promoter and 2.6 Kbp of 3' downstream sequences flanking a unique EcoR V site. An oligonucleotide linker (ZC6839: ACTACGTAGT; SEQ ID NO: 11) was inserted into the Eco RV site of pMAD6. This modification destroyed the Eco RV site and created a Sna BI site to be used for cloning purposes. The vector was designated pMAD6-Sna. Messenger RNA initiates upstream of the Sna BI site and terminates downstream of the Sna BI site. The precursor transcript will encode a single BLG-derived intron, intron 6, which is entirely within the 3' untranslated region of the gene.

Example II

Clones encoding the individual fibrinogen chains were obtained from the laboratory of Dr. Earl W. Davie, University of Washington, Seattle. A genomic fibrinogen Aα-chain clone (Chung et al., 1990, ibid.) was obtained from the plasmid BS4. This plasmid contains the Aα clone inserted into the Sal I and Bam HI sites of the vector pUC18, but lacks the coding sequence for the first four amino acids of the Aα chain. A genomic Bβ-chain DNA (Chung et al., ibid.) was isolated from a lambda Charon 4A phage clone (designated βλ4) as two EcoRI fragments of ca. 5.6 Kbp each. The two fragments were cloned separately into pUC19 that had been digested with Eco RI and treated with calf intestinal phosphatase. The resulting clones were screened by digestion with the restriction enzyme Pvu II to distinguish plasmids with the 5' and 3' Bβ inserts (designated Beta5'RI/puc and Beta3'RI/puc, respectively). Genomic γ-chain clones were isolated as described by Rixon et al. (*Biochemistry* 24: 2077–2086, 1985). Clone pγ12A9 comprises 5' non-coding sequences and approximately 4535 bp of γ-chain coding sequence. Clone pγ12F3 comprises the remaining coding sequence and 3' non-coding nucleotides. Both are pBR322-based plasmids with the fibrinogen sequences inserted at the EcoRI site. These plasmids were used as templates for the respective PCR reactions.

The fibrinogen chain coding sequences were tailored for insertion into expression vectors using the polymerase chain reaction (PCR) as generally described by Mullis (U.S. Pat. No. 4,683,202). This procedure removed native 5' and 3' untranslated sequences, added a 9 base sequence (CCT GCA GCC) upstream of the first ATG of each coding sequence, supplied the first four codons for the Aα-chain sequence, removed an internal Mlu I site in the Aα sequence and added restriction sites to facilitate subsequent cloning steps.

Referring to FIG. 1, the 5' end of the Aα coding sequence was tailored in a PCR reaction containing 20 pmole for each of primers ZC6632 (SEQ ID NO: 12) and ZC6627 (SEQ ID NO: 13), approximately 10 ng of plasmid BS4 template DNA, 10 µl of a mix containing 2.5 mM each dNTP, 7.5 µl 10× *Pyrococcus furiosus* (Pfu) DNA polymerase buffer #1 (200 mM Tris-HCl, pH 8.2, 100 mM KCl, 60 mM $(NH_4)_2SO_4$, 20 mM $MgCl_2$, 1% Triton X-100, 100 µg/ml nuclease free bovine serum albumin)(Stratagene, La Jolla, Calif.), and water to 75 µl. The mixture was heated to 94° C. in a DNA thermal cycler (Perkin-Elmer Corp., Norwalk, Conn.). To the heated mixture was added 25 µl of a mixture containing 2.5 µl 10× Pfu buffer #1, 22 µl $H_2O$ and 1 µl 2.5 units/µl Pfu DNA polymerase (Stratagene). The reactions were run in a DNA thermal cycler (Perkin-Elmer) for five cycles of 94°, 45 seconds; 40°, 90 seconds; 72°, 120 seconds; 20 cycles of 94°, 45 seconds; 45°, 90 seconds; 72°, 120 seconds; then incubated at 72° for 7 minutes. The 5' PCR-generated fragment was digested with Bam HI and Hind III, and the Bam HI-Hind III fragment was then ligated to an internal 2.91 Kbp Hind III-Xba I fragment and Bam HI, Xba I-digested pUC18. PCR-generated exon sequences were sequenced.

Referring again to FIG. 1, the 3' end of the Aα coding sequence was tailored in a series of steps in which the Mlu I site 563 bases upstream from the stop codon of the Aα sequence was mutated using an overlap extension PCR reaction (Ho et al., *Gene* 77: 51–59, 1989). In the first reaction 40 pmole of each of primers ZC6521 (SEQ ID NO: 14) and ZC6520 (SEQ ID NO: 15) were combined with approximately 10 ng of plasmid BS4 template DNA in a reaction mixture as described above. The reaction was run for 5 cycles of 94°, 45 seconds; 40°, 60 seconds; 72°, 120 seconds; 15 cycles of 94°, 45 seconds; 45°, 60 seconds; 72°, 120 seconds; then incubated at 72° for 7 minutes. A second reaction was carried out in the same manner using 40 pmole of each of primers ZC6519 (SEQ ID NO: 16) and ZC6518 (SEQ ID NO: 17) and BS4 as template. The PCR-generated DNA fragments from the first and second reactions were isolated by gel electrophoresis and elution from the gel. Approximately 1/10 of each recovered reaction product was combined with 40 pmole of each of primers ZC6521 (SEQ ID NO: 14) and ZC6518 (SEQ ID NO: 17) in a PCR reaction in which the complementary 3' ends of each fragment (containing the single base change) annealed and served as a primer for the 3' extension of the complementary strand. PCR was carried out using the same reaction conditions as in the first and second 3' PCR steps. The reaction product was then digested with Xba I and Bam HI, and the Xba I-Bam HI fragment was cloned into Xba I, Bam HI-digested pUC18. PCR-generated exons were sequenced.

Figure 2:
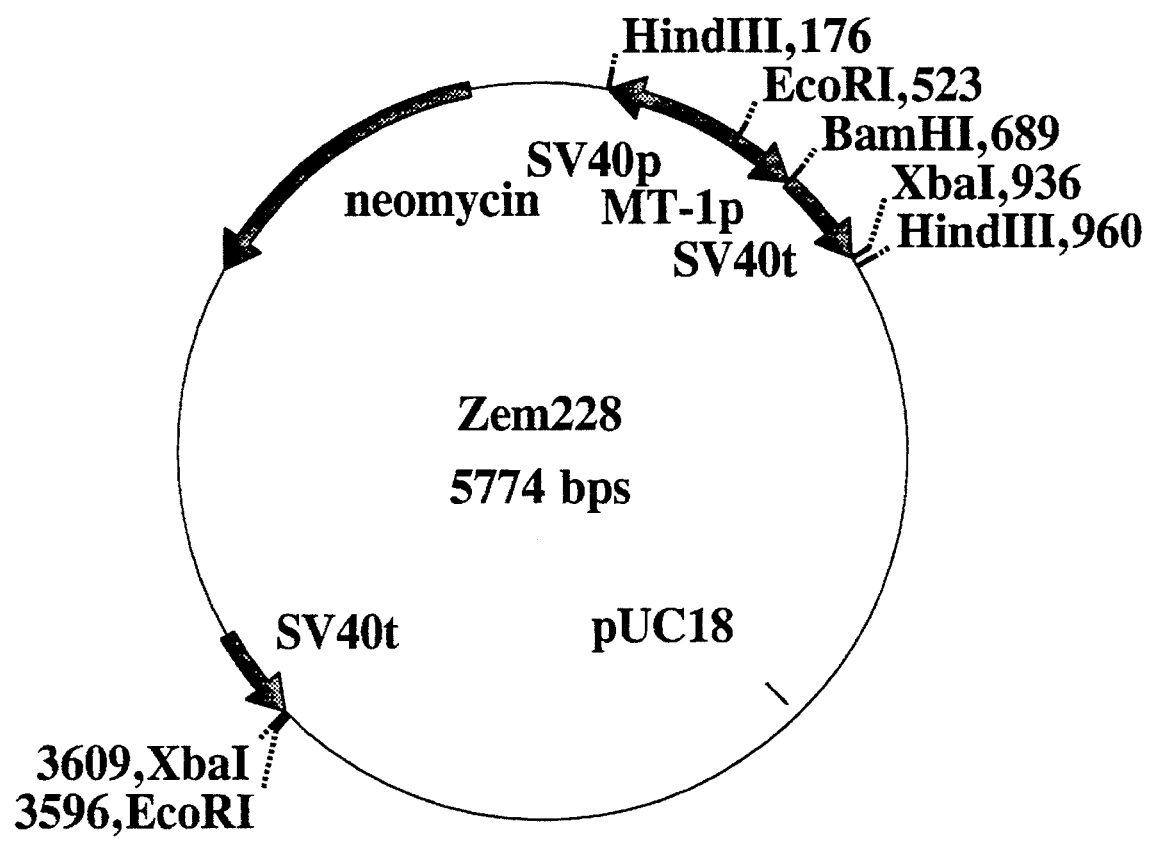
FIG. 2 is a partial restriction map of the vector Zem228. Symbols used are MT-1p, mouse metallothionein promoter; SV40t, SV40 terminator; and SV40p, SV40 promoter.

As shown in FIG. 1, the 5' Bam HI-Xba I fragment (3.9 Kbp) and the 3' Xba I-Bam HI fragment (1.3 Kbp) were inserted into the Bam HI site of the vector Zem228. Zem228 is a pUC18 derivative comprising a Bam HI cloning site between a mouse MT-1 promoter and SV40 terminator, and a neomycin resistance marker flanked by SV40 promoter and terminator sequences. See European Patent Office Publication EP 319,944 and FIG. 2. The entire Aα coding sequence was isolated from the Zem228 vector as an Sna BI fragment, which was inserted into the Sna BI site of the plasmid pMAD6-Sna.

Figure 3:
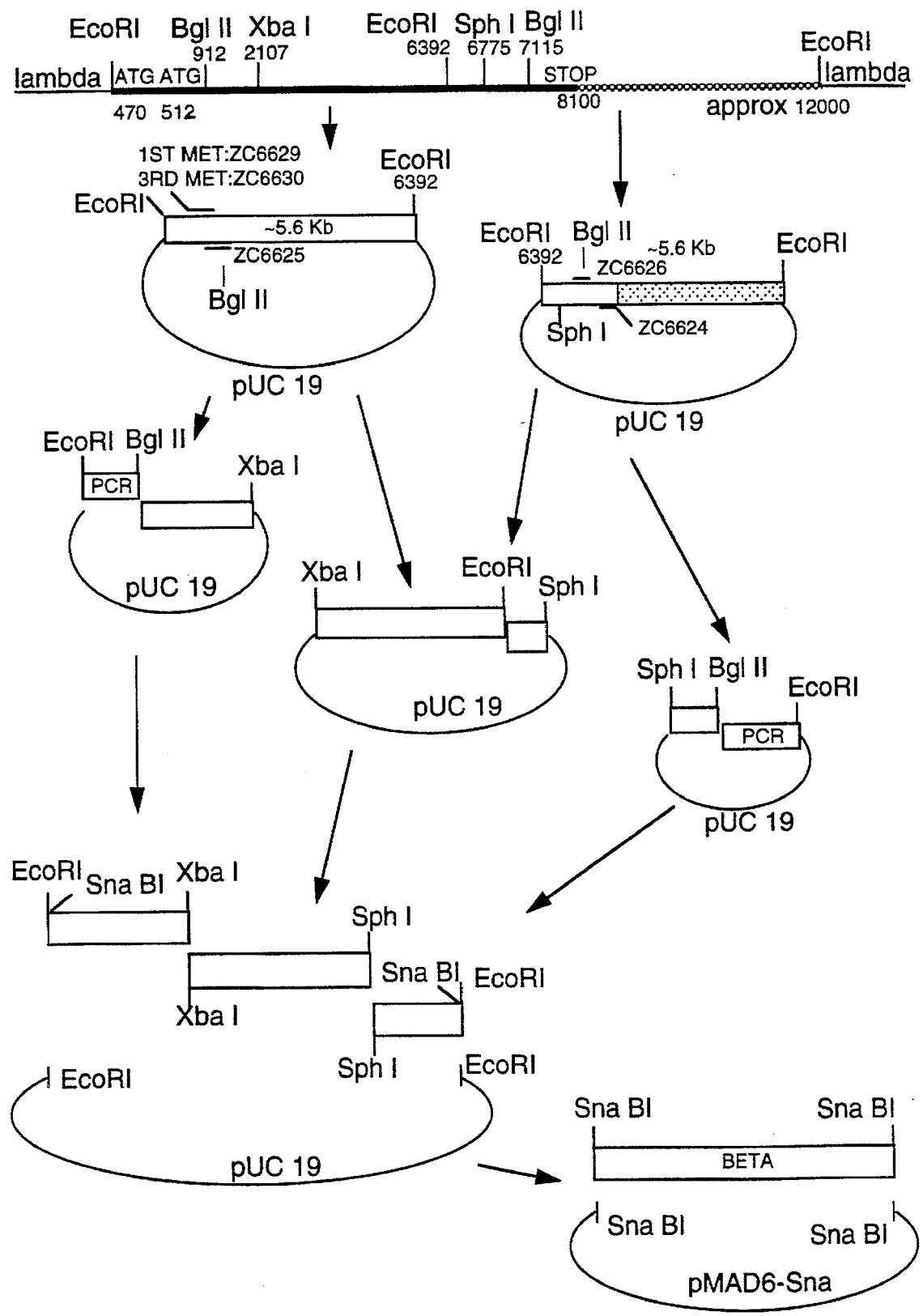
FIG. 3 illustrates the subcloning of a human fibrinogen Bβ chain DNA sequence.

Referring to FIG. 3, the 5' end of the Bβ-chain was tailored by PCR using the oligonucleotides ZC6629 (SEQ ID NO: 18), ZC6630 (SEQ ID NO: 19) and ZC6625 (SEQ ID NO: 20). These primers were used in pairwise combinations (ZC6629+ZC6625 or ZC6630+ZC6625) to generate Bβ coding sequences beginning at the first ATG codon (position 470 in SEQ ID NO: 3)(designated N1-Beta) or the third ATG codon (position 512 in SEQ ID NO: 3)(designated N3-Beta). Approximately 5 ng of Beta5'RI/puc template DNA was combined with 20 pmole of each of the primers (N1-Beta:ZC6629, SEQ ID NO: 18+ZC6625, SEQ ID NO: 20; or N3-Beta:ZC6630, SEQ ID NO: 19+ZC6625, SEQ ID NO: 20) in a reaction mixture as described above. The mixtures were incubated for 5 cycles of 94°, 45 seconds; 40°, 120 seconds; (N1-Beta) or 90 seconds (N3-Beta); 72°, 120 seconds; 20 cycles of 94°, 45 seconds; 45°, 120 seconds; (N1-Beta) or 90 seconds (N3-Beta); 72°, 120 seconds; then incubated at 72° for 7 minutes. The two reaction products N1, 555 bp or N3, 510 bp) were each digested with Eco RI and Bgl II, and the fragments were ligated to the internal Bgl II-Xba I fragment and Eco RI+Xba I-digested pUC19. The 3' end of the Bβ sequence was tailored in a reaction mixture as described above using the oligonucleotide primers ZC6626 (SEQ ID NO: 21) and ZC6624 (SEQ ID NO: 22) and approximately 5 ng of Beta3'RI/puc template. The mixtures were incubated for 5 cycles of 94°, 45 seconds; 40°, 90 seconds; 72°, 120 seconds; 15 cycles of 94°, 45 seconds; 45°, 90 seconds; 72°, 120 seconds; then incubated at 72° for 7 minutes. A 990 bp Bgl II-Eco RI fragment was isolated. This 3' fragment was ligated to the adjacent coding fragment (340 bp, SphI-Bgl II) and Sph I+Eco RI-digested pUC19. The 3' and 5' PCR-generated exons were sequenced. A third intermediate vector was constructed by combining two internal fragments (4285 bp Xba I-Eco RI and 383 kb Eco RI-Sph I) in Xba I+Sph I-digested pUC19. The entire Bβ coding sequence (two forms) was then assembled by ligating one of the 5' Eco RI-Xba I fragments, the internal Xba I-Sph I fragment, the 3' Sph I-Eco RI fragment and Eco RI-digested vector pUC19. The Bβ sequence was then isolated as a 7.6 Kbp Sna BI fragment and inserted into the Sna BI site of pMAD6-Sna.

Figure 4:
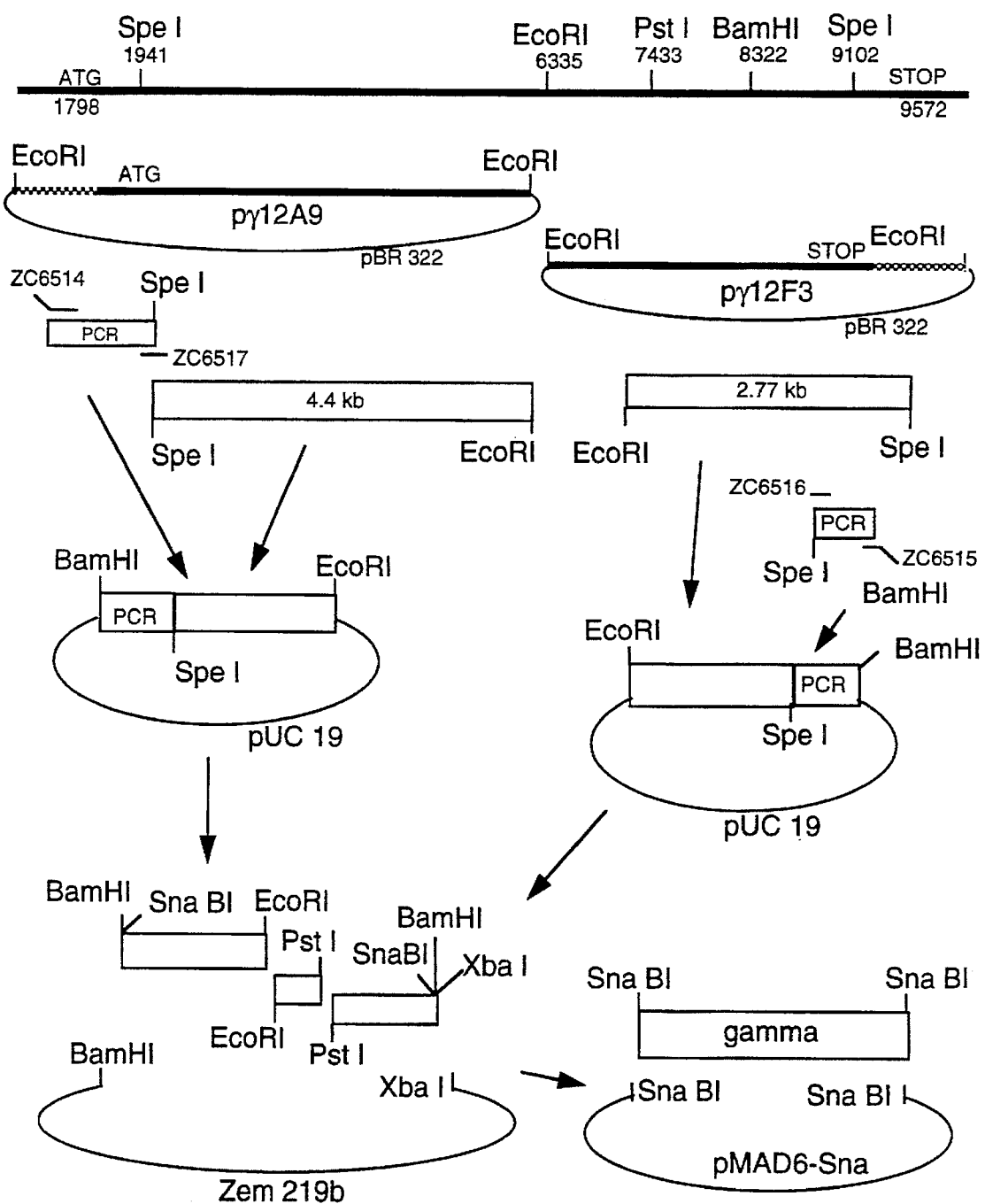
FIG. 4 illustrates the subcloning of a human fibrinogen γ chain DNA sequence.
Figure 5:
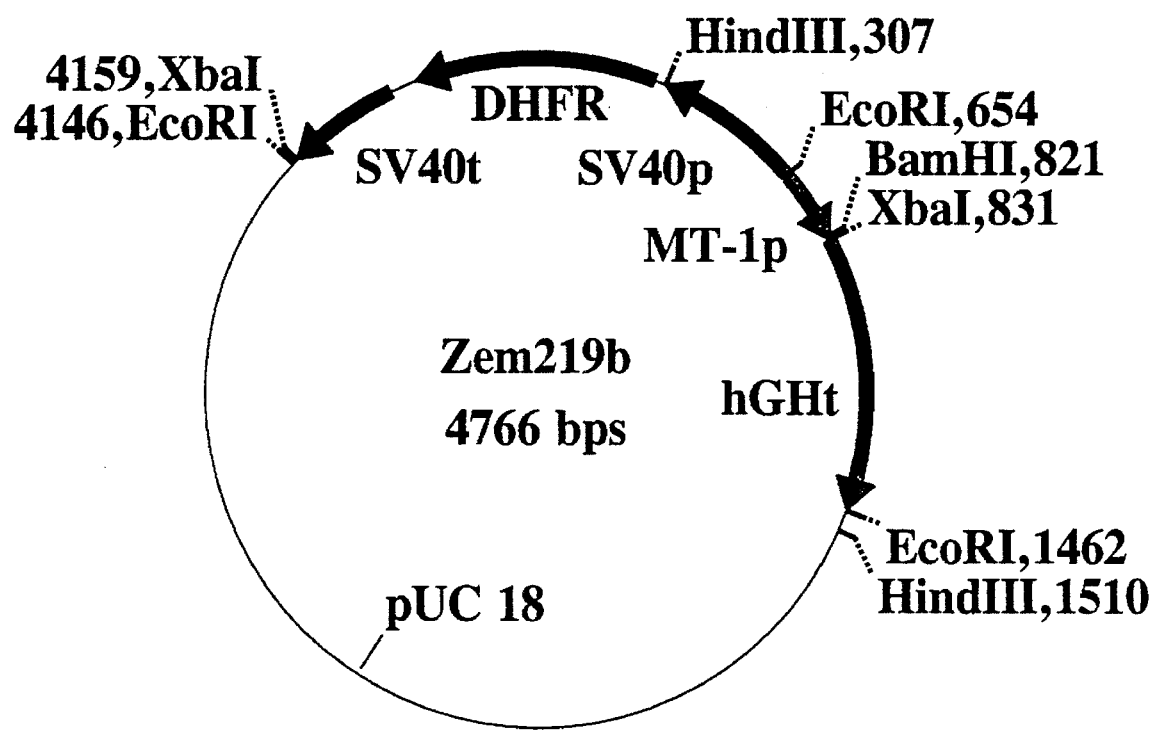
FIG. 5 is a partial restriction map of the vector Zem219b. Symbols used are MT-1p, mouse metallothionein promoter; hGHt, human growth hormone terminator; SV40p, SV40 promoter; DHFR, dihydrofolate reductase gene; and SV40t, SV40 terminator.

Referring to FIG. 4, the 5' end of the gamma chain sequence was tailored by PCR using the oligonucleotide primers ZC6514 (SEQ ID NO: 23) and ZC6517 (SEQ ID NO: 24) and approximately 50 ng of pγ12A9 as template. The PCR reaction was run as described above using 40 pM of each primer. The reaction was run for 5 cycles of 94°, 45 seconds; 40°, 60 seconds, 72°, 120 seconds, followed by 15 cycles of 94°, 45 seconds; 45°, 60 seconds; 72°, 120 seconds. The resulting 213 bp fragment was digested with Bam HI and Spe I, and the resulting restriction fragment was ligated with the adjacent downstream 4.4 kb Spe I-Eco RI fragment and Bam HI+Eco RI digested pUC19. The 3' end of the gamma chain sequence was tailored using oligonucleotide primers ZC6516 (SEQ ID NO: 25) and ZC6515 (SEQ ID NO: 26) using 40 pM of each primer, approximately 50 ng of pγ12F3 template and the same thermal cycling schedule as used for the 5' fragment. The resulting 500 bp fragment was digested with Spe I and Bam HI, and the resulting restriction fragment was ligated with the upstream 2.77 kb Eco RI-Spe I fragment and Eco RI+Bam HI-digested pUC19. All PCR-generated exons were sequenced. The entire γ'-chain coding sequence was then assembled by ligating a 4.5 Kbp Bam HI-Eco RI 5' fragment, a 1.1 Kbp Eco RI-Pst I internal fragment and a 2.14 Kbp Pst I-Xba I 3' fragment in Bam HI+Xba I-digested Zem219b. Zem219b is a pUC18-derived vector containing a mouse metallothionein promoter and a DHFR selectable marker operably linked to an SV40 promoter (FIG. 5). Plasmid Zem219b has been deposited with American Type Culture Collection as an *E. coli* XL1-blue transformant under Accession No. 68979. The entire γ'-chain coding sequence was then isolated as a 7.8 Kbp Sna B1 fragment and inserted into the Sna BI site of pMAD6-Sna.

Example III

Mice for initial breeding stocks (C57BL6J, CBACA) were obtained from Harlan Olac Ltd. (Bicester, UK). These were mated in pairs to produce F1 hybrid cross (B6CBAF1) for recipient female, superovulated females, stud males and vasectomized males. All animals were kept on a 14 hour light/10 hour dark cycle and fed water and food (Special Diet Services RM3, Edinburgh, Scotland) ad libitum.

Transgenic mice were generated essentially as described in Hogan et al., *Manipulating the Mouse Embryo: A Laboratory Manual*, Cold Spring Harbor Laboratory, 1986, which is incorporated herein by reference in its entirety. Female B6CBAF1 animals were superovulated at 4–5 weeks of age by an i.p. injection of pregnant mares' serum gonadotrophin (FOLLIGON, Vet-Drug, Falkirk, Scotland) (5 iu) followed by an i.p. injection of human chorionic gonadotrophin (CHORULON, Vet-Drug, Falkirk, Scotland) (5 iu) 45 hours later. They were then mated with a stud male overnight. Such females were next examined for copulation plugs. Those that had mated were sacrificed, and their eggs were collected for microinjection.

DNA was injected into the fertilized eggs as described in Hogan et al. (ibid.) Briefly, each of the vectors containing the Aα, Bβ and γ expression units was digested with Mlu I, and the expression units were isolated by sucrose gradient centrifugation. All chemicals used were reagent grade (Sigma Chemical Co., St. Louis, Mo., U.S.A.), and all solutions were sterile and nuclease-free. Solutions of 20% and 40% sucrose in 1M NaCl , 20 mM Tris pH 8.0, 5 mM EDTA were prepared using UHP water and filter sterilized. A 30% sucrose solution was prepared by mixing equal volumes of the 20% and 40% solutions. A gradient was prepared by layering 0.5 ml steps of the 40%, 30% and 20% sucrose solutions into a 2 ml polyallomer tube and allowed to stand for one hour. 100 µl of DNA solution (max. 8 µg DNA) was loaded onto the top of the gradient, and the gradient was centrifuged for 17–20 hours at 26,000 rpm, 15° C. in a Beckman TL100 ultracentrifuge using a TLS-55 rotor (Beckman Instruments, Fullerton, Calif., USA). Gradients were fractionated by puncturing the tube bottom with a 20 ga. needle and collecting drops in a 96 well microtiter plate. 3 µl aliquots were analyzed on a 1% agarose mini-gel. Fractions containing the desired DNA fragment were pooled and ethanol precipitated overnight at −20° C. in 0.3M sodium acetate. DNA pellets were resuspended in 50–100 µl UHP water and quantitated by fluorimetry. The expression units were diluted in Dulbecco's phosphate buffered saline without calcium and magnesium (containing, per liter, 0.2 g KCl, 0.2 g $KH_2PO_4$, 8.0 g NaCl, 1.15 g $Na_2HPO_4$), mixed (using either the N1-Beta or N3-Beta expression unit) in a 1:1:1 molar ratio, concentration adjusted to about 6 µg/ml, and injected into the eggs (~2 pl total DNA solution per egg).

Recipient females of 6–8 weeks of age are prepared by mating B6CBAF1 females in natural estrus with vasectomized males. Females possessing copulation plugs are then kept for transfer of microinjected eggs.

Following birth of potential transgenic animals, tail biopsies are taken, under anesthesia, at four weeks of age. Tissue samples are placed in 2 ml of tail buffer (0.3M Na acetate, 50 mM HCl, 1.5 mM $MgCl_2$, 10 mM Tris-HCl, pH 8.5, 0.5% NP40, 0.5% Tween 20) containing 200 µg/ml proteinase K (Boehringer Mannheim, Mannheim, Germany) and vortexed. The samples are shaken (250 rpm) at 55°–60° for 3 hours to overnight. DNA prepared from biopsy samples is examined for the presence of the injected constructs by PCR and Southern blotting. The digested tissue is vigorously vortexed, and 5 µl aliquots are placed in 0.5 ml microcentrifuge tubes. Positive and negative tail samples are included as controls. Forty µl of silicone oil (BDH, Poole, UK) is added to each tube, and the tubes are briefly centrifuged. The tubes are incubated in the heating block of a thermal cycler (e.g. Omni-gene, Hybaid, Teddington, UK) to 95° C. for 10 minutes. Following this, each tube has a 45 µl aliquot of PCR mix added such that the final composition of each reaction mix is: 50 mM KCl; 2 mM $MgCl_2$; 10 mM Tris-HCl (pH 8.3); 0.01% gelatin; 0.1% NP40, 10% DMSO; 500 nM each primer, 200 µM dNTPs; 0.02 U/µl Taq polymerase (Boehringer Mannheim, Mannheim, Germany). The tubes are then cycled through 30 repeated temperature changes as required by the particular primers used. The primers may be varied but in all cases must target the BLG promoter region. This is specific for the injected DNA fragments because the mouse does not have a BLG gene. Twelve µl of 5× loading buffer containing Orange G marker dye (0.25% Orange G [Sigma] 15% Ficoll type 400 [Pharmacia Biosystems Ltd., Milton Keynes, UK]) is then added to each tube, and the reaction mixtures are electrophoresed on a 1.6% agarose gel containing ethidium bromide (Sigma) until the marker dye has migrated ⅔ of the length of the gel. The gel is visualized with a UV light source emitting a wavelength of 254 nm. Transgenic mice having one or more of the injected DNA fragments are identified by this approach.

Positive tail samples are processed to obtain pure DNA. The DNA samples are screened by Southern blotting using a BLG promoter probe (nucleotides 2523–4253 of SEQ ID NO: 7). Specific cleavages with appropriate restriction enzymes (e.g. Eco RI) allow the distinction of the three constructs containing the Aα, Bβ and γ sequences.

Southern blot analysis of transgenic mice prepared essentially as described above demonstrated that more than 50% of progeny contained all three fibrinogen sequences. Examination of milk from positive animals by reducing SDS polyacrylamide gel electrophoresis demonstrated the presence of all three protein chains at concentrations up to 1 mg/ml. The amount of fully assembled fibrinogen was related to the ratios of individual subunits present in the milk. No apparent phenotype was associated with high concentrations of human fibrinogen in mouse milk.

Example IV

Donor ewes are treated with an intravaginal progesterone-impregnated sponge (CHRONOGEST Goat Sponge, Intervet, Cambridge, UK) on day 0. Sponges are left in situ for ten or twelve days.

Superovulation is induced by treatment of donor ewes with a total of one unit of ovine follicle stimulating hormone (OFSH) (OVAGEN, Horizon Animal Reproduction Technology Pty. Ltd., New Zealand) administered in eight intramuscular injections of 0.125 units per injection starting at 5:00 pm on day −4 and ending at 8:00 am on day 0. Donors are injected intramuscularly with 0.5 ml of a luteolytic agent (ESTRUMATE, Vet-Drug) on day −4 to cause regression of the corpus luteum, to allow return to estrus and ovulation. To synchronize ovulation, the donor animals are injected intramuscularly with 2 ml of a synthetic releasing hormone analog (RECEPTAL, Vet-Drug) at 5:00 pm on day 0.

Donors are starved of food and water for at least 12 hours before artificial insemination (A.I.). The animals are artificially inseminated by intrauterine laparoscopy under sedation and local anesthesia on day 1. Either xylazine (ROMPUN, Vet-Drug) at a dose rate of 0.05–0.1 ml per 10 kg bodyweight or ACP injection 10 mg/ml (Vet-Drug) at a dose rate of 0.1 ml per 10 kg bodyweight is injected intramuscularly approximately fifteen minutes before A.I. to provide sedation. A.I. is carried out using freshly collected semen from a Poll Dorset ram. Semen is diluted with equal parts of filtered phosphate buffered saline, and 0.2 ml of the diluted semen is injected per uterine horn. Immediately pre- or post-A.I., donors are given an intramuscular injection of AMOXYPEN (Vet-Drug).

Fertilized eggs are recovered on day 2 following starvation of donors of food and water from 5:00 pm on day 1. Recovery is carried out under general anesthesia induced by an intravenous injection of 5% thiopentone sodium (INTRAVAL SODIUM, Vet-Drug) at a dose rate of 3 ml per 10 kg bodyweight. Anesthesia is maintained by inhalation of 1–2% Halothane/$O_2$/$N_2O$ after intubation. To recover the fertilized eggs, a laparotomy incision is made, and the uterus is exteriorized. The eggs are recovered by retrograde flushing of the oviducts with Ovum Culture Medium (Advanced Protein Products, Brierly Hill, West Midlands, UK) supplemented with bovine serum albumin of New Zealand origin. After flushing, the uterus is returned to the abdomen, and the incision is closed. Donors are allowed to recover post-operatively or are euthanized. Donors that are allowed to recover are given an intramuscular injection of Amoxypen L.A. at the manufacturer's recommended dose rate immediately pre- or post-operatively.

Plasmids containing the three fibrinogen chain expression units are digested with Mlu I, and the expression unit fragments are recovered and purified on sucrose density gradients. The fragment concentrations are determined by fluorimetry and diluted in Dulbecco's phosphate buffered saline without calcium and magnesium as described above. The concentration is adjusted to 6 µg/ml and approximately 2 pl of the mixture is microinjected into one pronucleus of each fertilized eggs with visible pronuclei.

All fertilized eggs surviving pronuclear microinjection are cultured in vitro at 38.5° C. in an atmosphere of 5% $CO_2$:5% $O_2$:90% $N_2$ and about ~100% humidity in a bicarbonate buffered synthetic oviduct medium (see Table) supplemented with 20% v/v vasectomized ram serum. The serum may be heat inactivated at 56° C. for 30 minutes and stored frozen at −20° C. prior to use. The fertilized eggs are cultured for a suitable period of time to allow early embryo mortality (caused by the manipulation techniques) to occur. These dead or arrested embryos are discarded. Embryos having developed to 5 or 6 cell divisions are transferred to synchronized recipient ewes.

TABLE

| Synthetic Oviduct Medium | |
|---|---|
| Stock A (Lasts 3 Months) | |
| NaCl | 6.29 g |
| KCl | 0.534 g |
| $KH_2SO_4$ | 0.162 g |
| $MgSO_4 \cdot 7H_2O$ | 0.182 g |
| Penicillin | 0.06 g |
| Sodium Lactate 60% syrup | 0.6 mls |
| Super $H_2O$ | 99.4 mls |
| Stock B (Lasts 2 weeks) | |
| $NaHCO_3$ | 0.21 g |
| Phenol red | 0.001 g |
| Super $H_2O$ | 10 mls |
| Stock C (Lasts 2 weeks) | |
| Sodium Pyruvate | 0.051 g |
| Super $H_2O$ | 10 mls |
| Stock D (Lasts 3 months) | |
| $CaCl_2 \cdot 2H_2O$ | 0.262 g |
| Super $H_2O$ | 10 mls |
| Stock E (Lasts 3 months) | |
| Hepes | 0.651 g |
| Phenol red | 0.001 g |
| Super $H_2O$ | 10 mls |
| To make up 10 mls of Bicarbonate Buffered Medium | |
| STOCK A | 1 ml |
| STOCK B | 1 ml |
| STOCK C | 0.07 ml |
| STOCK D | 0.1 ml |
| Super $H_2O$ | 7.83 ml |
| Osmolarity should be 265–285 mOsm. Add 2.5 ml of heat inactivated sheep serum and filter sterilize. | |
| To make up 10 mls HEPES Buffered Medium | |
| STOCK A | 1 ml |
| STOCK B | 0.2 ml |
| STOCK C | 0.07 ml |
| STOCK D | 0.1 ml |
| STOCK E | 0.8 ml |
| Super $H_2O$ | 7.83 ml |
| Osmolarity should be 265–285 mOsm. Add 2.5 ml of heat inactivated sheep serum and filter sterilize. | |

Recipient ewes are treated with an intravaginal progesterone-impregnated sponge (Chronogest Ewe Sponge or Chronogest Ewe-Lamb Sponge, Intervet) left in situ for 10 or 12 days. The ewes are injected intramuscularly with 1.5 ml (300 iu) of a follicle stimulating hormone substitute (P.M.S.G., Intervet) and with 0.5 ml of a luteolytic agent (Estrumate, Coopers Pitman-Moore) at sponge removal on day −1. The ewes are tested for estrus with a vasectomized ram between 8:00 am and 5:00 pm on days 0 and 1.

Embryos surviving in vitro culture are returned to recipients (starved from 5:00 pm on day 5 or 6) on day 6 or 7. Embryo transfer is carried out under general anesthesia as described above. The uterus is exteriorized via a laparotomy incision with or without laparoscopy. Embryos are returned to one or both uterine horns only in ewes with at least one suitable corpora lutea. After replacement of the uterus, the abdomen is closed, and the recipients are allowed to recover. The animals are given an intramuscular injection of Amoxypen L.A. at the manufacturer's recommended dose rate immediately pre- or post-operatively.

Lambs are identified by ear tags and left with their dams for rearing. Ewes and lambs are either housed and fed complete diet concentrates and other supplements and or ad lib. hay, or are let out to grass.

Within the first week of life (or as soon thereafter as possible without prejudicing health), each lamb is tested for the presence of the heterologous DNA by two sampling procedures. A 10 ml blood sample is taken from the jugular vein into an EDTA vacutainer. If fit enough, the lambs also have a second 10 ml blood sample taken within one week of the first. Tissue samples are taken by tail biopsy as soon as possible after the tail has become desensitized after the application of a rubber elastrator ring to its proximal third (usually within 200 minutes after "tailing"). The tissue is placed immediately in a solution of tail buffer. Tail samples are kept at room temperature and analyzed on the day of collection. All lambs are given an intramuscular injection of Amoxypen L.A. at the manufacturer's recommended dose rate immediately post-biopsy, and the cut end of the tail is sprayed with an antibiotic spray.

DNA is extracted from sheep blood by first separating white blood cells. A 10 ml sample of blood is diluted in 20 ml of Hank's buffered saline (HBS; obtained from Sigma Chemical Co.). Ten ml of the diluted blood is layered over 5 ml of Histopaque (Sigma) in each of two 15 ml screw-capped tubes. The tubes are centrifuged at 3000 rpm (2000× g max.), low brake for 15 minutes at room temperature. White cell interfaces are removed to a clean 15 ml tube and diluted to 15 ml in HBS. The diluted cells are spun at 3000 rpm for 10 minutes at room temperature, and the cell pellet is recovered and resuspended in 2–5 ml of tail buffer.

To extract DNA from the white cells, 10% SDS is added to the resuspended cells to a final concentration of 1%, and the tube is inverted to mix the solution. One mg of fresh proteinase K solution is added, and the mixture is incubated overnight at 45° C. DNA is extracted using an equal volume of phenol/chloroform (×3) and chloroform/isoamyl alcohol (×1). The DNA is then precipitated by adding 0.1 volume of 3M NaOAc and 2 volumes of ethanol, and the tube is inverted to mix. The precipitated DNA is spooled out using a clean glass rod with a sealed end. The spool is washed in 70% ethanol, and the DNA is allowed to partially dry, then is redissolved in TE (10 mM Tris-HCl, 1 mM EDTA, pH 7.4).

DNA samples from blood and tail are analyzed by Southern blotting using probes for the BLG promoter region and the fibrinogen chain coding regions.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for producing biocompetent fibrinogen comprising:

providing a first DNA segment encoding a secretion signal operably linked to a heterologous fibrinogen Aα chain, a second DNA segment encoding a secretion signal operably linked to a heterologous fibrinogen Bβ chain, and a third DNA segment encoding a secretion signal operably linked to a heterologous fibrinogen γ chain, wherein each chain is from the same species, and wherein each of said first, second and third segments is operably linked to additional DNA segments required for its expression in the mammary gland of a host female mammal;

introducing said DNA segments into a fertilized egg of a non-human mammalian species heterologous to the species of origin of said fibrinogen chains;

inserting said egg into an oviduct or uterus of a female of said mammalian species to obtain offspring carrying said DNA segments;

breeding said offspring to produce female progeny that express said first, second and third DNA segments and produce milk containing biocompetent fibrinogen encoded by said segments;

collecting milk from said female progeny; and and recovering the biocompetent fibrinogen from the milk.

2. A method according to claim 1 wherein said species into which said DNA segments are introduced is selected from the group consisting of sheep, pigs, goats, and cattle.

3. A method according to claim 1 wherein each of said first, second and third DNA segments comprises an intron.

4. A method according to claim 1 wherein the molar ratio of said first, second and third DNA segments is within the range of 0.5–1:0.5–1:0.5–1.

5. A method according to claim 1 wherein each of said first, second and third DNA segments is operably linked to a transcription promoter selected from the group consisting of casein, β-lactoglobulin, α-lactalbumin and whey acidic protein gene promoters.

6. A method according to claim 1 wherein said first, second and third DNA segments are expressed under the control of a β-lactoglobulin promoter.

7. A method according to claim 1 wherein said introducing step comprises injecting said first, second and third DNA segments into a pronucleus of said fertilized egg.

8. A method according to claim 1 wherein said fibrinogen is human fibrinogen.

9. A method according to claim 1 wherein said second DNA segment comprises a sequence of nucleotides as shown in SEQ ID NO: 3 from nucleotide 470 to nucleotide 8100.

10. A method according to claim 1 wherein said second DNA segment comprises a sequence of nucleotides as shown in SEQ ID NO: 3 from nucleotide 512 to nucleotide 8100.

11. A method according to claim 1 wherein said species into which said DNA segments is introduced is sheep.

12. A method of producing biocompetent fibrinogen comprising:

incorporating a first DNA segment encoding a secretion signal operably linked to an Aα chain of fibrinogen into a β-lactoglobulin gene to produce a first gene fusion comprising a β-lactoglobulin promoter operably linked to the first DNA segment;

incorporating a second DNA segment encoding a secretion signal operably linked to a Bβ chain of fibrinogen into a β-lactoglobulin gene to produce a second gene fusion comprising a β-lactoglobulin promoter operably linked to the second DNA segment;

incorporating a third DNA segment encoding a secretion signal operably linked to a γ chain of fibrinogen into a β-lactoglobulin gene to produce a third gene fusion comprising a β-lactoglobulin promoter operably linked to the third DNA segment wherein each of said first, second and third segments are of the same species;

introducing said first, second and third gene fusions into the germ line of a non-human mammal so that said DNA segments are expressed in a mammary gland of said mammal or its female progeny and biocompetent fibrinogen is secreted into milk of said mammal or its female progeny;

obtaining milk from said mammal or its female progeny; and recovering said fibrinogen from said milk.

13. A method according to claim 12 wherein said mammal is a sheep, pig, goat or cow.

14. A method according to claim 12 wherein each of said first, second and third gene fusions comprises an intron.

15. A method according to claim 12 wherein the molar ratio of said first, second and third gene fusions introduced is within the range of 0.5–1:0.5–1:0.5–1.

16. A method according to claim 12 wherein said introducing step comprises injecting said first, second and third gene fusions into a pronucleus of a fertilized egg and inserting said egg into an oviduct of a pseudopregnant female to produce female offspring carrying said gene fusions in the germ line, wherein said egg and said pseudopregnant female are of the same species.

17. A method according to claim 12 wherein said mammal is a sheep.

18. A method for producing biocompetent fibrinogen comprising:

providing a transgenic female non-human mammal carrying in its germline heterologous DNA segments encoding Aα, Bβ and γ chains of fibrinogen, wherein said segments are expressed in a mammary gland of said mammal and biocompetent fibrinogen encoded by said segments is secreted into milk of said mammal;

collecting milk from said mammal; and recovering said biocompetent fibrinogen from said milk.

19. A method according to claim 18 wherein said mammal is a sheep, pig, goat or cow.

20. A method according to claim 18 wherein said mammal is a sheep.

21. A transgenic non-human female mammal that produces recoverable amounts of biocompetent human fibrinogen in its milk, wherein said mammal comprises:

a first DNA segment encoding a secretion signal operably linked to a heterologous fibrinogen Aα chain, a second DNA segment encoding a secretion signal operably linked to a heterologous fibrinogen Bβ chain, and a third DNA segment encoding a secretion signal operably linked to a heterologous fibrinogen γ chain, and further wherein each chain is derived from the same species and is operably linked to additional DNA segments required for its expression in the mammary gland of a host female mammal.

22. A mammal according to claim 21 wherein said mammal is a sheep.

23. A process for producing a transgenic offspring of a mammal comprising:

providing a first DNA segment encoding a secretion signal operably linked to a heterologous fibrinogen Aα chain, a second DNA segment encoding a secretion signal operably linked to a heterologous fibrinogen Bβ chain, and a third DNA segment encoding a secretion signal operably linked to a heterologous fibrinogen γ chain, wherein each chain is derived from the same species, and wherein each of said first, second and third segments is operably linked to additional DNA segments required for its expression in the mammary gland of a host female mammal;

introducing said DNA segments into a fertilized egg of a non-human mammalian species heterologous to the species of origin of said fibrinogen chains;

inserting said fertilized egg into an oviduct or uterus of a female of said mammalian species; and allowing said fertilized egg to develop thereby producing transgenic offspring carrying said first, second and third DNA segments, wherein female progeny of said mammal express said DNA segments in a mammary gland to produce biocompetent fibrinogen.

24. A process according to claim 23 wherein said offspring is female.

25. A process according to claim 23 wherein said offspring is male.

26. A non-human mammal produced according to the process of claim 23.

27. A non-human mammal according to claim 26 wherein said mammal is female.

28. A non-human female mammal according to claim 27 that produces milk containing biocompetent fibrinogen encoded by said DNA segments.

29. A non-human mammal according to claim 26 wherein said mammal is male.

30. A non-human mammal carrying in its germline DNA segments encoding human Aα, Bβ and γ chains of fibrinogen, wherein female progeny of said mammal express said DNA segments in a mammary gland to produce biocompetent human fibrinogen.

31. A mammal non-human according to claim 30 wherein said mammal is female.

32. A mammal non-human according to claim 30 wherein said mammal is male.

33. A mammal according to claim 30, wherein said mammal is a sheep.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 5943 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: Human Fibrinogen A-alpha chain ( i x ) FEATURE:
        ( A ) NAME/KEY: CDS
        ( B ) LOCATION: join(31..84, 1154..1279, 1739..1922, 3055..3200, 3786..5210)

( x i ) SEQUENCE DESCRIPTION: SEQ ID NO:1:

```
GTCTAGGAGC CAGCCCCACC CTTAGAAAAG ATG TTT TCC ATG AGG ATC GTC TGC         54
                                 Met Phe Ser Met Arg Ile Val Cys
                                  1               5

CTA GTT CTA AGT GTG GTG GGC ACA GCA TGG GTATGGCCCT TTTCATTTTT           104
Leu Val Leu Ser Val Val Gly Thr Ala Trp
 10              15

TCTTCTTGCT TTCTCTCTGG TGTTTATTCC ACAAAGAGCC TGGAGGTCAG AGTCTACCTG       164

CTCTATGTCC TGACACACTC TTAGCTTTAT GACCCCAGGC CTGGGAGGAA ATTTCCTGGG       224
```

-continued

| | | | | | |
|---|---|---|---|---|---|
| TGGGCTTGAC | ACCTCAAGAA | TACAGGGTAA | TATGACACCA | AGAGGAAGAT | CTTAGATGGA | 284
| TGAGAGTGTA | CAACTACAAG | GGAAACTTTA | GCATCTGTCA | TTCAGTCTTA | CCACATTTTG | 344
| TTTTGTTTTG | TTTTAAAAAG | GGCAAGAATT | ATTTGCCATC | CTTGTACCTA | TAAAGCCTTG | 404
| GTGCATTATA | ATGCTAGTTA | ATGGAATAAA | ACATTTTATG | GTAAGATTTG | TTTTCTTTAG | 464
| TTATTAATTT | CTTGCTACTT | GTCCATAATA | AGCAGAACTT | TTAGTGTTAG | TACAGTTTTG | 524
| CTGAAAGGTT | ATTGTTGTGT | TTGTCAAGAC | AGAAGAAAAA | GCAAACGAAT | TATCTTTGGA | 584
| AATATCTTTG | CAGTATCAGA | AGAGATTAGT | TAGTAAGGCA | ATACGCTTTT | CCGCAGTAAT | 644
| GGTATTCTTT | TAAATTATGA | ATCCATCTCT | AAAGGTTACA | TAGAAACTTG | AAGGAGAGAG | 704
| GAACATTCAG | TTAAGATAGT | CTAGGTTTTT | CTACTGAAGC | AGCAATTACA | GGAGAAAGAG | 764
| CTCTACAGTA | GTTTCAACT | TTCTGTCTGC | AGTCATTAGT | AAAAATGAAA | AGGTAAAATT | 824
| TAACTGATTT | TATAGATTCA | AATAATTTTC | CTTTAGGAT | GGATTCTTTA | AAACTCCTAA | 884
| TATTTATCAA | ATGCTTATTT | AAGTGTCACA | CACAGTTAAG | AAATTTGTAC | ACCTTGTCTC | 944
| CTTAATTCT | CATAACAACT | CCATAAAATG | GGTCCTAGGA | TTTCCATTTG | AAGATAAGAA | 1004
| ACCTGAAGCT | TGCCGAAGCC | CTGTGTCTGC | TCTCCTTAAT | CTCTGTGAGA | GTGCCATCTC | 1064
| TTCCTGGGGA | CTTGTAGGCA | TGCCACTGTC | TCCTCTTCTG | GCTAACATTG | CTGTTGCTCT | 1124
| CTTTTGTGTA | TGTGAATGAA | TCTTTAAAG ACT | GCA | GAT AGT | GGT GAA GGT GAC | 1177
| | | Thr | Ala | Asp Ser | Gly Glu Gly Asp | 
| | | | 20 | | 25 |

```
TTT CTA GCT GAA GGA GGA GGC GTG CGT GGC CCA AGG GTT GTG GAA AGA    1225
Phe Leu Ala Glu Gly Gly Gly Val Arg Gly Pro Arg Val Val Glu Arg
        30                  35                  40

CAT CAA TCT GCC TGC AAA GAT TCA GAC TGG CCC TTC TGC TCT GAT GAA    1273
His Gln Ser Ala Cys Lys Asp Ser Asp Trp Pro Phe Cys Ser Asp Glu
    45                  50                      55

GAC TGG GTAAGCAGTC AGCGGGGGAA GCAGGAGATT CCTTCCCTCT GATGCTAGAG    1329
Asp Trp
    60
```

| | | | | | |
|---|---|---|---|---|---|
| GGGCTCACAG | GCTGACCTGA | TTGGTCCCAG | AAACTTTTTT | AAATAGAAAA | TAATTGAATA | 1389
| GTTACCTACA | TAGCAAATAA | AGAAAAGGAA | CCTACTCCCA | AGAGCACTGT | TTATTTACCT | 1449
| CCCCAACTCT | GGATCATTAG | TGGGTGAACA | GACAGGATTT | CAGTTGCATG | CTCAGGCAAA | 1509
| ACCAGGCTCC | TGAGTATTGT | GGCCTCAATT | TCCTGGCACC | TATTTATGGC | TAAGTGGACC | 1569
| CTCATTCCAG | AGTTTCTCTG | CGACCTCTAA | CTAGTCCTCT | TACCTACTTT | TAAGCCAACT | 1629
| TATCTGGAAG | AGAAAGGGTA | GGAAGAAATG | GGGGCTGCAT | GGAAACATGC | AAAATTATTC | 1689
| TGAATCTGAG | AGATAGATCC | TTACTGTAAT | TTTCTCCCTT | CACTTTCAG | AAC TAC | 1744
| | | | | | Asn Tyr |

```
AAA TGC CCT TCT GGC TGC AGG ATG AAA GGG TTG ATT GAT GAA GTC AAT    1792
Lys Cys Pro Ser Gly Cys Arg Met Lys Gly Leu Ile Asp Glu Val Asn
        65                  70                  75

CAA GAT TTT ACA AAC AGA ATA AAT AAG CTC AAA AAT TCA CTA TTT GAA    1840
Gln Asp Phe Thr Asn Arg Ile Asn Lys Leu Lys Asn Ser Leu Phe Glu
    80                  85                  90

TAT CAG AAG AAC AAT AAG GAT TCT CAT TCG TTG ACC ACT AAT ATA ATG    1888
Tyr Gln Lys Asn Asn Lys Asp Ser His Ser Leu Thr Thr Asn Ile Met
95                  100                 105                 110

GAA ATT TTG AGA GGC GAT TTT TCC TCA GCC AAT    A GTAAGTATTA        1932
Glu Ile Leu Arg Gly Asp Phe Ser Ser Ala Asn
            115                 120
```

| | | | | | |
|---|---|---|---|---|---|
| CATATTTACT | TCTTTGACTT | TATAACAGAA | ACAACAAAAA | TCCTAAATAA | ATATGATATC | 1992

```
CGCTTATATC TATGACAATT TCATCCCAAA GTACTTAGTG TAGAAACACA TACCTTCATA    2052
ATATCCCTGA AAATTTTAAG AGGGAGCTTT TGTTTTCGTT ATTTTTTCAA AGTAAAAGAT    2112
GTTAACTGAG ATTGTTAAG  GTCACAAAAT AAGTCAGAAT TTTGGATTAA ACAAGAATT     2172
TAAATGTGTT CTTTTCAACA GTATATACTG AAAGTAGGAT GGGTCAGACT CTTTGAGTTG    2232
ATATTTTGT  TTCTGCTTTG TAAAGGTGAA AACTGAGAGG TCAAGGAACT TGTTCAAAGA    2292
CACAGAGCTG GGAATTCAAC TCCCAGACTC CACTGAGCTG ATTAGGTAGA TTTTTAAATT    2352
TAAAATATAG GGTCAAGCTA CGTCATTCTC ACAGTCTACT CATTAGGGTT AGGAAACATT    2412
GCATTCACTC TGGGCATGGA CAGCGAGTCT AGGGAGTCCT CAGTTTCTCA AGTTTTGCTT    2472
TGCCTTTTTA CACCTTCACA AACACTTGAC ATTAAAATC  AGTGATGCCA ACACTAGCTG    2532
GCAAGTGAGT GATCCTGTTG ACCCAAAACA GCTTAGGAAC CATTTCAAAT CTATAGAGTT    2592
AAAAGAAAA  GCTCATCAGT AAGAAAATCC AATATGTTCA AGTCCCTTGA TTAAGGATGT    2652
TATAAAATAA TTGAAATGCA ATCAAACCAA CTATTTAAC  TCCAAATTAC ACCTTTAAAA    2712
TTCCAAAGAA AGTTCTTCTT CTATATTTCT TTGGGATTAC TAATTGCTAT TAGGACATCT    2772
TAACTGGCAT TCATGGAAGG CTGCAGGGCA TAACATTATC CAAAAGTCAA ATGCCCCATA    2832
GGTTTTGAAC TCACAGATTA AACTGTAACC AAAATAAAAT TAGGCATATT TACAAGCTAG    2892
TTTCTTTCTT TCTTTTTTCT CTTTCTTTCT TTCTTTCTTT CTTTCTTTCT TTCTTTCTTT    2952
CTTTCTTTCT TTCTCCTTCC TTCCTTTCTT CCTTTCTTTT TTGCTGGCAA TTACAGACAA    3012
ATCACTCAGC AGCTACTTCA ATAACCATAT TTTCGATTTC AG  AC CGT GAT AAT       3065
                                                 Asn Arg Asp Asn
                                                             125

ACC TAC AAC CGA GTG TCA GAG GAT CTG AGA AGC AGA ATT GAA GTC CTG      3113
Thr Tyr Asn Arg Val Ser Glu Asp Leu Arg Ser Arg Ile Glu Val Leu
            130                 135                 140

AAG CGC AAA GTC ATA GAA AAA GTA CAG CAT ATC CAG CTT CTG CAG AAA      3161
Lys Arg Lys Val Ile Glu Lys Val Gln His Ile Gln Leu Leu Gln Lys
        145                 150                 155

AAT GTT AGA GCT CAG TTG GTT GAT ATG AAA CGA CTG GAG GTAAGTATGT       3210
Asn Val Arg Ala Gln Leu Val Asp Met Lys Arg Leu Glu
    160                 165                 170

GGCTGTGGTC CCGAGTGTCC TTGTTTTGA  GTAGAGGGAA AAGGAAGGCG ATAGTTATGC    3270
ACTGAGTGTC TACTATATGC AGAGAAAAGT GTTATATCCA TCATCTACCT AAAAGTAGGT    3330
ATTATTTTCC TCACTCCACA GTTGAAGAAA AAAAAATTCA GAGATATTAA GTAAATTTTC    3390
CAACGTACAT AGATAGTAAT TCAAAGCAAT GTTCAGTCCC TGTCTATTCC AAGCCATTAC    3450
ATCACCACAC CTCTGAGCCC TCAGCCTGAG TTCACCAAGG ATCATTAAT  TAGCGTTTCC    3510
TTTGAGAGG  AATAGCACCT TACTCTTGAT CCATTCTGAG GCTAAGATGA ATTAAACAGC    3570
ATCCATTGCT TATCCTGGCT AGCCCTGCAA TACCCAACAT CTCTTCCACT GAGGGTGCTC    3630
GATAGGCAGA AACAGAGAA  TATTAAGTGG TAGGTCTCCG AGTCAAAAAA AATGAAACCA    3690
GTTCCAGAA  GGAAAATTAA CTACCAGGAA CTCAATAGAC GTAGTTTATG TATTTGTATC    3750
TACATTTTCT CTTTATTTTT CTCCCCTCTC TCTAG GTG GAC ATT GAT ATT AAG       3803
                                      Val Asp Ile Asp Ile Lys
                                                          175

ATC CGA TCT TGT CGA GGG TCA TGC AGT AGG GCT TTA GCT CGT GAA GTA      3851
Ile Arg Ser Cys Arg Gly Ser Cys Ser Arg Ala Leu Ala Arg Glu Val
            180                 185                 190

GAT CTG AAG GAC TAT GAA GAT CAG CAG AAG CAA CTT GAA CAG GTC ATT      3899
```

```
Asp Leu Lys Asp Tyr Glu Asp Gln Gln Lys Gln Leu Glu Gln Val Ile
    195             200             205

GCC AAA GAC TTA CTT CCC TCT AGA GAT AGG CAA CAC TTA CCA CTG ATA    3947
Ala Lys Asp Leu Leu Pro Ser Arg Asp Arg Gln His Leu Pro Leu Ile
    210             215             220

AAA ATG AAA CCA GTT CCA GAC TTG GTT CCC GGA AAT TTT AAG AGC CAG    3995
Lys Met Lys Pro Val Pro Asp Leu Val Pro Gly Asn Phe Lys Ser Gln
225             230             235             240

CTT CAG AAG GTA CCC CCA GAG TGG AAG GCA TTA ACA GAC ATG CCG CAG    4043
Leu Gln Lys Val Pro Pro Glu Trp Lys Ala Leu Thr Asp Met Pro Gln
        245             250             255

ATG AGA ATG GAG TTA GAG AGA CCT GGT GGA AAT GAG ATT ACT CGA GGA    4091
Met Arg Met Glu Leu Glu Arg Pro Gly Gly Asn Glu Ile Thr Arg Gly
        260             265             270

GGC TCC ACC TCT TAT GGA ACC GGA TCA GAG ACG GAA AGC CCC AGG AAC    4139
Gly Ser Thr Ser Tyr Gly Thr Gly Ser Glu Thr Glu Ser Pro Arg Asn
            275             280             285

CCT AGC AGT GCT GGA AGC TGG AAC TCT GGG AGC TCT GGA CCT GGA AGT    4187
Pro Ser Ser Ala Gly Ser Trp Asn Ser Gly Ser Ser Gly Pro Gly Ser
    290             295             300

ACT GGA AAC CGA AAC CCT GGG AGC TCT GGG ACT GGA GGG ACT GCA ACC    4235
Thr Gly Asn Arg Asn Pro Gly Ser Ser Gly Thr Gly Gly Thr Ala Thr
305             310             315             320

TGG AAA CCT GGG AGC TCT GGA CCT GGA AGT GCT GGA AGC TGG AAC TCT    4283
Trp Lys Pro Gly Ser Ser Gly Pro Gly Ser Ala Gly Ser Trp Asn Ser
        325             330             335

GGG AGC TCT GGA ACT GGA AGT ACT GGA AAC CAA AAC CCT GGG AGC CCT    4331
Gly Ser Ser Gly Thr Gly Ser Thr Gly Asn Gln Asn Pro Gly Ser Pro
            340             345             350

AGA CCT GGT AGT ACC GGA ACC TGG AAT CCT GGC AGC TCT GAA CGC GGA    4379
Arg Pro Gly Ser Thr Gly Thr Trp Asn Pro Gly Ser Ser Glu Arg Gly
        355             360             365

AGT GCT GGG CAC TGG ACC TCT GAG AGC TCT GTA TCT GGT AGT ACT GGA    4427
Ser Ala Gly His Trp Thr Ser Glu Ser Ser Val Ser Gly Ser Thr Gly
        370             375             380

CAA TGG CAC TCT GAA TCT GGA AGT TTT AGG CCA GAT AGC CCA GGC TCT    4475
Gln Trp His Ser Glu Ser Gly Ser Phe Arg Pro Asp Ser Pro Gly Ser
385             390             395             400

GGG AAC GCG AGG CCT AAC AAC CCA GAC TGG GGC ACA TTT GAA GAG GTG    4523
Gly Asn Ala Arg Pro Asn Asn Pro Asp Trp Gly Thr Phe Glu Glu Val
            405             410             415

TCA GGA AAT GTA AGT CCA GGG ACA AGG AGA GAG TAC CAC ACA GAA AAA    4571
Ser Gly Asn Val Ser Pro Gly Thr Arg Arg Glu Tyr His Thr Glu Lys
            420             425             430

CTG GTC ACT TCT AAA GGA GAT AAA GAG CTC AGG ACT GGT AAA GAG AAG    4619
Leu Val Thr Ser Lys Gly Asp Lys Glu Leu Arg Thr Gly Lys Glu Lys
        435             440             445

GTC ACC TCT GGT AGC ACA ACC ACG CGT CGT TCA TGC TCT AAA ACC    4667
Val Thr Ser Gly Ser Thr Thr Thr Arg Arg Ser Cys Ser Lys Thr
    450             455             460

GTT ACT AAG ACT GTT ATT GGT CCT GAT GGT CAC AAA GAA GTT ACC AAA    4715
Val Thr Lys Thr Val Ile Gly Pro Asp Gly His Lys Glu Val Thr Lys
465             470             475             480

GAA GTG GTG ACC TCC GAA GAT GGT TCT GAC TGT CCC GAG GCA ATG GAT    4763
Glu Val Val Thr Ser Glu Asp Gly Ser Asp Cys Pro Glu Ala Met Asp
            485             490             495

TTA GGC ACA TTG TCT GGC ATA GGT ACT CTG GAT GGG TTC CGC CAT AGG    4811
Leu Gly Thr Leu Ser Gly Ile Gly Thr Leu Asp Gly Phe Arg His Arg
            500             505             510

CAC CCT GAT GAA GCT GCC TTC TTC GAC ACT GCC TCA ACT GGA AAA ACA    4859
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| His | Pro | Asp | Glu | Ala | Ala | Phe | Phe | Asp | Thr | Ala | Ser | Thr | Gly | Lys | Thr |      |
|     |     | 515 |     |     |     |     | 520 |     |     |     |     | 525 |     |     |     |      |
| TTC | CCA | GGT | TTC | TTC | TCA | CCT | ATG | TTA | GGA | GAG | TTT | GTC | AGT | GAG | ACT | 4907 |
| Phe | Pro | Gly | Phe | Phe | Ser | Pro | Met | Leu | Gly | Glu | Phe | Val | Ser | Glu | Thr |      |
|     | 530 |     |     |     |     | 535 |     |     |     |     | 540 |     |     |     |     |      |
| GAG | TCT | AGG | GGC | TCA | GAA | TCT | GGC | ATC | TTC | ACA | AAT | ACA | AAG | GAA | TCC | 4955 |
| Glu | Ser | Arg | Gly | Ser | Glu | Ser | Gly | Ile | Phe | Thr | Asn | Thr | Lys | Glu | Ser |      |
| 545 |     |     |     |     | 550 |     |     |     |     | 555 |     |     |     |     | 560 |      |
| AGT | TCT | CAT | CAC | CCT | GGG | ATA | GCT | GAA | TTC | CCT | TCC | CGT | GGT | AAA | TCT | 5003 |
| Ser | Ser | His | His | Pro | Gly | Ile | Ala | Glu | Phe | Pro | Ser | Arg | Gly | Lys | Ser |      |
|     |     |     |     | 565 |     |     |     |     | 570 |     |     |     |     | 575 |     |      |
| TCA | AGT | TAC | AGC | AAA | CAA | TTT | ACT | AGT | AGC | ACG | AGT | TAC | AAC | AGA | GGA | 5051 |
| Ser | Ser | Tyr | Ser | Lys | Gln | Phe | Thr | Ser | Ser | Thr | Ser | Tyr | Asn | Arg | Gly |      |
|     |     |     | 580 |     |     |     |     |     | 585 |     |     |     |     | 590 |     |      |
| GAC | TCC | ACA | TTT | GAA | AGC | AAG | AGC | TAT | AAA | ATG | GCA | GAT | GAG | GCC | GGA | 5099 |
| Asp | Ser | Thr | Phe | Glu | Ser | Lys | Ser | Tyr | Lys | Met | Ala | Asp | Glu | Ala | Gly |      |
|     |     | 595 |     |     |     |     | 600 |     |     |     |     | 605 |     |     |     |      |
| AGT | GAA | GCC | GAT | CAT | GAA | GGA | ACA | CAT | AGC | ACC | AAG | AGA | GGC | CAT | GCT | 5147 |
| Ser | Glu | Ala | Asp | His | Glu | Gly | Thr | His | Ser | Thr | Lys | Arg | Gly | His | Ala |      |
|     * | 610 |     |     |     |     | 615 |     |     |     |     | 620 |     |     |     |     |      |
| AAA | TCT | CGC | CCT | GTC | AGA | GGT | ATC | CAC | ACT | TCT | CCT | TTG | GGG | AAG | CCT | 5195 |
| Lys | Ser | Arg | Pro | Val | Arg | Gly | Ile | His | Thr | Ser | Pro | Leu | Gly | Lys | Pro |      |
| 625 |     |     |     | 630 |     |     |     |     | 635 |     |     |     |     | 640 |     |      |
| TCC | CTG | TCC | CCC | TAGACTAAGT | TAAATATTTC | TGCACAGTGT | TCCCATGGCC |     |     |     |     |     |     |     |     | 5247 |
| Ser | Leu | Ser | Pro |     |     |     |     |     |     |     |     |     |     |     |     |      |
|     |     |     | 645 |     |     |     |     |     |     |     |     |     |     |     |     |      |

| | | | | |
|---|---|---|---|---|
| CCTTGCATTT | CCTTCTTAAC | TCTCTGTTAC | ACGTCATTGA | AACTACACTT TTTTGGTCTG | 5307 |
| TTTTGTGCT | AGACTGTAAG | TTCCTTGGGG | GCAGGGCCTT | TGTCTGTCTC ATCTCTGTAT | 5367 |
| TCCCAAATGC | CTAACAGTAC | AGAGCCATGA | CTCAATAAAT | ACATGTTAAA TGGATGAATG | 5427 |
| AATTCCTCTG | AAACTCTATT | TGAGCTTATT | TAGTCAAATT | CTTTCACTAT TCAAAGTGTG | 5487 |
| TGCTATTAGA | ATTGTCACCC | AACTGATTAA | TCACATTTTT | AGTATGTGTC TCAGTTGACA | 5547 |
| TTAGGTCAG | GCTAAATACA | AGTTGTGTTA | GTATTAAGTG | AGCTTAGCTA CCTGTACTGG | 5607 |
| TTACTTGCTA | TTAGTTTGTG | CAAGTAAAAT | TCCAAATACA | TTTGAGGAAA ATCCCCTTTG | 5667 |
| CAATTTGTAG | GTATAAATAA | CCGCTTATTT | GCATAAGTTC | TATCCCACTG TAAGTGCATC | 5727 |
| CTTTCCCTAT | GGAGGGAAGG | AAAGGAGGAA | GAAAGAAAGG | AAGGGAAAGA AACAGTATTT | 5787 |
| GCCTTATTTA | ATCTGAGCCG | TGCCTATCTT | TGTAAAGTTA | AATGAGAATA ACTTCTTCCA | 5847 |
| ACCAGCTTAA | TTTTTTTTT | AGACTGTGAT | GATGTCCTCC | AAACACATCC TTCAGGTACC | 5907 |
| CAAAGTGGCA | TTTTCAATAT | CAAGCTATCC | GGATCC |  | 5943 |

( 2 ) INFORMATION FOR SEQ ID NO:2:

( i ) SEQUENCE CHARACTERISTICS:
        ( A ) LENGTH: 644 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Phe | Ser | Met | Arg | Ile | Val | Cys | Leu | Val | Leu | Ser | Val | Val | Gly | Thr |
| 1 |  |  |  | 5 |  |  |  |  | 10 |  |  |  |  | 15 |  |
| Ala | Trp | Thr | Ala | Asp | Ser | Gly | Glu | Gly | Asp | Phe | Leu | Ala | Glu | Gly | Gly |
|  |  |  | 20 |  |  |  |  | 25 |  |  |  |  | 30 |  |  |
| Gly | Val | Arg | Gly | Pro | Arg | Val | Val | Glu | Arg | His | Gln | Ser | Ala | Cys | Lys |
|  |  |  | 35 |  |  |  |  | 40 |  |  |  |  | 45 |  |  |

```
Asp  Ser  Asp  Trp  Pro  Phe  Cys  Ser  Asp  Glu  Asp  Trp  Asn  Tyr  Lys  Cys
     50                       55                       60

Pro  Ser  Gly  Cys  Arg  Met  Lys  Gly  Leu  Ile  Asp  Glu  Val  Asn  Gln  Asp
65                       70                       75                       80

Phe  Thr  Asn  Arg  Ile  Asn  Lys  Leu  Lys  Asn  Ser  Leu  Phe  Glu  Tyr  Gln
                    85                       90                       95

Lys  Asn  Asn  Lys  Asp  Ser  His  Ser  Leu  Thr  Thr  Asn  Ile  Met  Glu  Ile
               100                      105                      110

Leu  Arg  Gly  Asp  Phe  Ser  Ser  Ala  Asn  Asn  Arg  Asp  Asn  Thr  Tyr  Asn
          115                      120                      125

Arg  Val  Ser  Glu  Asp  Leu  Arg  Ser  Arg  Ile  Glu  Val  Leu  Lys  Arg  Lys
     130                      135                      140

Val  Ile  Glu  Lys  Val  Gln  His  Ile  Gln  Leu  Leu  Gln  Lys  Asn  Val  Arg
145                      150                      155                      160

Ala  Gln  Leu  Val  Asp  Met  Lys  Arg  Leu  Glu  Val  Asp  Ile  Asp  Ile  Lys
                    165                      170                      175

Ile  Arg  Ser  Cys  Arg  Gly  Ser  Cys  Ser  Arg  Ala  Leu  Ala  Arg  Glu  Val
               180                      185                      190

Asp  Leu  Lys  Asp  Tyr  Glu  Asp  Gln  Gln  Lys  Gln  Leu  Glu  Gln  Val  Ile
          195                      200                      205

Ala  Lys  Asp  Leu  Leu  Pro  Ser  Arg  Asp  Arg  Gln  His  Leu  Pro  Leu  Ile
     210                      215                      220

Lys  Met  Lys  Pro  Val  Pro  Asp  Leu  Val  Pro  Gly  Asn  Phe  Lys  Ser  Gln
225                      230                      235                      240

Leu  Gln  Lys  Val  Pro  Pro  Glu  Trp  Lys  Ala  Leu  Thr  Asp  Met  Pro  Gln
                    245                      250                      255

Met  Arg  Met  Glu  Leu  Glu  Arg  Pro  Gly  Gly  Asn  Glu  Ile  Thr  Arg  Gly
               260                      265                      270

Gly  Ser  Thr  Ser  Tyr  Gly  Thr  Gly  Ser  Glu  Thr  Glu  Ser  Pro  Arg  Asn
          275                      280                      285

Pro  Ser  Ala  Gly  Ser  Trp  Asn  Ser  Gly  Ser  Ser  Gly  Pro  Gly  Ser
     290                      295                      300

Thr  Gly  Asn  Arg  Asn  Pro  Gly  Ser  Ser  Gly  Thr  Gly  Gly  Thr  Ala  Thr
305                      310                      315                      320

Trp  Lys  Pro  Gly  Ser  Ser  Gly  Pro  Gly  Ser  Ala  Gly  Ser  Trp  Asn  Ser
                    325                      330                      335

Gly  Ser  Ser  Gly  Thr  Gly  Ser  Thr  Gly  Asn  Gln  Asn  Pro  Gly  Ser  Pro
               340                      345                      350

Arg  Pro  Gly  Ser  Thr  Gly  Thr  Trp  Asn  Pro  Gly  Ser  Ser  Glu  Arg  Gly
          355                      360                      365

Ser  Ala  Gly  His  Trp  Thr  Ser  Glu  Ser  Ser  Val  Ser  Gly  Ser  Thr  Gly
     370                      375                      380

Gln  Trp  His  Ser  Glu  Ser  Gly  Ser  Phe  Arg  Pro  Asp  Ser  Pro  Gly  Ser
385                      390                      395                      400

Gly  Asn  Ala  Arg  Pro  Asn  Asn  Pro  Asp  Trp  Gly  Thr  Phe  Glu  Glu  Val
                    405                      410                      415

Ser  Gly  Asn  Val  Ser  Pro  Gly  Thr  Arg  Arg  Glu  Tyr  His  Thr  Glu  Lys
               420                      425                      430

Leu  Val  Thr  Ser  Lys  Gly  Asp  Lys  Glu  Leu  Arg  Thr  Gly  Lys  Glu  Lys
          435                      440                      445

Val  Thr  Ser  Gly  Ser  Thr  Thr  Thr  Thr  Arg  Arg  Ser  Cys  Ser  Lys  Thr
     450                      455                      460

Val  Thr  Lys  Thr  Val  Ile  Gly  Pro  Asp  Gly  His  Lys  Glu  Val  Thr  Lys
465                      470                      475                      480
```

| Glu | Val | Val | Thr | Ser | Glu | Asp | Gly | Ser | Asp | Cys | Pro | Glu | Ala | Met | Asp |
|  |  |  |  | 485 |  |  |  |  | 490 |  |  |  |  | 495 |  |

| Leu | Gly | Thr | Leu | Ser | Gly | Ile | Gly | Thr | Leu | Asp | Gly | Phe | Arg | His | Arg |
|  |  |  | 500 |  |  |  |  |  | 505 |  |  |  | 510 |  |  |

| His | Pro | Asp | Glu | Ala | Ala | Phe | Phe | Asp | Thr | Ala | Ser | Thr | Gly | Lys | Thr |
|  |  | 515 |  |  |  |  | 520 |  |  |  |  | 525 |  |  |  |

| Phe | Pro | Gly | Phe | Phe | Ser | Pro | Met | Leu | Gly | Glu | Phe | Val | Ser | Glu | Thr |
|  | 530 |  |  |  |  | 535 |  |  |  |  | 540 |  |  |  |  |

| Glu | Ser | Arg | Gly | Ser | Glu | Ser | Gly | Ile | Phe | Thr | Asn | Thr | Lys | Glu | Ser |
| 545 |  |  |  |  | 550 |  |  |  |  | 555 |  |  |  |  | 560 |

| Ser | Ser | His | His | Pro | Gly | Ile | Ala | Glu | Phe | Pro | Ser | Arg | Gly | Lys | Ser |
|  |  |  |  | 565 |  |  |  |  | 570 |  |  |  |  | 575 |  |

| Ser | Ser | Tyr | Ser | Lys | Gln | Phe | Thr | Ser | Ser | Thr | Ser | Tyr | Asn | Arg | Gly |
|  |  |  | 580 |  |  |  |  | 585 |  |  |  |  | 590 |  |  |

| Asp | Ser | Thr | Phe | Glu | Ser | Lys | Ser | Tyr | Lys | Met | Ala | Asp | Glu | Ala | Gly |
|  |  | 595 |  |  |  |  | 600 |  |  |  |  | 605 |  |  |  |

| Ser | Glu | Ala | Asp | His | Glu | Gly | Thr | His | Ser | Thr | Lys | Arg | Gly | His | Ala |
|  | 610 |  |  |  |  | 615 |  |  |  |  | 620 |  |  |  |  |

| Lys | Ser | Arg | Pro | Val | Arg | Gly | Ile | His | Thr | Ser | Pro | Leu | Gly | Lys | Pro |
| 625 |  |  |  | 630 |  |  |  |  | 635 |  |  |  |  |  | 640 |

| Ser | Leu | Ser | Pro |

( 2 ) INFORMATION FOR SEQ ID NO:3:

( i ) SEQUENCE CHARACTERISTICS:
        ( A ) LENGTH: 8878 base pairs
        ( B ) TYPE: nucleic acid
        ( C ) STRANDEDNESS: double
        ( D ) TOPOLOGY: linear ( i i ) MOLECULE TYPE: DNA (genomic)

( v i i ) IMMEDIATE SOURCE:
        ( B ) CLONE: human fibrinogen B-beta chain ( i x ) FEATURE:
        ( A ) NAME/KEY: misc_RNA
        ( B ) LOCATION: 1..469

( i x ) FEATURE:
        ( A ) NAME/KEY: exon
        ( B ) LOCATION: 470..583

( i x ) FEATURE:
        ( A ) NAME/KEY: intron
        ( B ) LOCATION: 584..3257

( i x ) FEATURE:
        ( A ) NAME/KEY: exon
        ( B ) LOCATION: 3258..3449

( i x ) FEATURE:
        ( A ) NAME/KEY: intron
        ( B ) LOCATION: 3450..3938

( i x ) FEATURE:
        ( A ) NAME/KEY: exon
        ( B ) LOCATION: 3939..4122

( i x ) FEATURE:
        ( A ) NAME/KEY: intron
        ( B ) LOCATION: 4123..5042

( i x ) FEATURE:
        ( A ) NAME/KEY: exon
        ( B ) LOCATION: 5043..5270

( i x ) FEATURE:

(A) NAME/KEY: intron
            (B) LOCATION: 5271..5830

(ix) FEATURE:
            (A) NAME/KEY: exon
            (B) LOCATION: 5831..5944

(ix) FEATURE:
            (A) NAME/KEY: intron
            (B) LOCATION: 5945..6632

(ix) FEATURE:
            (A) NAME/KEY: exon
            (B) LOCATION: 6633..6758

(ix) FEATURE:
            (A) NAME/KEY: intron
            (B) LOCATION: 6759..6966

(ix) FEATURE:
            (A) NAME/KEY: exon
            (B) LOCATION: 6967..7252

(ix) FEATURE:
            (A) NAME/KEY: intron
            (B) LOCATION: 7253..7870

(ix) FEATURE:
            (A) NAME/KEY: exon
            (B) LOCATION: 7871..8102

(ix) FEATURE:
            (A) NAME/KEY: 3'UTR
            (B) LOCATION: 8103..8537

(ix) FEATURE:
            (A) NAME/KEY: misc_RNA
            (B) LOCATION: 8538..8878

(ix) FEATURE:
            (A) NAME/KEY: CDS
            (B) LOCATION: join(470..583, 3258..3449, 3939..4122,
                  5043..5270, 5831..5944, 6633..6758, 6967..7252,
                  7871..8102)

(xi) SEQUENCE DESCRIPTION: SEQ ID NO:3:

```
GAATTCATGC CCCTTTTGAA ATAGACTTAT GTCATTGTCA GAAAACATAA GCATTTATGG        60

TATATCATTA ATGAGTCACG ATTTTAGTGG TTGCCTTGTG AGTAGGTCAA ATTTACTAAG       120

CTTAGATTTG TTTTCTCACA TATTCTTTCG GAGCTTGTGT AGTTTCCACA TTAATTTACC       180

AGAAACAAGA TACACACTCT CTTTGAGGAG TGCCCTAACT TCCCATCATT TTGTCCAATT       240

AAATGAATTG AAGAAATTTA ATGTTTCTAA ACTAGACCAA CAAAGAATAA TAGTTGTATG       300

ACAAGTAAAT AAGCTTTGCT GGGAAGATGT TGCTTAAATG ATAAATGGT TCAGCCAACA        360

AGTGAACCAA AAATTAAATA TTAACTAAGG AAAGGTAACC ATTTCTGAAG TCATTCCTAG       420

CAGAGGACTC AGATATATAT AGGATTGAAG ATCTCTCAGT TAAGTCTAC ATG AAA          475
                                                      Met Lys
                                                        1
```

```
AGG ATG GTT TCT TGG AGC TTC CAC AAA CTT AAA ACC ATG AAA CAT CTA        523
Arg Met Val Ser Trp Ser Phe His Lys Leu Lys Thr Met Lys His Leu
        5                   10                  15

TTA TTG CTA CTA TTG TGT GTT TTT CTA GTT AAG TCC CAA GGT GTC AAC        571
Leu Leu Leu Leu Leu Cys Val Phe Leu Val Lys Ser Gln Gly Val Asn
    20                  25                  30

GAC AAT GAG GAG GTGAATTTTT TAAAGCATTA TTATATTATT AGTAGTATTA            623
Asp Asn Glu Glu
 35
```

```
TTAATATAAG ATGTAACATA ATCATATTAT GTGCTTATTT TAATGAAATT AGCATTGCTT      683
```

```
ATAGTTATGA AATGGAATTG TTAACCTCTG ACTTATTGTA TTTAAAGAAT GTTTCATAGT      743
ATTTCTTATA TAAAAACAAA GTAATTTCTT GTTTTCTAGT TTATCACCTT TGTTTTCTTA      803
AGATGAGGAT GGCTTAGCTA ATGTAAGATG TGTTTTTCTC ACTTGCTATT CTGAGTACTG      863
TGATTTTCAT TTACTTCTAG CAATACAGGA TTACAATTAA GAGGACAAGA TCTGAAAATC      923
TCACAAACTA TAAAATAATA AAGAGCAGA  ATTTAAGAT  AAAAGAAACT GGTGGTAGGT      983
AGATTGTTCT TTGGTGAAGG AAGGTAATAT ATATTGTTAC TGAGATTACT ATTTATAAAA     1043
ATTATAACTA AGCCTAAAAG CAAATACAT  CAAGTGTAAT GATAGAAAAT GAAATATTGC     1103
TTTTTCAGA  TGAAAAGTTC AAATTAGAGT TAGTGTGTAT TGTTATTATT AATAGTTATG     1163
AAACACGGTT CAGTCTAATT TATTTATTTG TAGAACAGTT TGTCCTCAAC TATTATTTTT     1223
GCTGACTTAT TGCTGTTAAT TTGCAGTTAC TAAAAATACA GAAATGCATT TAGGACAATG     1283
GATATTTAAG AAATTTAAAT TTTATCATCA AACGTATCAT GGCCAAATTT CTTACATATA     1343
GCATAGTATC ATTAAACTAG AAATAAGAAT ACACAATAAT ATTTAAATGA AGTGATTCAT     1403
TTCGGATCAT TATTGAGTTT CAAGGGAACT TGAGTGTTGT ACTTATCAGA CTCTACATGT     1463
AAGAACATAT AGTTAATCTG GTTGTGTGTG TAAAAACATA TGGTTAATCT GGTTAAGTCT     1523
GGTTAATCAT ATTAGGTAAG AAAAATGTAA AGAATGTGTA AGACGAAATT TTTGTAAAGT     1583
ACTCTGCAAA GCACTTTCAC ATTTCTGCTT ATCAACTAAA CCTCACAGAG ATAGTTTAAT     1643
AGTTAGGCT  TTAAAATGGA TTTTGATTAT TCAACAAGTG GCCTTCATAA TTTCTTTAAG     1703
TGTTTTCTT  TAAGTATATA CTTTCTTTAA ATATTTTTA  AAATTTCCTT TTCTCTAGTA     1763
AAGCCAGACC ATCCATGCTA CCTCTCTAGT GGCACTCTGA AATAAAAAGA AAATAGTTTT     1823
CTCTGTTATA ATTGTATTTG TAATAAGCAG ATGAATCACA TTTCTTAAAA TTTGTTTTAG     1883
AGAGGGTAAG CTCTGACTAG GACCATGACT TCAATGTGAA ATATGTATAT ATCCTCCGAA     1943
TCTTTACATA TTAAGAATGT ATATAGTCAA CTGGTTAAAC AGGAAAATCT GGAACAGCCT     2003
GGCTGGGTTT TAATCTTAGC ACCATCCTAC TAAATGTTAA ATAATATTAT AATCTAATGA     2063
ATAAATGACA ATGCAATTCC AAATAGAGTT CATCTGATGA CTTCTAGACT CACAAAATTG     2123
CAAGAGAGCT CAGTTGTTGC TCAGTTGTTC CAAATCATGT CGTTTGTTAA TTTGTAATTA     2183
AGCTCCAAAG GATGTATAGC TACTGACAAA AAAAAAAATG AGAATGTAGT TAATCCAAAT     2243
CAAAACTTTC CTATTGCAAT GCGTATTTTC TGCTTCATTA TCCTTTAATA TAATATTTTA     2303
AGTTAGCAAG TAATTTTAAT TACAATGCAC AAGCCTTGAG AATTATTTTA AATATAAGAA     2363
AATCATAATG TTTGATAAAG AAATCATGTA AGAAATTTCA AGATAATGGT TTAACAAATA     2423
ATTTGTTGA  TAGAAGATAA GACTAAAAGT GAAATTCGAA GTGGAGAGGA CACTTAAACT     2483
GTAGTACTTG TTATGTGTGA TTCCAGTAAA AATAGTAATG AGCACTTATT ATTGCCAAGT     2543
ACTGTTCTGA GGGTACCATA TGCAATAAGT TATTTAATCC TTACAATAAT CTTGTAAGGC     2603
AGATTCAAAC TATCATTACA CTTATTTTAC AGATGAGAAA ACTGGGGCAC AGATAAAGCA     2663
ACTTGCCCAA GGTCTCATAG CTGTAAGTCA ACCCTACGGT CAAGACCTAC AAGTAGCCGA     2723
GCTCCAGAGT ACATTATGAG GGTCAAAGAT TGTCTTATTA CAAATAAATT CCAAGTAGAA     2783
TCAACCTTTA ATAAGTCTTT AATGTCTCTT AAATATGTTT ATATAGGAGT CTAATCACCA     2843
ATTCACAAAA ATGAAAGTAG GGAAATGATT AACAATAATC ATAGGAATCT AACAATCCAA     2903
GTGGCTTGAG AATATTCATT CTTCTTGACA GTATAGATTC TTTACAATTT CGTAAGTTCC     2963
AATGTATGTT TTAGGAATAT GAGGTCATTA CTATTCATAA TCTGATACAG CTTTATCCTA     3023
AGGCCTCTCT TTAAAAACTA CACTGCATCA TAGCTTTTTT GTGCAGTTGG TCTTTCTACT     3083
```

| | |
|---|---|
| GTTACTGAAC AGTAAGCAAC CTACAGATTC ACTATCACCA ACCAGCCAGT TGATGGATCT | 3143 |
| TAAGCAAATT ATCAAGCTTG TGATAACCTA AATTATAAAA TGAGGGTGTT GGAATAGTTA | 3203 |
| CATTCCAAAT CTTCTATAAC ACTCTGTATT ATATTCTGC CTCATTCCTT GTAG GGT | 3260 |

```
                                                                   Gly
TTC TTC AGT GCC CGT GGT CAT CGA CCC CTT GAC AAG AAG AGA GAA GAG    3308
Phe Phe Ser Ala Arg Gly His Arg Pro Leu Asp Lys Lys Arg Glu Glu
 40              45              50              55

GCT CCC AGC CTG AGG CCT GCC CCA CCG CCC ATC AGT GGA GGT GGC TAT    3356
Ala Pro Ser Leu Arg Pro Ala Pro Pro Pro Ile Ser Gly Gly Gly Tyr
             60              65              70

CGG GCT CGT CCA GCC AAA GCA GCT GCC ACT CAA AAG AAA GTA GAA AGA    3404
Arg Ala Arg Pro Ala Lys Ala Ala Ala Thr Gln Lys Lys Val Glu Arg
 75              80              85

AAA GCC CCT GAT GCT GGA GGC TGT CTT CAC GCT GAC CCA GAC CTG        3449
Lys Ala Pro Asp Ala Gly Gly Cys Leu His Ala Asp Pro Asp Leu
         90              95             100
```

| | |
|---|---|
| GTGGGTGCAC TGATGTTTCT TGCAGTGGTG GCTCTCTCAT GCAGAGAAAG CCTGTAGTCA | 3509 |
| TGGCAGTCTG CTAATGTTTC ACTGACCCAC ATTACCATCA CTGTTATTTT GTTTGTTTAT | 3569 |
| TTTGGAAATA AAATTCAAAA CATAAACATA TTGGGCCTTT GGTTTAGGCT TTCTTTCTTG | 3629 |
| TTTCTTTGG TCTGGGCCCA AAATTTCAAA TTAGGATATG TGGGTGCCAC CTTTCCATTT | 3689 |
| GTATTTGCC ACTGCCTTTG TTTAGTTGGT AAAATTTCA TAGCCCAATT ATATTTTTC | 3749 |
| TGGGGTAAGT AATATTTTAA ATCTCTATGA GAGTATGATG ATGACTTTCG AATTCTGGT | 3809 |
| CTTACAGAAA ACCAAATAAT AAATTTTTAT GTTGGCTAAT CGTATCGCTG AATTTCCTA | 3869 |
| TGTGCTATTT TAACAAATGT CCATGACCCA AATCCTTCAT CTAATGCCTG CTATTTCTT | 3929 |
| TGTTTTTAG GGG GTG TTG TGT CCT ACA GGA TGT CAG TTG CAA GAG GCT | 3977 |

```
         Gly Val Leu Cys Pro Thr Gly Cys Gln Leu Gln Glu Ala
             105             110             115

TTG CTA CAA CAG GAA AGG CCA ATC AGA AAT AGT GTT GAT GAG TTA AAT    4025
Leu Leu Gln Gln Glu Arg Pro Ile Arg Asn Ser Val Asp Glu Leu Asn
             120             125             130

AAC AAT GTG GAA GCT GTT TCC CAG ACC TCC TCT TCT TCC TTT CAG TAC    4073
Asn Asn Val Glu Ala Val Ser Gln Thr Ser Ser Ser Ser Phe Gln Tyr
         135             140             145

ATG TAT TTG CTG AAA GAC CTG TGG CAA AAG AGG CAG AAG CAA GTA AAA G  4122
Met Tyr Leu Leu Lys Asp Leu Trp Gln Lys Arg Gln Lys Gln Val Lys
         150             155             160
```

| | |
|---|---|
| GTAGATATCC TTGTGCTTTC CATTCGATTT TCAGCTATAA AATTGGAACC GTTAGACTGC | 4182 |
| CACGAGAATG CATGGTTGTG AGAAGATTAA CATTTCTGGG TTAGTGAATA GCATTCATAC | 4242 |
| GCTTTTGGGC ACCTTCCCCT GCAACTTGCC AGATAAGCAC TATTCAGCTC TTATTCCCAG | 4302 |
| TCTGACATCA GCAAGTGTGA TTTTCTATGA AAAATTCTAC TATGACTCCT TATTTAAGT | 4362 |
| ATACAAGAAA CTTGTGACTC AGAAGATAAT ATTTACAGAG TGGAAAAAAA CCCCTAGCAT | 4422 |
| TTATAGTTTT AACATTTGAG GTTTTGAATG AGAGAGTTAT CCATAATATA TTCAATTGTG | 4482 |
| TTGTGGATAA TGACACCTAA CCTGTGAATC TTGAGGTCAG AATGTTGAGT GCTGTTGACT | 4542 |
| TGGTGGTCAG GAAACAGCTA GTGCGTGAGC CTGGCACAGG CATCTCAGTG AGTAGCATAC | 4602 |
| CCACAGTTGG AAATTTTTCA AAGAAATCAA AGGAATCATG ACATCTTATA AATTTCAAGG | 4662 |
| TTCTGCTATA CTTATGTGAA ATGGATAAAT AAATCAAGCA TATCCACTCT GTAAGATTGA | 4722 |
| ACTTCTCAGA TGGAAGACCC CAATACTGCT TTCTCCTCTT TTCCCTCACC AAAGAAATAA | 4782 |
| ACAACCTATT TCATTTATTA CTGGACACAA TCTTTAGCGT ATACCTATGG TAAATTACTA | 4842 |

-continued

```
GTATGGTGGT TAGGATTTAT GTTAATTTGT ATATGTCATG CGCCAAATCA TTTCCACTAA        4902

ATATGACTAT ATATCATAAC TGCTTGGTGA TAGCTCAGTG TTTAATAGTT TATTCTCAGA        4962

AAATCAAAAT TGTATAGTTA AATACATTAG TTTTATGAGG CAAAAATGCT AACTATTTCT        5022

ACATAATTTC ATTTTTCCAG  AT AAT GAA AAT GTA GTC AAT GAG TAC TCC            5071
                       Asp Asn Glu Asn Val Val Asn Glu Tyr Ser
                           165                 170

TCA GAA CTG GAA AAG CAC CAA TTA TAT ATA GAT GAG ACT GTG AAT AGC          5119
Ser Glu Leu Glu Lys His Gln Leu Tyr Ile Asp Glu Thr Val Asn Ser
        175             180                 185

AAT ATC CCA ACT AAC CTT CGT GTG CTT CGT TCA ATC CTG GAA AAC CTG          5167
Asn Ile Pro Thr Asn Leu Arg Val Leu Arg Ser Ile Leu Glu Asn Leu
190             195                 200                 205

AGA AGC AAA ATA CAA AAG TTA GAA TCT GAT GTC TCA GCT CAA ATG GAA          5215
Arg Ser Lys Ile Gln Lys Leu Glu Ser Asp Val Ser Ala Gln Met Glu
                210                 215                 220

TAT TGT CGC ACC CCA TGC ACT GTC AGT TGC AAT ATT CCT GTG GTG TCT          5263
Tyr Cys Arg Thr Pro Cys Thr Val Ser Cys Asn Ile Pro Val Val Ser
                225                 230                 235

GGC AAA  G GTAACTGATT CATAAACATA TTTTTAGAGA GTTCCAGAAG AACTCACACA        5320
Gly Lys
CCAAAAATAA GAGAACAACA ACAACAACAA AAATGCTAAG TGGATTTTCC CAACAGATCA       5380

TAATGACATT ACAGTACATC ATAAAATAT  CCTTAGCCAG TTGTGTTTTG GACTGGCCTG        5440

GTGCATTTGC TGGTTTTGAT GAGCAGGATG GGCACAGGT  AGTCCCAGGG GTGGCTGATG        5500

TGTGCATCTG CGTACTGGCT TGAACAGATG GCAGAACCAC AGATAGATGT AGAAGTTTCT        5560

CCATTTGTG  TGTTCTGGGA GCTCATGGAT ATTCCAGGAC ACAAAGGTG  GAGAAGAGCT        5620

TTGTTCATCC TCTTAGCAGA TAAACGTCCT CAAAACTGGG TTGGACTTAC TAAAGTAAAA        5680

TGAAAATCTA ATATTTGTTA TATTATTTTC AAAGGTCTAT AATAACACAC TCCTTAGTAA        5740

CTTATGTAAT GTTATTTAA  AGAATTGGTG ACTAAATACA AAGTAATTAT GTCATAAACC        5800

CCTGAACATA ATGTTGTCTT ACATTTGCAG  AA TGT GAG GAA ATT ATC AGG AAA        5853
                                  Glu Cys Glu Glu Ile Ile Arg Lys
                                                  240             245

GGA GGT GAA ACA TCT GAA ATG TAT CTC ATT CAA CCT GAC AGT TCT GTC          5901
Gly Gly Glu Thr Ser Glu Met Tyr Leu Ile Gln Pro Asp Ser Ser Val
        250                 255                 260

AAA CCG TAT AGA GTA TAC TGT GAC ATG AAT ACA GAA AAT GGA       G          5944
Lys Pro Tyr Arg Val Tyr Cys Asp Met Asn Thr Glu Asn Gly
                265                 270             275

GTAAGCTTTC GACAGTTGTT GACCTGTTGA TCTGTAATTA TTTGGATACC GTAAAATGCC        6004

AGGAAACAAG GCCAGGTGTG GTGGCTCATA CCTGTAATTC CAGCACCTTG GGAGGCCAAA        6064

GTGGGCTGAT AGCTTGAGCC TAGGAGTTTG AAACTAGCCT GGGCAACATA ATGAGACCCT        6124

AACTCTACAA AAAAAAAAA  AATACCAAAA AAAAAAAAA  AATCAGCTGT GTTGGTAGTA        6184

TGTGCCTGTA GTCCCAGCTA TCCAGGAGGC TGAGATGGGA GATCACCTGA GCCCACAACC        6244

TGGAGTCTTG ATCATGCTAC TGAACTGTAG CCTGGGCAAC AGAGGATAGT GAGATCCTGT        6304

CTCAAAAAAA AAAATTAATT AAAAGCCAG  GAAACAAGAC TTAGCTCTAA CATCTAACAT        6364

AGCTGACAAA GGAGTAATTT GATGTGGAAT TCAACCTGAT ATTTAAAGT  TATAAAATAT        6424

CTATAATTCA CAATTTGGGG TAAGATAAAG CACTTGCAGT TTCCAAAGAT TTACAAGTT         6484

TACCTCTCAT ATTTATTTCC TTATTGTGTC TATTTTAGAG CACCAAATAT ATACTAAATG        6544

GAATGGACAG GGGATTCAGA TATTATTTTC AAAGTGACAT TATTTGCTGT TGGTTAATAT        6604
```

```
ATGCTCTTTT TGTTTCTGTC AACCAAAG GA TGG ACA GTG ATT CAG AAC CGT              6655
                                   Gly Trp Thr Val Ile Gln Asn Arg
                                       280                     285

CAA GAC GGT AGT GTT GAC TTT GGC AGG AAA TGG GAT CCA TAT AAA CAG            6703
Gln Asp Gly Ser Val Asp Phe Gly Arg Lys Trp Asp Pro Tyr Lys Gln
                290                 295                 300

GGA TTT GGA AAT GTT GCA ACC AAC ACA GAT GGG AAG AAT TAC TGT GGC            6751
Gly Phe Gly Asn Val Ala Thr Asn Thr Asp Gly Lys Asn Tyr Cys Gly
            305                 310                 315

CTA CCA  G GTAACGAACA GGCATGCAAA ATAAATCAT TCTATTTGAA ATGGATTTT            6808
Leu Pro
TTTTAATTAA AAAACATTCA TTGTTGGAAG CCTGTTTTAG GCAGTTAAGA GGAGTTTCCT          6868

GACAAAAATG TGGAAGCTAA AGATAAGGGA AGAAAGGCAG TTTTAGTTT CCCAAAATTT           6928

TATTTTTGGT GAGAGATTTT ATTTGTTTT TCTTTTAG GT GAA TAT TGG CTT                6980
                                             Gly Glu Tyr Trp Leu
                                                          320

GGA AAT GAT AAA ATT AGC CAG CTT ACC AGG ATG GGA CCC ACA GAA CTT            7028
Gly Asn Asp Lys Ile Ser Gln Leu Thr Arg Met Gly Pro Thr Glu Leu
325             330                 335                 340

TTG ATA GAA ATG GAG GAC TGG AAA GGA GAC AAA GTA AAG GCT CAC TAT            7076
Leu Ile Glu Met Glu Asp Trp Lys Gly Asp Lys Val Lys Ala His Tyr
                345                 350                 355

GGA GGA TTC ACT GTA CAG AAT GAA GCC AAC AAA TAC CAG ATC TCA GTG            7124
Gly Gly Phe Thr Val Gln Asn Glu Ala Asn Lys Tyr Gln Ile Ser Val
            360                 365                 370

AAC AAA TAC AGA GGA ACA GCC GGT AAT GCC CTC ATG GAT GGA GCA TCT            7172
Asn Lys Tyr Arg Gly Thr Ala Gly Asn Ala Leu Met Asp Gly Ala Ser
        375                 380                 385

CAG CTG ATG GGA GAA AAC AGG ACC ATG ACC ATT CAC AAC GGC ATG TTC            7220
Gln Leu Met Gly Glu Asn Arg Thr Met Thr Ile His Asn Gly Met Phe
    390                 395                 400

TTC AGC ACG TAT GAC AGA GAC AAT GAC GGC TG GTATGTGTGG                      7262
Phe Ser Thr Tyr Asp Arg Asp Asn Asp Gly Trp
405                 410                 415

CACTCTTTGC TCCTGCTTTA AAAATCACAC TAATATCATT ACTCAGAATC ATTAACAATA          7322

TTTTTAATAG CTACCACTTC CTGGGCACTT ACTGTCAGCC ACTGTCCTAA GCTCTTATG           7382

CATCACTCGA AAGCATTTCA ACTATAAGGT AGACATTCTT ATTCTCATTT TACAGATGAG          7442

ATTAGAGAG ATTACGTGAT TTGTCCAATG TCACACAACT ACCCAGAGAT AAAACTAGAA           7502

TTTGAGCACA GTTACTTTCT GAATAATGAG CATTAGATA AATACCTATA TCTCTATATT           7562

CTAAAGTGTG TGTGAAAACT TTCATTTTCA TTTCCAGGGT CTCTGATAC TAAGGGTTGT           7622

AAAAGCTATT ATTCCAGTAT AAAGTAACAA ACACAGTCCC TAGATGGATT GCCACAAGG           7682

CCCAGTTATC TCTCTTTCTT GCTATAGGGC ACAGGAGGTC TTTGGTGTAT TAGTGTGACT          7742

CTATGTATAG CACCCAAAGG AAAGACTACT GTGCACACGA GTGTAGCAGT CTTTTATGGG          7802

TAATCTGCAA AACGTAACTT GACCACCGTA GTTCTGTTTC TAATAACGCC AAACACATTT         7862

TCTTTCAG G TTA ACA TCA GAT CCC AGA AAA CAG TGT TCT AAA GAA GAC             7910
           Leu Thr Ser Asp Pro Arg Lys Gln Cys Ser Lys Glu Asp
                       420                 425

GGT GGT GGA TGG TGG TAT AAT AGA TGT CAT GCA GCC AAT CCA AAC GGC            7958
Gly Gly Gly Trp Trp Tyr Asn Arg Cys His Ala Ala Asn Pro Asn Gly
430                 435                 440

AGA TAC TAC TGG GGT GGA CAG TAC ACC TGG GAC ATG GCA AAG CAT GGC            8006
Arg Tyr Tyr Trp Gly Gly Gln Tyr Thr Trp Asp Met Ala Lys His Gly
```

```
                    445                  450                     455                      460
ACA GAT GAT GGT GTA GTA TGG ATG AAT TGG AAG GGG TCA TGG TAC TCA                             8054
Thr Asp Asp Gly Val Val Trp Met Asn Trp Lys Gly Ser Trp Tyr Ser
                465                     470                     475

ATG AGG AAG ATG AGT ATG AAG ATC AGG CCC TTC TTC CCA CAG CAA TAGTCCCC                        8109
Met Arg Lys Met Ser Met Lys Ile Arg Pro Phe Phe Pro Gln Gln
                480                     485                     490

TACGTAGATT TTTGCTCTTC TGTATGTGAC AACATTTTG TACATTATGT TATTGGAATT                            8169
TTCTTTCATA CATTATATTC CTCTAAAACT CTCAAGCAGA CGTGAGTGTG ACTTTTGAA                             8229
AAAAGTATAG GATAAATTAC ATTAAATAG CACATGATTT TCTTTGTTT TCTTCATTTC                              8289
TCTTGCTCAC CCAAGAAGTA ACAAAGTAT AGTTTGACA GAGTTGGTGT TCATAATTTC                              8349
AGTTCTAGTT GATTGCGAGA ATTTTCAAAT AAGGAAGAGG GGTCTTTAT CCTTGTCGTA                             8409
GGAAAACCAT GACGGAAAGG AAAAACTGAT GTTTAAAAGT CCACTTTTAA AACTATATTT                            8469
ATTTATGTAG GATCTGTCAA AGAAAACTTC CAAAAAGATT TATTAATTAA ACCAGACTCT                            8529
GTTGCAATAA GTTAATGTTT TCTTGTTTTG TAATCCACAC ATTCAATGAG TTAGGCTTTG                            8589
CACTTGTAAG GAAGGAGAAG CGTTCACAAC CTCAAATAGC TAATAAACCG GTCTTGAATA                            8649
TTTGAAGATT TAAAATCTGA CTCTAGGACG GGCACGGTGG CTCACGACTA TAATCCCAAC                            8709
ACTTTGGGAG GCTGAGGCGG GCGGTCACAA GGTCAGGAGT TCAAGACCAG CCTGACCAAT                            8769
ATGGTGAAAC CCCATCTCTA CTAAAATAC AAAAATTAGC CAGGCGTGGT GGCAGGTGCC                             8829
TGTAGGTCCC AGCTAGCCTG TGAGGTGGAG ATTGCATTGA GCCAAGATC                                        8878
```

( 2 ) INFORMATION FOR SEQ ID NO:4:

( i ) SEQUENCE CHARACTERISTICS:
    ( A ) LENGTH: 491 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Met Lys Arg Met Val Ser Trp Ser Phe His Lys Leu Lys Thr Met Lys
 1               5                  10                  15

His Leu Leu Leu Leu Leu Leu Cys Val Phe Leu Val Lys Ser Gln Gly
                20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
        50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175
```

| | | | | | | | | | | | | | | |
|---|---|---|---|---|---|---|---|---|---|---|---|---|---|---|
|Glu|Lys|His|Gln|Leu|Tyr|Ile|Asp|Glu|Thr|Val|Asn|Ser|Asn|Ile|Pro|
| | | |180| | | |185| | | |190| | |
|Thr|Asn|Leu|Arg|Val|Leu|Arg|Ser|Ile|Leu|Glu|Asn|Leu|Arg|Ser|Lys|
| | |195| | | |200| | | |205| | | |
|Ile|Gln|Lys|Leu|Glu|Ser|Asp|Val|Ser|Ala|Gln|Met|Glu|Tyr|Cys|Arg|
| |210| | | |215| | | |220| | | |
|Thr|Pro|Cys|Thr|Val|Ser|Cys|Asn|Ile|Pro|Val|Val|Ser|Gly|Lys|Glu|
|225| | | |230| | | |235| | | |240|
|Cys|Glu|Glu|Ile|Ile|Arg|Lys|Gly|Glu|Thr|Ser|Glu|Met|Tyr|Leu|
| | | |245| | | |250| | | |255|
|Ile|Gln|Pro|Asp|Ser|Ser|Val|Lys|Pro|Tyr|Arg|Val|Tyr|Cys|Asp|Met|
| | |260| | | |265| | | |270|
|Asn|Thr|Glu|Asn|Gly|Gly|Trp|Thr|Val|Ile|Gln|Asn|Arg|Gln|Asp|Gly|
| |275| | | |280| | | |285|
|Ser|Val|Asp|Phe|Gly|Arg|Lys|Trp|Asp|Pro|Tyr|Lys|Gln|Gly|Phe|Gly|
| |290| | | |295| | | |300|
|Asn|Val|Ala|Thr|Asn|Thr|Asp|Gly|Lys|Asn|Tyr|Cys|Gly|Leu|Pro|Gly|
|305| | | |310| | | |315| | | |320|
|Glu|Tyr|Trp|Leu|Gly|Asn|Asp|Lys|Ile|Ser|Gln|Leu|Thr|Arg|Met|Gly|
| | | |325| | | |330| | | |335|
|Pro|Thr|Glu|Leu|Leu|Ile|Glu|Met|Glu|Asp|Trp|Lys|Gly|Asp|Lys|Val|
| | |340| | | |345| | | |350|
|Lys|Ala|His|Tyr|Gly|Gly|Phe|Thr|Val|Gln|Asn|Glu|Ala|Asn|Lys|Tyr|
| | |355| | | |360| | | |365|
|Gln|Ile|Ser|Val|Asn|Lys|Tyr|Arg|Gly|Thr|Ala|Gly|Asn|Ala|Leu|Met|
| |370| | | |375| | | |380|
|Asp|Gly|Ala|Ser|Gln|Leu|Met|Gly|Glu|Asn|Arg|Thr|Met|Thr|Ile|His|
|385| | | |390| | | |395| | | |400|
|Asn|Gly|Met|Phe|Phe|Ser|Thr|Tyr|Asp|Arg|Asp|Asn|Asp|Gly|Trp|Leu|
| | | |405| | | |410| | | |415|
|Thr|Ser|Asp|Pro|Arg|Lys|Gln|Cys|Ser|Lys|Glu|Asp|Gly|Gly|Gly|Trp|
| | |420| | | |425| | | |430|
|Trp|Tyr|Asn|Arg|Cys|His|Ala|Ala|Asn|Pro|Asn|Gly|Arg|Tyr|Tyr|Trp|
| |435| | | |440| | | |445|
|Gly|Gly|Gln|Tyr|Thr|Trp|Asp|Met|Ala|Lys|His|Gly|Thr|Asp|Asp|Gly|
|450| | | |455| | | |460|
|Val|Val|Trp|Met|Asn|Trp|Lys|Gly|Ser|Trp|Tyr|Ser|Met|Arg|Lys|Met|
|465| | | |470| | | |475| | | |480|
|Ser|Met|Lys|Ile|Arg|Pro|Phe|Phe|Pro|Gln|Gln|
| | | |485| | | |490|

( 2 ) INFORMATION FOR SEQ ID NO:5:

( i ) SEQUENCE CHARACTERISTICS:
     ( A ) LENGTH: 10564 base pairs
     ( B ) TYPE: nucleic acid
     ( C ) STRANDEDNESS: double
     ( D ) TOPOLOGY: linear ( i i ) MOLECULE TYPE: DNA (genomic)

( v i i ) IMMEDIATE SOURCE:
     ( B ) CLONE: human fibrinogen gamma chain ( i x ) FEATURE:
     ( A ) NAME/KEY: CDS
     ( B ) LOCATION: join(1799..1876, 1973..2017, 2207..2390, 2510
         . . 2603, 4211..4341, 4645..4778, 5758..5942, 7426
         . . 7703, 9342..9571)

( x i ) SEQUENCE DESCRIPTION: SEQ ID NO:5:

| | | | | | |
|---|---|---|---|---|---|
| CTACACACTT | CTTGAAGGCA | AAGGCAATGC | TGAAGTCACC | TTTCATGTTC | AAATCATATT | 60 |
| AAAAAGTTAG | CAAGATGTAA | TTATCAGTGT | ACTATGTAAA | TCTTTGTGAA | TGATCAATAA | 120 |
| TTACATATTT | TCATTATATA | TATTTAGTA | GATAATATTT | ATATACATTC | AACATTCTAA | 180 |
| ATATAGAAAG | TTTACAGAGA | AAAATAAAGC | CTTTTTTTCC | AATCCTGTCC | TCCACCTCTG | 240 |
| CATCCCATTC | TTCTTCACAG | AGGCAACTGA | TTCAAGTCAT | TACATAGTTA | TTGAGTGTTA | 300 |
| ACTACAACTA | TGTTAAGTAC | AGCTATATAT | GTTAGATGCC | GTAGCCACAG | AAATCAGTTT | 360 |
| ACAATCTAAT | GCAGTGGATA | CAGCATGTAT | ACATATAATA | TAAGGTTGCT | ACAAATGCTA | 420 |
| TCTGAGGTAG | AGCTGTTTGA | AAGAATACTA | ATACTTAAAT | GTTTAATTCA | ACTGACTTGA | 480 |
| TTGACAACTG | ATTAGCTGAG | TGGAAAAGAT | GGATGAGAAA | GATTGTGAGA | CTTAATTGGC | 540 |
| TGGTGGTATG | GTGATATGAT | TGACAATAAC | TGCTAAGTCA | GAGAGGGATA | TATTAAGGAG | 600 |
| GAGAAGAAAA | GCAACAAATC | TGGTTTTGAT | GTGTTCACTT | TGTTATAATT | ATTGATTATT | 660 |
| TACTGAATAT | GAATATTTAT | CTTTGTTTTT | GAGTCAATAA | ATATACCTTT | GTAAAGACAG | 720 |
| AATTAAAGTA | TTAGTATTTC | TTTCAAACTG | GAGGCATTTC | TCCCACTAAC | ATATTTCATC | 780 |
| AAAACTTATA | ATAAGCTTGG | TTCCAGAGGA | AGAAATGAGG | GATAACCAAA | AATAGAGACA | 840 |
| TTAATAATAG | TGTAACGCCC | AGTGATAAAT | CTCAATAGGC | AGTGATGACA | GACATGTTTT | 900 |
| CCCAAACACA | AGGATGCTGT | AAGGGCCAAA | CAGAAATGAT | GGCCCCTCCC | CAGCACCTCA | 960 |
| TTTTGCCCCT | TCCTTCAGCT | ATGCCTCTAC | TCTCCTTTAG | ATACAAGGGA | GGTGGATTTT | 1020 |
| TCTCTTCTCT | GAGATAGCTT | GATGGAACCA | CAGGAACAAT | GAAGTGGGCT | CCTGGCTCTT | 1080 |
| TTCTCTGTGG | CAGATGGGGT | GCCATGCCCA | CCTTCAGACA | AAGGGAAGAT | TGAGCTCAAA | 1140 |
| AGCTCCCTGA | GAAGTGAGAG | CCTATGAACA | TGGTTGACAC | AGAGGGACAG | GAATGTATTT | 1200 |
| CCAGGGTCAT | TCATTCCTGG | GAATAGTGAA | CTGGGACATG | GGGGAAGTCA | GTCTCCTCCT | 1260 |
| GCCACAGCCA | CAGATTAAAA | ATAATAATGT | TAACTGATCC | CTAGGCTAAA | ATAATAGTGT | 1320 |
| TAACTGATCC | CTAAGCTAAG | AAAGTTCTTT | TGGTAATTCA | GGTGATGGCA | GCAGGACCCA | 1380 |
| TCTTAAGGAT | AGACTAGGTT | TGCTTAGTTC | GAGGTCATAT | CTGTTTGCTC | TCAGCCATGT | 1440 |
| ACTGGAAGAA | GTTGCATCAC | ACAGCCTCCA | GGACTGCCCT | CCTCCTCACA | GCAATGGATA | 1500 |
| ATGCTTCACT | AGCCTTTGCA | GATAATTTTG | GATCAGAGAA | AAAACCTTGA | GCTGGGCCAA | 1560 |
| AAAGGAGGAG | CTTCAACCTG | TGTGCAAAAT | CTGGGAACCT | GACAGTATAG | GTTGGGGGCC | 1620 |
| AGGATGAGGA | AAAAGGAACG | GGAAAGACCT | GCCCACCCTT | CTGGTAAGGA | GGCCCCGTGA | 1680 |
| TCAGCTCCAG | CCATTTGCAG | TCCTGGCTAT | CCCAGGAGCT | ACATAAAGG | GACAATTGGA | 1740 |
| GCCTGAGAGG | TGACAGTGCT | GACACTACAA | GGCTCGGAGC | TCCGGGCACT | CAGACATC | 1798 |

| | | | | | | | | | | | | | | | | |
|---|---|---|---|---|---|---|---|---|---|---|---|---|---|---|---|---|
| ATG | AGT | TGG | TCC | TTG | CAC | CCC | CGG | AAT | TTA | ATT | CTC | TAC | TTC | TAT | GCT | 1846 |
| Met | Ser | Trp | Ser | Leu | His | Pro | Arg | Asn | Leu | Ile | Leu | Tyr | Phe | Tyr | Ala | |
| 1 | | | | 5 | | | | | 10 | | | | | 15 | | |

| | | | | | | | | |
|---|---|---|---|---|---|---|---|---|
| CTT | TTA | TTT | CTC | TCT | TCA | ACA | TGT | GTA | GCA | GTAAGTGTGC TCTTCACAAA | 1896 |
| Leu | Leu | Phe | Leu | Ser | Ser | Thr | Cys | Val | Ala | | |
| | | 20 | | | | | 25 | | | | |

ACGTTGTTTA AAATGGAAAG CTGGAAAATA AAACAGATAA TAAACTAGTG AAATTTTCGT 1956

| | | | | | | | | | | |
|---|---|---|---|---|---|---|---|---|---|---|
| ATTTTTCTC TTTTAG | TAT | GTT | GCT | ACC | AGA | GAC | AAC | TGC | TGC | ATC | TTA | 2005 |
| | Tyr | Val | Ala | Thr | Arg | Asp | Asn | Cys | Cys | Ile | Leu |
| | | 30 | | | | | | 35 | | | |

| | | | | | |
|---|---|---|---|---|---|
| GAT | GAA | AGA | TTC | GTAAGTAGTT TTTATGTTTC TCCCTTTGTG TGTGAACTGG | 2057 |
| Asp | Glu | Arg | Phe | | |

```
                    40
AGAGGGGCAG AGGAATAGAA ATAATTCCCT CATAAATATC ATCTGGCACT TGTAACTTTT      2117

TAAAAACATA GTCTAGGTTT TACCTATTTT TCTTAATAGA TTTAAGAGT AGCATCTGTC       2177

TACATTTTTA ATCACTGTTA TATTTTCAG GGT AGT TAT TGT CCA ACT ACC TGT        2230
                                Gly Ser Tyr Cys Pro Thr Thr Cys
                                             45

GGC ATT GCA GAT TTC CTG TCT ACT TAT CAA ACC AAA GTA GAC AAG GAT        2278
Gly Ile Ala Asp Phe Leu Ser Thr Tyr Gln Thr Lys Val Asp Lys Asp
 50              55              60                          65

CTA CAG TCT TTG GAA GAC ATC TTA CAT CAA GTT GAA AAC AAA ACA TCA        2326
Leu Gln Ser Leu Glu Asp Ile Leu His Gln Val Glu Asn Lys Thr Ser
             70              75                          80

GAA GTC AAA CAG CTG ATA AAA GCA ATC CAA CTC ACT TAT AAT CCT GAT        2374
Glu Val Lys Gln Leu Ile Lys Ala Ile Gln Leu Thr Tyr Asn Pro Asp
         85              90                          95

GAA TCA TCA AAA CCA  A GTGAGAAAAT AAAGACTACT GACCAAAAAA                2420
Glu Ser Ser Lys Pro
             100

TAATAATAAT AATCTGTGAA GTTCTTTTGC TGTTGTTTTA GTTGTTCTAT TTGCTTAAGG      2480

ATTTTTATGT CTCTGATCCT ATATTACAG AT ATG ATA GAC GCT GCT ACT TTG        2532
                                  Asn Met Ile Asp Ala Ala Thr Leu
                                      105                     110

AAG TCC AGG ATA ATG TTA GAA GAA ATT ATG AAA TAT GAA GCA TCG ATT        2580
Lys Ser Arg Ile Met Leu Glu Glu Ile Met Lys Tyr Glu Ala Ser Ile
             115             120                         125

TTA ACA CAT GAC TCA AGT ATT  CG GTAAGGATTT TTGTTTAAT TTGCTCTGCA       2633
Leu Thr His Asp Ser Ser Ile  Arg
                 130

AGACTGATTT AGTTTTTATT TAATATTCTA TACTTGAGTG AAAGTAATTT TTAATGTGTT      2693

TTCCCCATTT ATAATATCCC AGTGACATTA TGCCTGATTA TGTTGAGCAT AGTAGAGATA     2753

GAAGTTTTTA GTGCAATATA AATTATACTG GGTTATAATT GCTTATTAAT AATCACATTG     2813

AAGAAAGATG TTCTAGATGT CTTCAAATGC TAGTTTGACC ATATTTATCA AAAATTTTTT     2873

CCCCATCCCC CATTTATCTT ACAACATAAA ATCAATCTCA TAGGAATTTG GGTGTTGAAA     2933

ATAAAATCCT CTTTATAAAA ATGCTGACAA ATTGGTGGTT AAAAAAATTA GCAAGCAGAG     2993

GCATAGTAAG GATTTTGGCT CCTAAAGTAA ATTATATTGA ATGTGGAGCA GGAAGAAACA     3053

TGTCTTGAGA GACTAAGTGT GGCAAATATT GCAAAGCTCA TATTGATCAT GCAGAATGA      3113

ACCTGCATAG TCTCTTCCCT TCATTTGGAA GTGAATGTCT CTGTTAAAGC TTCTCAGGGA     3173

CTCATAAACT TTCTGAACAT AAGGTCTCAG ATACAGTTTT AATATTTTC CCCAATTTTT      3233

TTTTCTGAAT TTTTCTCAAA GCAGCTTGAG AAATTGAGAT AAATAGTAGC TAGGGAGAAG     3293

TGGCCCAGGA AAGATTTCTC CTCTTTTTGC TATCAGAGGG CCCTTGTTAT TATTGTTATT     3353

ATTATTACTT GCATTATTAT TGTCCATCAT TGAAGTTGAA GGAGGTTATT GTACAGAAAT     3413

TGCCTAAGAC AAGGTAGAGG GAAAACGTGG ACAAATAGTT TGTCTACCCT TTTTTACTTC     3473

AAAGAAAGAA CGGTTTATGC ATTGTAGACA GTTTTCTATC ATTTTGGAT ATTTGCAAGC      3533

CACCCTGTAA GTAACTACAA AAGGAGGGTT TTTACTTCCC CCAGTCCATT CCCAAAGCTA     3593

TGTAACCAGA AGCATTAAAG AAGAAGGGG AAGTATCTGT TGTTTATTT TACATACAAT       3653

AACGTTCCAG ATCATGTCCC TGTGTAAGTT ATATTTTAGA TTGAAGCTTA TATGTATAGC     3713

CTCAGTAGAT CCACAAGTGA AAGGTATACT CCTTCAGCAC ATGTGAATTA CTGAACTGAG     3773
```

```
CTTTTCCTGC TTCTAAAGCA TCAGGGGGTG TTCCTATTAA CCAGTCTCGC CACTCTTGCA    3833

GGTTGCTATC TGCTGTCCCT TATGCATAAA GTAAAAAGCA AAATGTCAAT GACATTTGCT    3893

TATTGACAAG GACTTTGTTA TTTGTGTTGG GAGTTGAGAC AATATGCCCC ATTCTAAGTA    3953

AAAAGATTCA GGTCCACATT GTATTCCTGT TTTAATTGAT TTTTGATTT  GTTTTCTTT     4013

TTCAAAAAGT TTATAATTTT AATTCATGTT AATTTAGTAA TATAATTTTA CATTTCCTC     4073

AAGAATGGAA TAATTTATCA GAAAGCACTT CTTAAGAAAA TACTTAGCAG TTCCAAAGA     4133

AAATATAAAA TTACTCTTCT GAAAGGAATA CTTATTTTTG TCTTCTTATT TTTGTTATCT    4193

TATGTTTCTG TTTGTAG A TAT TTG CAG GAA ATA TAT AAT TCA AAT AAT CAA    4244
                    Tyr Leu Gln Glu Ile Tyr Asn Ser Asn Asn Gln
                        135             140                 145

AAG ATT GTT AAC CTG AAA GAG AAG GTA GCC CAG CTT GAA GCA CAG TGC     4292
Lys Ile Val Asn Leu Lys Glu Lys Val Ala Gln Leu Glu Ala Gln Cys
            150             155                 160

CAG GAA CCT TGC AAA GAC ACG GTG CAA ATC CAT GAT ATC ACT GGG AAA G   4341
Gln Glu Pro Cys Lys Asp Thr Val Gln Ile His Asp Ile Thr Gly Lys
            165             170                 175

GTAACTGATG AAGGTTATAT TGGGATTAGG TTCATCAAAG TAAGTAATGT AAAGGAGAAA    4401

GTATGTACTG GAAAGTATAG GAATAGTTTA GAAAGTGGCT ACCCATTAAG TCTAAGAATT    4461

TCAGTTGTCT AGACCTTTCT TGAATAGCTA AAAAAAACAG TTTAAAAGGA ATGCTGATGT    4521

GAAAAGTAAG AAAATTATTC TTGGAAAATG AATAGTTTAC TACATGTTAA AAGCTATTTT    4581

TCAAGGCTGG CACAGTCTTA CCTGCATTTC AAACCACAGT AAAAGTCGAT CTCCTTCTC    4641

TAG  AT TGT CAA GAC ATT GCC AAT AAG GGA GCT AAA CAG AGC GGG CTT     4688
        Asp Cys Gln Asp Ile Ala Asn Lys Gly Ala Lys Gln Ser Gly Leu
            180             185                 190

TAC TTT ATT AAA CCT CTG AAA GCT AAC CAG CAA TTC TTA GTC TAC TGT     4736
Tyr Phe Ile Lys Pro Leu Lys Ala Asn Gln Gln Phe Leu Val Tyr Cys
            195             200                 205

GAA ATC GAT GGG TCT GGA AAT GGA TGG ACT GTG TTT CAG AAG              4778
Glu Ile Asp Gly Ser Gly Asn Gly Trp Thr Val Phe Gln Lys
            210             215                 220

GTAATTTTTT CCCCACCATG TGTATTTAAT AAATTCCTAC ATTGTTTCTG CCATATGGCA    4838

GATACTTTTC TAAGCACCTT GTGAACCGTA GCTCATTTAA TCCTTGCAAT AGCCCTAAGA    4898

GGAAGGTACT TCTGTTACTC CTATTTACAG AAAAGGAAAC TGAGGCACAC AAGGTTAAAT    4958

AACTTGCCCA AGACCACATA ACTAATAAGC AACAGAGTCA GCATTTGAAC CTAGGCAGTA    5018

TAGTTTCAGA GTTTGTGACT TGACTCTATA TTGTACTGGC ACTGACTTTG TAGATTCATG    5078

GTGGCACATA ATCATAGTAC CACAGTGACA AATAAAAGA  AGGAAACTCT TTGTCAGGT     5138

AGGTCAAGAC CTGAGGTTTC CCATCACAAG ATGAGGAAGC CCAACACCAC CCCCACCAC    5198

CCCACCACCA TCACCACCCT TTCACACACC AGAGGATACA CTTGGGCTGC TCCAAGACAA    5258

GGAACCTGTG TTGCATCTGC CACTTGCTGA TACCCACTAG GAATCTTGGC TCCTTTACTT    5318

TCTGTTTACC TCCCACCACT GTTATAACTG TTCTACAGG  GGGCGCTCAG AGGGAATGAA    5378

TGGTGGAAGC ATTAGTTGCC AGACACCGAT TGAGCAATGG GTTCCATCAT AAGTGTAAGA    5438

ATCAGTAATA TCCAGCTAGA GTTCTGAAGT CGTCTAGGTG TCTTTTTAAT ATTACCACTC    5498

ATTTAGAATT TATGATGTGC CAGAAACCCT CTTAAGTATT TCTCTTATAT TCTCTCTCAT    5558

GATCCTTGCA GCAACCCTAA GAAGTAACCA TCATTTTTCC TATTTGATAC ATGAGGAAAC    5618

TGAGGTAGCT TGGCCAAGAT CACTTAGTTG GGAGTTGATA GAACCAGTGC CTGTATTTT    5678

TGACAAAATG TTGACAGCAT TCTCTTTACA TGCATTGATA GTCTATTTTC TCCTTTTGCT    5738
```

-continued

| | | | | | | | | | | |
|---|---|---|---|---|---|---|---|---|---|---|
| CTTGCAAATG | TGTAATTAG | AGA | CTT | GAT | GGC | AGT | GTA | GAT | TTC AAG AAA AAC | 5790 |
| | | Arg | Leu | Asp | Gly | Ser | Val | Asp | Phe Lys Lys Asn | |
| | | | 225 | | | | | | 230 | |

| | | | | | | | | | | | | | | | |
|---|---|---|---|---|---|---|---|---|---|---|---|---|---|---|---|
| TGG | ATT | CAA | TAT | AAA | GAA | GGA | TTT | GGA | CAT | CTG | TCT | CCT | ACT | GGC ACA | 5838 |
| Trp | Ile | Gln | Tyr | Lys | Glu | Gly | Phe | Gly | His | Leu | Ser | Pro | Thr | Gly Thr | |
| | 235 | | | | 240 | | | | | 245 | | | | | |

| ACA | GAA | TTT | TGG | CTG | GGA | AAT | GAG | AAG | ATT | CAT | TTG | ATA | AGC | ACA CAG | 5886 |
|---|---|---|---|---|---|---|---|---|---|---|---|---|---|---|---|
| Thr | Glu | Phe | Trp | Leu | Gly | Asn | Glu | Lys | Ile | His | Leu | Ile | Ser | Thr Gln | |
| 250 | | | | | 255 | | | | | 260 | | | | 265 | |

| TCT | GCC | ATC | CCA | TAT | GCA | TTA | AGA | GTG | GAA | CTG | GAA | GAC | TGG | AAT GGC | 5934 |
|---|---|---|---|---|---|---|---|---|---|---|---|---|---|---|---|
| Ser | Ala | Ile | Pro | Tyr | Ala | Leu | Arg | Val | Glu | Leu | Glu | Asp | Trp | Asn Gly | |
| | | | | 270 | | | | | 275 | | | | | 280 | |

| AGA | ACC | AG | GTACTGTTTT | GAAATGACTT | CCAACTTTTT | ATTGTAAAGA | 5982 |
|---|---|---|---|---|---|---|---|
| Arg | Thr | Ser | | | | | |

| | | | | |
|---|---|---|---|---|
| TTGCCTGGAA | TGTGCACTTT | CCAACTATCA | ATAGACAATG GCAAATGCAG | CCTGACAAAT | 6042 |
| GCAAACAGCA | CATCCAGCCA | CCATTTTCTC | CAGGAGTCTG | TTTGGTTCTT GGGCAATCCA | 6102 |
| AAAAGGTAAA | TTCTATTCAG | GATGAATCTA | AGTGTATTGG | TACAATCTAA TTACCCTGGA | 6162 |
| ACCATTCAGA | GTAATAGCTA | ATTACTGAAC | TTTTAATCAG | TCCCAGGAAT TGAGCATAAA | 6222 |
| ATTATAATTT | TATCTAGTCT | AAATTACTAT | TTCATGAAGC | AGGTATTATT ATTAATCCCA | 6282 |
| TTTTATAGAT | TAACTTGCTC | AAAGTCACAT | TGCTGATAAG | TGGTAGAGGT AGAATTCAGA | 6342 |
| CTCAAGTAGT | TTAACTTTAG | AGCCTGTCCT | CTTAACAACT | ATCCTGGTTG AAAAGCAAAT | 6402 |
| ACAGCCTCTT | CAGACTTCTC | AGTGCCTTGA | TGGCCATTTA | TTCTGTCAAA TCATGAGCTA | 6462 |
| CCCTAAAAGT | AAACCAGCTA | GCTCTTTTGA | TGATCTAGAG | GCTTCTTTTT GCTGAGATA | 6522 |
| TTTGAAGGTT | TTAAGCATTG | TTACCTAATT | AAAATGCAGA | AAAATATCCA ACCCTCTTGT | 6582 |
| TATGTTTAAG | GAATAGTGAA | ATATATTGTC | TTCAAACACA | TGGACTTTTT TTTATTGCTT | 6642 |
| GGTTGGTTTT | TAATCCAGAA | AGTGCTATAG | TCAGTAGACC | TTCTTCTAGG AAAGGACCTT | 6702 |
| CCATTTCCCA | GCCACTGGAG | ATTAGAAAAT | AAGCTAAATA | TTTTCTGGAA ATTTCTGTTC | 6762 |
| ATTCATTAAG | GCCCATCCTT | TCCCCCACTC | TATAGAAGTG | TTGTCCACTT GCACAATTTT | 6822 |
| TTCCAGGAAA | GAATCTCTCT | AACTCCTTCA | GCTCACATGC | TTTGGACCAC ACAGGGAAGA | 6882 |
| CTTTGATTGT | GTAATGCCCT | CAGAAGCTCT | CCTTCTTGCC | ACTACCACAC TGATTTGAGG | 6942 |
| AAGAAAATCC | CTTTAGCACC | TAACCCTTCA | GGTGCTATGA | GTGGCTAATG GAACTGTACC | 7002 |
| TCCTTCAAGT | TTTGTGCAAT | AATTAAGGGT | CACTCACTGT | CAGATACTTT CTGTGATCTA | 7062 |
| TGATAATGTG | TGTGCAACAC | ATAACATTTC | AATAAAGTA | GAAAATATGA AATTAGAGTC | 7122 |
| ATCTACACAT | CTGGATTTGA | TCTTAGAATG | AAACAAGCAA | AAAAGCATCC AAGTGAGTGC | 7182 |
| AATTATTAGT | TTTCAGAGAT | GCTTCAAAGG | CTTCTAGGCC | CATCCCGGGA AGTGTTAATG | 7242 |
| AGCTGTGGAC | TGGTTCACAT | ATCTATTGCC | TCTTGCCAGA | TTTGCAAAAA ACTTCACTCA | 7302 |
| ATGAGCAAAT | TCAGCCTTA | AGAAACAAAG | TCAAAAATTC | CAAGGAAGCA TCCTACGAAA | 7362 |
| GAGGGAACTT | CTGAGATCCC | TGAGGAGGGT | CAGCATGTGA | TGGTTGTATT TCCTTCTTCT | 7422 |

| CAG | T | ACT | GCA | GAC | TAT | GCC | ATG | TTC | AAG | GTG | GGA | CCT | GAA | GCT GAC | 7468 |
|---|---|---|---|---|---|---|---|---|---|---|---|---|---|---|---|
| | | Thr | Ala | Asp | Tyr | Ala | Met | Phe | Lys | Val | Gly | Pro | Glu | Ala Asp | |
| | | 285 | | | | | 290 | | | | | 295 | | | |

| AAG | TAC | CGC | CTA | ACA | TAT | GCC | TAC | TTC | GCT | GGT | GGG | GAT | GCT | GGA GAT | 7516 |
|---|---|---|---|---|---|---|---|---|---|---|---|---|---|---|---|
| Lys | Tyr | Arg | Leu | Thr | Tyr | Ala | Tyr | Phe | Ala | Gly | Gly | Asp | Ala | Gly Asp | |
| | 300 | | | | | 305 | | | | | 310 | | | | |

| GCC | TTT | GAT | GGC | TTT | GAT | TTT | GGC | GAT | GAT | CCT | AGT | GAC | AAG | TTT TTC | 7564 |
|---|---|---|---|---|---|---|---|---|---|---|---|---|---|---|---|
| Ala | Phe | Asp | Gly | Phe | Asp | Phe | Gly | Asp | Asp | Pro | Ser | Asp | Lys | Phe Phe | |
| 315 | | | | 320 | | | | | 325 | | | | | 330 | |

| | | | | | | | | | | | | | | | | |
|---|---|---|---|---|---|---|---|---|---|---|---|---|---|---|---|---|
|ACA|TCC|CAT|AAT|GGC|ATG|CAG|TTC|AGT|ACC|TGG|GAC|AAT|GAC|AAT|GAT|7612|
|Thr|Ser|His|Asn|Gly|Met|Gln|Phe|Ser|Thr|Trp|Asp|Asn|Asp|Asn|Asp| |
| | | |335| | | | |340| | | | |345| | | |

| | | | | | | | | | | | | | | | | |
|---|---|---|---|---|---|---|---|---|---|---|---|---|---|---|---|---|
|AAG|TTT|GAA|GGC|AAC|TGT|GCT|GAA|CAG|GAT|GGA|TCT|GGT|TGG|TGG|ATG|7660|
|Lys|Phe|Glu|Gly|Asn|Cys|Ala|Glu|Gln|Asp|Gly|Ser|Gly|Trp|Trp|Met| |
| | | |350| | | | |355| | | | |360| | | |

| | | | | | | | | | | | | | |
|---|---|---|---|---|---|---|---|---|---|---|---|---|---|
|AAC|AAG|TGT|CAC|GCT|GGC|CAT|CTC|AAT|GGA|GTT|TAT|TAC|CAA|G|7703|
|Asn|Lys|Cys|His|Ala|Gly|His|Leu|Asn|Gly|Val|Tyr|Tyr|Gln| | |
| | |365| | | | |370| | | | |375| | | |

```
GTATGTTTTC  CTTTCTTAGA  TTCCAAGTTA  ATGTATAGTG  TATACTATTT  TCATAAAAAA   7763
TAATAAATAG  ATATGAAGAA  ATGAAGAATA  ATTTATAAAG  ATAGTAGGGA  TTTTATCATG   7823
TTCTTTATTT  CAACTAAGTT  CTTTGAAACT  GGAAGTGGAT  AATACCAAGT  TCATGCCTAA   7883
AATTAGCCCT  TCTAAAGAAA  TCCACCTGCT  GCAAATATC   CAGTAGTTTG  GCATTATATG   7943
TGAAACTATC  ACCATCATAG  CTGGCACTGT  GGGTTGTGGG  ATCTCCTTTA  GACATACAAC   8003
ATAAATGATC  TGGATGGATT  AACATTACTA  CATGGATGCT  TGTTGACACA  TTAACCTGGC   8063
TTCCCATGAG  CTTTGTGTCA  GATACACGCA  GTGAACAGGT  GTTTGGAGGA  ACAGAATAAA   8123
GAGAAGGCAA  GCACTGGTAA  GGGCAGGGGT  TTGTGAAAGC  TTGAGAGAAG  AGACCAGTCT   8183
GAGGACAGTA  GACACTTATT  TTAGGATGGG  GGTTGGATGA  GGAGGCTATA  GTTTGCTATA   8243
AGCTTGGAAT  GGTTTGGAAC  ACTGGTTTCA  CTCACCTACC  CAGCAGTTAT  GTGTGGGGAA   8303
GCCTTACCGA  TGCTAAAGGA  TCCATGTTAC  AATAATGGCA  TTATTTGGAA  ATCCCAGTGG   8363
TATTCCATGA  ATAAAACCAC  TATGAAGATA  ATCCCACTCA  ACAGACTCTC  CGTTGGAGAA   8423
GGACAGCAAC  ACCACCCTGG  GAAAGCCAAA  CAGTCAGACC  AGACCTGTTT  AGCATCAGTA   8483
GGACTTCCCT  ACCATATCTG  CTGGGTAGAT  GAGTGAAACC  AGTGTTCCAA  ACCACTCCGG   8543
GCTTGTAGCA  AACCATAGTC  TCCTCATCTA  CCAAGATGAG  CAACCTTACC  TCCTGATGTC   8603
CTAGCCAATC  ACCAACTAGG  AAACTTTGCA  CAGTTTATTT  AAAGTAACAG  TTTGATTTTC   8663
ACAATATTTT  TAAATTGGAG  AAACATAACT  TATCTTTGCA  CTCACAAACC  ACATAATGAG   8723
AAGAAACTCT  AAGGGAAAAT  GCTTGATCTG  TGTGACCCGG  GGCGCCATGC  CAGAGCTGTA   8783
GTTCATGCCA  GTGTTGTGCT  CTGACAAGCC  TTTTACAGAA  TTACATGAGA  TCTGCTTCCC   8843
TAGGACAAGG  AGAAGGCAAA  TCAACAGAGG  CTGCACTTTA  AAATGGAGAC  ATAAAATAAC   8903
ATGCCAGAAC  CATTTCCTAA  AGCTCCTCAA  TCAACCAACA  AAATTGTGCT  TTCAAATAAC   8963
CTGAGTTGAC  CTCATCAGGA  ATTTTGTGGC  TCCTTCTCTT  CTAACCTGCC  TGAAGAAAGA   9023
TGGTCCACAG  CAGCTGAGTC  CGGGATGGAT  AAGCTTAGGG  ACAGAGGCCA  ATTAGGGAAC   9083
TTTGGGTTTC  TAGCCCTACT  AGTAGTGAAT  AAATTTAAAG  TGTGGATGTG  ACTATGAGTC   9143
ACAGCACAGA  TGTTGTTTAA  TAATATGTTT  ATTTTATAAA  TTGATATTTT  AGGAATCTTT   9203
GGAGATATTT  TCAGTTAGCA  GATAATACTA  TAAATTTTAT  GTAACTGGCA  ATGCACTTCG   9263
TAATAGACAG  CTCTTCATAG  ACTTGCAGAG  GTAAAAAGAT  TCCAGAATAA  TGATATGTAC   9323
ATCTACGACT  TGTTTTAG    GT  GGC  ACT  TAC  TCA  AAA  GCA  TCT  ACT  CCT  AAT   9373
```

| | | | | | | | | |
|---|---|---|---|---|---|---|---|---|
| | |Gly|Gly|Thr|Tyr|Ser|Lys|Ala|Ser|Thr|Pro|Asn|
| | | | |380| | | | |385| | |

| | | | | | | | | | | | | | | | |
|---|---|---|---|---|---|---|---|---|---|---|---|---|---|---|---|
|GGT|TAT|GAT|AAT|GGC|ATT|ATT|TGG|GCC|ACT|TGG|AAA|ACC|CGG|TGG|TAT|9421|
|Gly|Tyr|Asp|Asn|Gly|Ile|Ile|Trp|Ala|Thr|Trp|Lys|Thr|Arg|Trp|Tyr| |
| | | |390| | | | |395| | | | |400| | | |

| | | | | | | | | | | | | | | | |
|---|---|---|---|---|---|---|---|---|---|---|---|---|---|---|---|
|TCC|ATG|AAG|AAA|ACC|ACT|ATG|AAG|ATA|ATC|CCA|TTC|AAC|AGA|CTC|ACA|9469|
|Ser|Met|Lys|Lys|Thr|Thr|Met|Lys|Ile|Ile|Pro|Phe|Asn|Arg|Leu|Thr| |
| | | |405| | | | |410| | | | |415| | | |

| | | | | | | | | | | | | | | | |
|---|---|---|---|---|---|---|---|---|---|---|---|---|---|---|---|
|ATT|GGA|GAA|GGA|CAG|CAA|CAC|CAC|CTG|GGG|GGA|GCC|AAA|CAG|GTC|AGA|9517|

```
Ile Gly Glu Gly Gln Gln His His Leu Gly Gly Ala Lys Gln Val Arg
420                 425                 430                 435

CCA GAG CAC CCT GCG GAA ACA GAA TAT GAC TCA CTT TAC CCT GAG GAT         9565
Pro Glu His Pro Ala Glu Thr Glu Tyr Asp Ser Leu Tyr Pro Glu Asp
                440                 445                 450

GAT TTG TAGAAAATTA ACTGCTAACT TCTATTGACC ACAAAGTTT CAGAAATTCT          9621
Asp Leu
CTGAAAGTTT CTTCCTTTTT TCTCTTACTA TATTTATTGA TTTCAAGTCT TCTATTAAGG      9681
ACATTTAGCC TTCAATGGAA ATTAAAACTC ATTTAGGACT GTATTCCAA ATTACTGATA       9741
TCAGAGTTAT TTAAAAATTG TTATTTGAG GAGATAACAT TCAACTTTG TTCCTAAATA        9801
TATAATAATA AAATGATTGA CTTTATTTGC ATTTTATGA CCACTTGTCA TTTATTTTGT       9861
CTTCGTAAAT TATTTTCATT ATATCAAATA TTTAGTATG TACTTAATAA AATAGGAGAA      9921
CATTTTAGAG TTTCAAATTC CCAGGTATTT TCCTTGTTTA TTACCCCTAA ATCATTCCTA     9981
TTTAATTCTT CTTTTTAAAT GGAGAAAATT ATGTCTTTTT AATATGGTTT TTGTTTTGTT     10041
ATATATTCAC AGGCTGGAGA CGTTTAAAAG ACCGTTTCAA AAGAGATTTA CTTTTTAAA      10101
GGACTTTATC TGAACAGAGA GATATAATAT TTTTCCTATT GGACAATGGA CTTGCAAAGC     10161
TTCACTTCAT TTTAAGAGCA AAAGACCCCA TGTTGAAAAC TCCATAACAG TTTTATGCTG     10221
ATGATAATTT ATCTACATGC ATTTCAATAA ACCTTTTGTT TCCTAAGACT AGATACATGG     10281
TACCTTTATT GACCATTAAA AAACCACCAC TTTTTGCCAA TTTACCAATT ACAATTGGGC     10341
AACCATCAGT AGTAATTGAG TCCTCATTTT ATGCTAAATG TTATGCCTAA CTCTTTGGGA     10401
GTTACAAAGG AAATAGCAAT TATGGCTTTT GCCCTCTAGG AGATACAGGA CAAATACAGG     10461
AAAATACAGC AACCCAAACT GACAATACTC TATACAAGAA CATAATCACT AAGCAGGAGT     10521
CACAGCCACA CAACCAAGAT GCATAGTATC CAAAGTGCAG CTG                       10564
```

( 2 ) INFORMATION FOR SEQ ID NO:6:

( i ) SEQUENCE CHARACTERISTICS:
        ( A ) LENGTH: 453 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Trp Ser Leu His Pro Arg Asn Leu Ile Leu Tyr Phe Tyr Ala
 1               5                  10                  15

Leu Leu Phe Leu Ser Ser Thr Cys Val Ala Tyr Val Ala Thr Arg Asp
                20                  25                  30

Asn Cys Cys Ile Leu Asp Glu Arg Phe Gly Ser Tyr Cys Pro Thr Thr
            35                  40                  45

Cys Gly Ile Ala Asp Phe Leu Ser Thr Tyr Gln Thr Lys Val Asp Lys
        50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Ile Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
        130                 135                 140
```

```
Gln  Lys  Ile  Val  Asn  Leu  Lys  Glu  Lys  Val  Ala  Gln  Leu  Glu  Ala  Gln
145                 150                      155                      160

Cys  Gln  Glu  Pro  Cys  Lys  Asp  Thr  Val  Gln  Ile  His  Asp  Ile  Thr  Gly
                    165                      170                      175

Lys  Asp  Cys  Gln  Asp  Ile  Ala  Asn  Lys  Gly  Ala  Lys  Gln  Ser  Gly  Leu
               180                      185                      190

Tyr  Phe  Ile  Lys  Pro  Leu  Lys  Ala  Asn  Gln  Gln  Phe  Leu  Val  Tyr  Cys
          195                      200                      205

Glu  Ile  Asp  Gly  Ser  Gly  Asn  Gly  Trp  Thr  Val  Phe  Gln  Lys  Arg  Leu
          210                      215                      220

Asp  Gly  Ser  Val  Asp  Phe  Lys  Lys  Asn  Trp  Ile  Gln  Tyr  Lys  Glu  Gly
225                      230                      235                      240

Phe  Gly  His  Leu  Ser  Pro  Thr  Gly  Thr  Thr  Glu  Phe  Trp  Leu  Gly  Asn
                    245                      250                      255

Glu  Lys  Ile  His  Leu  Ile  Ser  Thr  Gln  Ser  Ala  Ile  Pro  Tyr  Ala  Leu
               260                      265                      270

Arg  Val  Glu  Leu  Glu  Asp  Trp  Asn  Gly  Arg  Thr  Ser  Thr  Ala  Asp  Tyr
          275                      280                      285

Ala  Met  Phe  Lys  Val  Gly  Pro  Glu  Ala  Asp  Lys  Tyr  Arg  Leu  Thr  Tyr
290                      295                      300

Ala  Tyr  Phe  Ala  Gly  Gly  Asp  Ala  Gly  Asp  Ala  Phe  Asp  Gly  Phe  Asp
305                      310                      315                      320

Phe  Gly  Asp  Asp  Pro  Ser  Asp  Lys  Phe  Phe  Thr  Ser  His  Asn  Gly  Met
                    325                      330                      335

Gln  Phe  Ser  Thr  Trp  Asp  Asn  Asp  Asn  Asp  Lys  Phe  Glu  Gly  Asn  Cys
               340                      345                      350

Ala  Glu  Gln  Asp  Gly  Ser  Gly  Trp  Trp  Met  Asn  Lys  Cys  His  Ala  Gly
          355                      360                      365

His  Leu  Asn  Gly  Val  Tyr  Tyr  Gln  Gly  Gly  Thr  Tyr  Ser  Lys  Ala  Ser
370                      375                      380

Thr  Pro  Asn  Gly  Tyr  Asp  Asn  Gly  Ile  Ile  Trp  Ala  Thr  Trp  Lys  Thr
385                      390                      395                      400

Arg  Trp  Tyr  Ser  Met  Lys  Lys  Thr  Thr  Met  Lys  Ile  Ile  Pro  Phe  Asn
                    405                      410                      415

Arg  Leu  Thr  Ile  Gly  Glu  Gly  Gln  Gln  His  His  Leu  Gly  Gly  Ala  Lys
               420                      425                      430

Gln  Val  Arg  Pro  Glu  His  Pro  Ala  Glu  Thr  Glu  Tyr  Asp  Ser  Leu  Tyr
          435                      440                      445

Pro  Glu  Asp  Asp  Leu
450
```

( 2 ) INFORMATION FOR SEQ ID NO:7:

( i ) SEQUENCE CHARACTERISTICS:
( A ) LENGTH: 10807 base pairs
( B ) TYPE: nucleic acid
( C ) STRANDEDNESS: double
( D ) TOPOLOGY: linear ( v i i ) IMMEDIATE SOURCE:
( B ) CLONE: ovine beta-lactoglobulin ( x i ) SEQUENCE DESCRIPTION: SEQ ID NO:7:

```
ACGCGTGTCG ACCTGCAGGT CAACGGATCT CTGTGTCTGT TTCATGTTA GTACCACACT       60

GTTTGGTGG CTGTAGCTTT CAGCTACAGT CTGAAGTCAT AAAGCCTGGT ACCTCCAGCT      120

CTGTTCTCTC TCAAGATTGT GTTCTGCTGT TTGGGTCTTT AGTGTCTCCA CACAATTTTT    180
```

| | | | | | |
|---|---|---|---|---|---|
| AGAATTGTTT | GTTCTAGTTC | TGTGAAAAAT | GATGCTGGTA | TTTTGATAAG | GATTGCATTG | 240 |
| AATCTGTAAA | GCTACAGATA | TAGTCATTGG | GTAGTACAGT | CACTTTAACA | ATATTAACTC | 300 |
| TTCACATCTG | TGAGCATGAT | ATATTTTCCC | CCTCTATATC | ATCTTCAATT | CCTCCTATCA | 360 |
| GTTTCTTTCA | TTGCAGTTTT | CTGAGTACAG | GTCTTACACC | TCCTTGGTTA | GAGTCATTCC | 420 |
| TCAGTATTTT | ATTCCTTTGA | TACAATTGTG | AATGAGGTAA | TTTTCTTAGT | TTCTCTTTCT | 480 |
| GATAGCTCAT | TGTTAGTGTA | TATATAGAAA | AGCAACAGAT | TTCTATGTAT | TAATTTTGTA | 540 |
| TCCTGCAACA | GATTTCTATG | TATTAATTTT | GTATCCTGCT | ACTTACGGA | ATTCACTTAT | 600 |
| TAGCTTTTTG | GTGACATCTT | GAGGATTTTC | TGAAGAAAAT | GGCATGGTAT | GGTAGGACAA | 660 |
| GGTGTCATGT | CATCTGCAAA | CAGTGGCAGT | TTTCCTTCTT | CCCTTCCAAC | CTGGATTTCT | 720 |
| TTGATTTCTT | TCTGTCTGAG | TACGACTAGG | ATTCCCAATA | CTATACCGAA | TAAAAGTGGC | 780 |
| AAGAGTGGAC | ATCCTTGTCT | TATTTTCTG | ACCTTAGAGG | AAATGCTTTC | AGTTTTCAC | 840 |
| CATTAATTAT | AATGTTACT | GTGGGCTTGT | CATATGTGGC | CTTCATTATA | TGGAGGTCTA | 900 |
| TTCCCTCTAT | ACCCACCTTG | TTGAGAGTTT | TTATCATAAA | AGTATGTTGA | ATTTGTCAA | 960 |
| AAGTTTTCC | TGCATCTATT | GAGATGATTT | TTACTCTTCA | ATTCATTAAT | GATTTTATT | 1020 |
| CTTCATTTG | TTAATGATTT | CCATTCTTCA | ATTGTTAAC | GTGGTATATC | ACATTGATTG | 1080 |
| ATTTGTGGAT | ACCTTTGTAT | CCCTGGGATA | AACCTCACTT | GATCATGAGC | TTTCAATGTA | 1140 |
| TTTTTGAATT | CACTTTGCTA | ATATTCTGTT | GGGTATTTTT | GCATCTCTAT | TCATCAATGA | 1200 |
| TATTGGCCTA | AGAAAGGTTT | TGTCTGGTTT | TAGTATCAGG | GTGATGCTGG | CCTCATAGAG | 1260 |
| AGAGTTTAGA | AGCATTTCCT | CCTCTTTGAT | TTTTCGGAAT | AGTTTGAGTA | GGATAGGTAT | 1320 |
| TAACTCTTCT | TTAAATGTTT | GGGGACTTCC | CTGGTGAGCC | GGTGGTTGAG | AATCCGCCTC | 1380 |
| AGGGATGTGG | GTTTGATCCC | TGGTCAGGGA | ACCATTAATA | AGATCCCACA | TGCTGCAGGC | 1440 |
| AACAAGCCCC | CAAGCTGCAA | CCACTGAGCT | GCAACCGCTG | CAGTGCCCAC | AGGCCACGAC | 1500 |
| CAGAGAAAGC | CCACATACAG | CAGGGAAGAC | CCAGCACAAC | CGGAAAAGG | AGTTTGGTGG | 1560 |
| AATACAGCTG | TGAAGCCGTC | TGGTCCTGGA | CTCCTGCTTG | AGGGAATTTT | TTAAAAATTA | 1620 |
| TTGATTCAAT | TCATTACTG | GTAACTGGTC | TGTTCATATT | TTCTATTTCT | TCCGGGTTCA | 1680 |
| GTCTTGGGAG | ATTGTACATG | CCTAGGAATG | TGTCCGTTTC | TTCTAGGTTG | TCCATTTTAT | 1740 |
| TGGACATGCA | TGGGAGCACA | CAGCACCGAC | CAGCGAGACT | CATGCTGGCT | TCCTGGGGCC | 1800 |
| AGGCTGGGGC | CCCAAGCAGC | ATGGCATCCT | AGAGTGTGTG | AAAGCCCACT | GACCCTGCCC | 1860 |
| AGCCCCACAA | TTTCATTCTG | AGAAGTGATT | CCTTGCTTCT | GCACTTACAG | GCCCAGGATC | 1920 |
| TGACCTGCTT | CTGAGGAGCA | GGGGTTTTGG | CAGGACGGGG | AGATGCTGAG | AGCCGACGGG | 1980 |
| GGTCCAGGTC | CCCTCCCAGG | CCCCCCTGTC | TGGGGCAGCC | CTTGGGAAAG | ATTGCCCCAG | 2040 |
| TCTCCCTCCT | ACAGTGGTCA | GTCCAGCTG | CCCCAGGCCA | GAGCTGCTTT | ATTTCCGTCT | 2100 |
| CTCTCTCTGG | ATGGTATTCT | CTGGAAGCTG | AAGGTTCCTG | AAGTTATGAA | TAGCTTTGCC | 2160 |
| CTGAAGGGCA | TGGTTTGTGG | TCACGGTTCA | CAGGAACTTG | GGAGACCCTG | CAGCTCAGAC | 2220 |
| GTCCGAGAT | TGGTGGCACC | CAGATTTCCT | AAGCTCGCTG | GGAACAGGG | CGCTTGTTTC | 2280 |
| TCCCTGGCTG | ACCTCCCTCC | TCCCTGCATC | ACCCAGTTCT | GAAAGCAGAG | CGGTGCTGGG | 2340 |
| GTCACAGCCT | CTCGCATCTA | ACGCCGGTGT | CCAAACCACC | CGTGCTGGTG | TTCGGGGGC | 2400 |
| TACCTATGGG | GAAGGGCTTC | TCACTGCAGT | GGTGCCCCCC | GTCCCCTCTG | AGATCAGAAG | 2460 |
| TCCCAGTCCG | GACGTCAAAC | AGGCCGAGCT | CCCTCCAGAG | GCTCCAGGGA | GGGATCCTTG | 2520 |
| CCCCCCCGCT | GCTGCCTCCA | GCTCCTGGTG | CCGCACCCTT | GAGCCTGATC | TTGTAGACGC | 2580 |

| | | | | | |
|---|---|---|---|---|---|
| CTCAGTCTAG | TCTCTGCCTC | CGTGTTCACA | CGCCTTCTCC | CCATGTCCCC | TCCGTGTCCC | 2640 |
| CGTTTTCTCT | CACAAGGACA | CCGGACATTA | GATTAGCCCC | TGTTCCAGCC | TCACCTGAAC | 2700 |
| AGCTCACATC | TGTAAAGACC | TAGATTCCAA | ACAAGATTCC | AACCTGAAGT | TCCCGGTGGA | 2760 |
| TGTGAGTTCT | GGGGCGACAT | CCTTCAACCC | CATCACAGCT | TGCAGTTCAT | CGCAAACAT | 2820 |
| GGAACCTGGG | GTTTATCGTA | AAACCCAGGT | TCTTCATGAA | ACACTGAGCT | TCGAGGCTTG | 2880 |
| TTGCAAGAAT | TAAAGGTGCT | AATACAGATC | AGGGCAAGGA | CTGAAGCTGG | CTAAGCCTCC | 2940 |
| TCTTTCCATC | ACAGGAAAGG | GGGGCCTGGG | GGCGGCTGGA | GGTCTGCTCC | CGTGAGTGAG | 3000 |
| CTCTTTCCTG | CTACAGTCAC | CAACAGTCTC | TCTGGGAAGG | AAACCAGAGG | CCAGAGAGCA | 3060 |
| AGCCGGAGCT | AGTTTAGGAG | ACCCCTGAAC | CTCCACCCAA | GATGCTGACC | AGCCAGCGGG | 3120 |
| CCCCCTGGAA | AGACCCTACA | GTTCAGGGGG | GAAGAGGGGC | TGACCCGCCA | GGTCCCTGCT | 3180 |
| ATCAGGAGAC | ATCCCCGCTA | TCAGGAGATT | CCCCCACCTT | GCTCCCGTTC | CCCTATCCCA | 3240 |
| ATACGCCCAC | CCCACCCCTG | TGATGAGCAG | TTTAGTCACT | TAGAATGTCA | ACTGAAGGCT | 3300 |
| TTTGCATCCC | CTTTGCCAGA | GGCACAAGGC | ACCCACAGCC | TGCTGGGTAC | CGACGCCCAT | 3360 |
| GTGGATTCAG | CCAGGAGGCC | TGTCCTGCAC | CCTCCCTGCT | CGGGCCCCCT | CTGTGCTCAG | 3420 |
| CAACACACCC | AGCACCAGCA | TTCCCGCTGC | TCCTGAGGTC | TGCAGGCAGC | TCGCTGTAGC | 3480 |
| CTGAGCGGTG | TGGAGGGAAG | TGTCCTGGGA | GATTTAAAAT | GTGAGAGGCG | GGAGGTGGGA | 3540 |
| GGTTGGGCCC | TGTGGGCCTG | CCCATCCCAC | GTGCCTGCAT | TAGCCCCAGT | GCTGCTCAGC | 3600 |
| CGTGCCCCCG | CCGCAGGGGT | CAGGTCACTT | TCCCGTCCTG | GGGTTATTAT | GACTCTTGTC | 3660 |
| ATTGCCATTG | CCATTTTTGC | TACCCTAACT | GGGCAGCAGG | TGCTTGCAGA | GCCCTCGATA | 3720 |
| CCGACCAGGT | CCTCCCTCGG | AGCTCGACCT | GAACCCCATG | TCACCCTTGC | CCCAGCCTGC | 3780 |
| AGAGGGTGGG | TGACTGCAGA | GATCCCTTCA | CCCAAGGCCA | CGGTCACATG | GTTTGGAGGA | 3840 |
| GCTGGTGCCC | AAGGCAGAGG | CCACCCTCCA | GGACACACCT | GTCCCCAGTG | CTGGCTCTGA | 3900 |
| CCTGTCCTTG | TCTAAGAGGC | TGACCCCGGA | AGTGTTCCTG | GCACTGGCAG | CCAGCCTGGA | 3960 |
| CCCAGAGTCC | AGACACCCAC | CTGTGCCCCC | GCTTCTGGGG | TCTACCAGGA | ACCGTCTAGG | 4020 |
| CCCAGAGGGG | ACTTCCTGCT | TGGCCTTGGA | TGGAAGAAGG | CCTCCTATTG | TCCTCGTAGA | 4080 |
| GGAAGCCACC | CCGGGGCCTG | AGGATGAGCC | AAGTGGGATT | CCGGGAACCG | CGTGGCTGGG | 4140 |
| GGCCCAGCCC | GGGCTGGCTG | GCCTGCATGC | CTCCTGTATA | AGGCCCCAAG | CCTGCTGTCT | 4200 |
| CAGCCCTCCA | CTCCCTGCAG | AGCTCAGAAG | CACGACCCCA | GGGATATCCC | TGCAGCCATG | 4260 |
| AAGTGCCTCC | TGCTTGCCCT | GGGCCTGGCC | CTCGCCTGTG | GCGTCCAGGC | CATCATCGTC | 4320 |
| ACCCAGACCA | TGAAAGGCCT | GGACATCCAG | AAGGTTCGAG | GGTTGGCCGG | GTGGGTGAGT | 4380 |
| TGCAGGGCGG | GCAGGGGAGC | TGGGCCTCAG | AGAGCCAAGA | GAGGCTGTGA | CGTTGGGTTC | 4440 |
| CCATCAGTCA | GCTAGGGCCA | CCTGACAAAT | CCCCGCTGGG | GCAGCTTCAA | CCAGGCGTTC | 4500 |
| ACTGTCTTGC | ATTCTGGAGG | CTGGAAGCCC | AAGATCCAGG | TGTTGGCAGG | GCTGGCTTCT | 4560 |
| CCTGCGGCCG | CTCTCTGGGG | AGCAGACGGC | CGTCTTCTCC | AGTCCTCTGC | GCGCCCTGAT | 4620 |
| TTCCTCTTCC | TGTGAGGCCA | CCAGGCCTGC | TGGAAACACG | CCTGCCTGCG | CAGCTTCACA | 4680 |
| CGACCTTTGT | CATCTCTTTA | AAGGCCATGT | CTCCAGAGTC | ATGTGTTGAA | GTTCTGGGGG | 4740 |
| TTAGTGGGAC | ACAGTTCAGC | CCCTAAAAGA | GTCTCTCTGC | CCCTCAAATT | TTCCCCACCT | 4800 |
| CCAGCCATGT | CTCCCCAAGA | TCCAAATGTT | GCTACATGTG | GGGGGGCTCA | TCTGGGTCCC | 4860 |
| TCTTTGGGTT | CAGTGTGAGT | CTGGGAGAG | CATTCCCCAG | GGTGCAGAGT | TGGGGGGAGT | 4920 |
| ATCTCAGGGC | TGCCCAGGCC | GGGGTGGGAC | AGAGAGCCCA | CTGTGGGGCT | GGGGGCCCCT | 4980 |

| | | | | | |
|---|---|---|---|---|---|
| TCCCACCCCC | AGAGTGCAAC | TCAAGGTCCC | TCTCCAGGTG | GCGGGGACTT | GGCACTCCTT | 5040 |
| GGCTATGGCG | GCCAGCGACA | TCTCCCTGCT | GGATGCCCAG | AGTGCCCCCC | TGAGAGTGTA | 5100 |
| CGTGGAGGAG | CTGAAGCCCA | CCCCCGAGGG | CAACCTGGAG | ATCCTGCTGC | AGAAATGGTG | 5160 |
| GCGTCTCTC | CCCAACATGG | AACCCCCACT | CCCCAGGGCT | GTGGACCCCC | CGGGGGGTGG | 5220 |
| GGTGCAGGAG | GGACCAGGGC | CCAGGGCTG | GGGAAGAGGG | CTCAGAGTTT | ACTGGTACCC | 5280 |
| GGCGCTCCAC | CCAAGGCTGC | CCACCCAGGG | CTTTTTTTT | TTTTAAACTT | TTATTAATTT | 5340 |
| GATGCTTCAG | AACATCATCA | AACAAATGAA | CATAAACAT | TCATTTTGT | TTACTTGGAA | 5400 |
| GGGAGATAA | AATCCTCTGA | AGTGGAAATG | CATAGCAAAG | ATACATACAA | TGAGGCAGGT | 5460 |
| ATTCTGAATT | CCCTGTTAGT | CTGAGGATTA | CAAGTGTATT | TGAGCAACAG | AGAGACATTT | 5520 |
| TCATCATTTC | TAGTCTGAAC | ACCTCAGTAT | CTAAAATGAA | CAAGAAGTCC | TGGAAACGAA | 5580 |
| GCAGTGTGGG | GATAGGCCCG | TGTGAAGGCT | GCTGGGAGGC | AGCAGACCTG | GGTCTTCGGG | 5640 |
| CTCAAGCAGT | TCCCGCTACC | AGCCCTGTCC | ACCTCAGACG | GGGTCAGGG | TGCAGGAGAG | 5700 |
| AGCTGGATGG | GTGTGGGGGC | AGAGATGGGG | ACCTGAACCC | CAGGGCTGCC | TTTTGGGGGT | 5760 |
| GCCTGTGGTC | AAGGCTCTCC | CTGACCTTTT | CTCTCTGGCT | TCATCTGACT | TCTCCTGGCC | 5820 |
| CATCCACCCG | GTCCCTGTG | GCCTGAGGTG | ACAGTGAGTG | CGCCGAGGCT | AGTTGGCCAG | 5880 |
| CTGGCTCCTA | TGCCCATGCC | ACCCCCCTCC | AGCCCTCCTG | GGCCAGCTTC | TGCCCCTGGC | 5940 |
| CCTCAGTTCA | TCCTGATGAA | AATGGTCCAT | GCCAATGGCT | CAGAAAGCAG | CTGTCTTTCA | 6000 |
| GGGAGAACGG | CGAGTGTGCT | CAGAAGAAGA | TTATTGCAGA | AAAAACCAAG | ATCCCTGCGG | 6060 |
| TGTTCAAGAT | CGATGGTGAG | TCCGGGTCCC | TGGGGACAC | CCACCACCCC | CGCCCCGGG | 6120 |
| GACTGTGGAC | AGGTTCAGGG | GGCTGGCGTC | GGGCCCTGGG | ATGCTAAGGG | ACTGGTGGTG | 6180 |
| ATGAAGACAC | TGCCTTGACA | CCTGCTTCAC | TTGCCTCCCC | TGCCACCTGC | CCGGGGCCTT | 6240 |
| GGGGCGGTGG | CCATGGGCAG | GTCCCGGCTG | GCGGGCTAAC | CCACCAGGGT | GACACCCGAG | 6300 |
| CTCTCTTTGC | TGGGGGGCGG | GCGGTGCTCT | GGGCCCTCAG | GCTGAGCTCA | GGAGGTACCT | 6360 |
| GTGCCCTCCC | AGGGGTAACC | GAGAGCCGTT | GCCCACTCCA | GGGCCCAGG | TGCCCCACGA | 6420 |
| CCCCAGCCCG | CTCCACAGCT | CCTTCATCTC | CTGGAGACAA | ACTCTGTCCG | CCCTCGCTCA | 6480 |
| TTCACTTGTT | CGTCCTAAAT | CCGAGATGAT | AAAGCTTCGA | GGGGGGTTG | GGGTTCCATC | 6540 |
| AGGGCTGCCC | TTCCGCCGGG | CAGCCTGGGC | CACATCTGCC | CTTGGCCCCC | TCAGGACTCA | 6600 |
| CTCTGACTGG | AGGCCCTGCA | CTGACTGACG | CCAGGGTGCC | CAGCCCAGGG | TCTCTGGCGC | 6660 |
| CATCCAGCTG | CACTGGGTTT | GGGTGCTGGT | CCTGCCCCCA | AGCTGCCCGG | ACACCACAGG | 6720 |
| CAGCCGGGGC | TGCCCACTGG | CCTCGGTCAG | GGTGAGCCCC | AGCTGCCCCC | GCTCAGGGCT | 6780 |
| TGCCCCGACA | ATGACCCCAT | CCTCAGGACG | CACCCCCTT | CCCTTGCTGG | GCAGTGTCCA | 6840 |
| GCCCCACCCG | AGATCGGGGG | AAGCCCTATT | TCTTGACAAC | TCCAGTCCCT | GGGGAGGGG | 6900 |
| GCCTCAGACT | GAGTGGTGAG | TGTTCCCAAG | TCCAGGAGGT | GGTGGAGGGT | CCTGGCGGAT | 6960 |
| CCAGAGTTGA | CAGTGAGGGC | TTCCTGGGCC | CCATGCGCCT | GGCAGTGGCA | GCAGGGAAGA | 7020 |
| GGAAGCACCA | TTTCAGGGGT | GGGGGATGCC | AGAGGCGCTC | CCCACCCCGT | CTTCGCCGGG | 7080 |
| TGGTGACCCC | GGGGAGCCC | CGCTGGTCGT | GGAGGGTGCT | GGGGCTGAC | TAGCAACCCC | 7140 |
| TCCCCCCCG | TTGGAACTCA | CTTTTCTCCC | GTCTTGACCG | CGTCCAGCCT | TGAATGAGAA | 7200 |
| CAAAGTCCTT | GTGCTGGACA | CCGACTACAA | AAAGTACCTG | CTCTTCTGCA | TGGAAAACAG | 7260 |
| TGCTGAGCCC | GAGCAAAGCC | TGGCCTGCCA | GTGCCTGGGT | GGGTGCCAAC | CCTGGCTGCC | 7320 |
| CAGGGAGACC | AGCTGCGTGG | TCCTTGCTGC | AACAGGGGGT | GGGGGTGGG | AGCTTGATCC | 7380 |

| | | | | | |
|---|---|---|---|---|---|
| CCAGGAGGAG | GAGGGGTGGG | GGGTCCCTGA | GTCCCGCCAG | GAGAGAGTGG | TCGCATACCG | 7440 |
| GGAGCCAGTC | TGCTGTGGGC | CTGTGGGTGG | CTGGGACGG | GGGCCAGACA | CACAGGCCGG | 7500 |
| GAGACGGGTG | GGCTGCAGAA | CTGTGACTGG | TGTGACCGTC | GCGATGGGC | CGGTGGTCAC | 7560 |
| TGAATCTAAC | AGCCTTGTT | ACCGGGGAGT | TTCAATTATT | TCCCAAAATA | AGAACTCAGG | 7620 |
| TACAAAGCCA | TCTTTCAACT | ATCACATCCT | GAAAACAAAT | GCAGGTGAC | ATTTTCTGTG | 7680 |
| CCGTAGCAGT | CCCACTGGGC | ATTTTCAGGG | CCCCTGTGCC | AGGGGGGCGC | GGGCATCGGC | 7740 |
| GAGTGGAGGC | TCCTGGCTGT | GTCAGCCGGC | CCAGGGGAG | GAAGGGACCC | GGACAGCCAG | 7800 |
| AGGTGGGGGG | CAGGCTTTCC | CCCTGTGACC | TGCAGACCCA | CTGCACTGCC | CTGGGAGGAA | 7860 |
| GGGAGGGGAA | CTAGGCCAAG | GGGAAGGGC | AGGTGCTCTG | GAGGGCAAGG | GCAGACCTGC | 7920 |
| AGACCACCCT | GGGGAGCAGG | GACTGACCCC | CGTCCCTGCC | CCATAGTCAG | GACCCCGGAG | 7980 |
| GTGGACAACG | AGGCCCTGGA | GAAATTCGAC | AAAGCCCTCA | AGGCCCTGCC | CATGCACATC | 8040 |
| CGGCTTGCCT | TCAACCCGAC | CCAGCTGGAG | GGTGAGCACC | CAGGCCCCGC | CCTTCCCCAG | 8100 |
| GGCAGGAGCC | ACCCGGCCCC | GGGACGACCT | CCTCCCATGG | TGACCCCAG | CTCCCCAGGC | 8160 |
| CTCCCAGGAG | GAAGGGGTGG | GGTGCAGCAC | CCCGTGGGGG | CCCCCTCCCC | ACCCCCTGCC | 8220 |
| AGGCCTCTCT | TCCCGAGGTG | TCCAGTCCCA | TCCTGACCCC | CCCATGACTC | TCCCTCCCCC | 8280 |
| ACAGGGCAGT | GCCACGTCTA | GGTGAGCCCC | TGCCGGTGCC | TCTGGGGTAA | GCTGCCTGCC | 8340 |
| CTGCCCCACG | TCCTGGGCAC | ACACATGGGG | TAGGGGTCT | TGGTGGGGCC | TGGGACCCCA | 8400 |
| CATCAGGCCC | TGGGGTCCCC | CCTGTGAGAA | TGGCTGGAAG | CTGGGGTCCC | TCCTGGCGAC | 8460 |
| TGCAGAGCTG | GCTGGCCGCG | TGCCACTCTT | GTGGGTGACC | TGTGTCCTGG | CCTCACACAC | 8520 |
| TGACCTCCTC | CAGCTCCTTC | CAGCAGAGCT | AAGGCTAAGT | GAGCCAGAAT | GGTACCTAAG | 8580 |
| GGGAGGCTAG | CGGTCCTTCT | CCCGAGGAGG | GGCTGTCCTG | GAACCACCAG | CCATGGAGAG | 8640 |
| GCTGGCAAGG | GTCTGGCAGG | TGCCCCAGGA | ATCACAGGGG | GGCCCCATGT | CCATTTCAGG | 8700 |
| GCCCGGGAGC | CTTGGACTCC | TCTGGGGACA | GACGACGTCA | CCACCGCCCC | CCCCCCATCA | 8760 |
| GGGGGACTAG | AAGGGACCAG | GACTGCAGTC | ACCCTTCCTG | GGACCCAGGC | CCCTCCAGGC | 8820 |
| CCCTCCTGGG | GCTCCTGCTC | TGGGCAGCTT | CTCCTTCACC | AATAAAGGCA | TAAACCTGTG | 8880 |
| CTCTCCCTTC | TGAGTCTTTG | CTGGACGACG | GGCAGGGGT | GGAGAAGTGG | TGGGGAGGGA | 8940 |
| GTCTGGCTCA | GAGGATGACA | GCGGGGCTGG | GATCCAGGGC | GTCTGCATCA | CAGTCTTGTG | 9000 |
| ACAACTGGGG | GCCCACACAC | ATCACTGCGG | CTCTTTGAAA | CTTTCAGGAA | CCAGGGAGGG | 9060 |
| ACTCGGCAGA | GACATCTGCC | AGTTCACTTG | GAGTGTTCAG | TCAACACCCA | AACTCGACAA | 9120 |
| AGGACAGAAA | GTGGAAAATG | GCTGTCTCTT | AGTCTAATAA | ATATTGATAT | GAAACTCAAG | 9180 |
| TTGCTCATGG | ATCAATATGC | CTTTATGATC | CAGCCAGCCA | CTACTGTCGT | ATCAACTCAT | 9240 |
| GTACCCAAAC | GCACTGATCT | GTCTGGCTAA | TGATGAGAGA | TTCCAGTAG | AGAGCTGGCA | 9300 |
| AGAGGTCACA | GTGAGAACTG | TCTGCACACA | CAGCAGAGTC | CACCAGTCAT | CCTAAGGAGA | 9360 |
| TCAGTCCTGG | TGTTCATTGG | AGGACTGATG | TTGAAGCTGA | AACTCCAATG | CTTTGGCCAC | 9420 |
| CTGATGTGAA | GAGCTGACTC | ATTTGAAAAG | ACCCTGATGC | TGGGAAAGAT | TGAGGGCAGG | 9480 |
| AGGAGAAGGG | GACGACAGAG | GATGAGATGG | TTGGATGGCA | TCACCAACAC | AATGGACATG | 9540 |
| GGTTTGGGTG | GACTCCAGGA | GTTGGTGATG | GACAGGGAGG | CCTGGCGTGC | TACGGAAGCG | 9600 |
| GTTTATGGGG | TCACAAAGAC | TGAGTGACTG | AACTGAGCTG | AACTGAATGG | AAATGAGGTA | 9660 |
| TACAGCAAAG | TGGGGATTTT | TTAGATAATA | AGAATATACA | CATAACATAG | TGTATACTCA | 9720 |
| TATTTTTATG | CATACCTGAA | TGCTCAGTCA | CTCAGTCGTA | TCTGACTCTG | TGACCTATGG | 9780 |

-continued

```
ACCGTAGCCT TCCAGGTTTC TTCTGTCCAC AGAATTCTCC AAGGCAAGAA TACTGGAGTG    9840
GGTAGCCATT TCCTCCTCCA GGGGATCCTC CCGACCCAGG GATTGAACCG GCATCTCCTG    9900
TATTGGCAGG TGGATTCTTT ACCACTGTGC CACCAGGGAA GCCCGTGTTA CTCTCTATGT    9960
CCCACTTAAT TACCAAAGCT GCTCCAAGAA AAAGCCCCTG TGCCCTCTGA GCTTCCCGGC   10020
CTGCAGAGGG TGGTGGGGGT AGACTGTGAC CTGGGAACAC CCTCCGCTT CAGGACTCCC    10080
GGGCCACGTG ACCCACAGTC CTGCAGACAG CCGGGTAGCT CTGCTCTTCA AGGCTCATTA  10140
TCTTTAAAAA AAACTGAGGT CTATTTGTG ACTTCGCTGC CGTAACTTCT GAACATCCAG   10200
TGCGATGGAC AGGACCTCCT CCCCAGGCCT CAGGGGCTTC AGGGAGCCAG CCTTCACCTA  10260
TGAGTCACCA GACACTCGGG GGTGGCCCCG CCTTCAGGGT GCTCACAGTC TTCCCATCGT  10320
CCTGATCAAA GAGCAAGACC AATGACTTCT TAGGAGCAAG CAGACACCCA CAGGACACTG  10380
AGGTTCACCA GAGCTGAGCT GTCCTTTGA ACCTAAAGAC ACACAGCTCT CGAAGGTTTT   10440
CTCTTTAATC TGGATTTAAG GCCTACTTGC CCCTCAAGAG GGAAGACAGT CCTGCATGTC  10500
CCCAGGACAG CCACTCGGTG GCATCCGAGG CCACTTAGTA TTATCTGACC GCACCCTGGA  10560
ATTAATCGGT CCAAACTGGA CAAAACCTT GGTGGGAAGT TTCATCCCAG AGGCCTCAAC   10620
CATCCTGCTT TGACCACCCT GCATCTTTT TTCTTTTATG TGTATGCATG TATATATA     10680
TATATATTTT TTTTTTTTC ATTTTTGGC TGTGCTGGCT GTTCGTTGCA GTTCGGTGCG    10740
CAGGCTTCTC TCTAGTTTCT CTCTAGTCTT CTCTTATCAC AGAGCAGTCT CTAGACGATC  10800
GACGCGT                                                             10807
```

( 2 ) INFORMATION FOR SEQ ID NO:8:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
AATTCCGATC GACGCGTCGA CGATATACTC TAGACGATCG ACGCGTA                    47
```

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: BLGAMP3

( x i ) SEQUENCE DESCRIPTION: SEQ ID NO:9:

```
TGGATCCCCT GCCGGTGCCT CTGG                                             24
```

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: BLGAMP4

( x i ) SEQUENCE DESCRIPTION: SEQ ID NO:10:

```
AACGCGTCAT CCTCTGTGAG CCAG                                             24
```

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6839

( x i ) SEQUENCE DESCRIPTION: SEQ ID NO:11:

ACTACGTAGT                                                            10

( 2 ) INFORMATION FOR SEQ ID NO:12:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6632

( x i ) SEQUENCE DESCRIPTION: SEQ ID NO:12:

CGACGCGGAT CCTACGTACC TGCAGCCATG TTTTCCATGA GG                42

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6627

( x i ) SEQUENCE DESCRIPTION: SEQ ID NO:13:

AGGGCTTCGG CAAGCTTCAG G                                   21

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6521

( x i ) SEQUENCE DESCRIPTION: SEQ ID NO:14:

GCCAAAGACT TACTTCCCTC TAGA                                24

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6520

( x i ) SEQUENCE DESCRIPTION: SEQ ID NO:15:

GCATGAACGT CGCGTGGTGG TTGTGCTACC                        30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6519

( x i ) SEQUENCE DESCRIPTION: SEQ ID NO:16:

ACCACGCGAC GTTCATGCTC TAAAACCGTT     30

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6518

( x i ) SEQUENCE DESCRIPTION: SEQ ID NO:17:

GCTGCGGGAT CCTACGTACT AGGGGACAG GGAAGG     36

( 2 ) INFORMATION FOR SEQ ID NO:18:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6629

( x i ) SEQUENCE DESCRIPTION: SEQ ID NO:18:

CGACGCGAAT TCTACGTACC TGCAGCCATG AAAAGGATGG TTTCT     45

( 2 ) INFORMATION FOR SEQ ID NO:19:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6630

( x i ) SEQUENCE DESCRIPTION: SEQ ID NO:19:

CGACGCGAAT TCTACGTACC TGCAGCCATG AAACATCTAT TATTG     45

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6625

( x i ) SEQUENCE DESCRIPTION: SEQ ID NO:20:

GTGAGATTTT CAGATCTTGT C     21

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6626

( x i ) SEQUENCE DESCRIPTION: SEQ ID NO:21:

AAGAATTACT GTGGCCTACC A        21

( 2 ) INFORMATION FOR SEQ ID NO:22:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6624

( x i ) SEQUENCE DESCRIPTION: SEQ ID NO:22:

GCTGCGGAAT TCTACGTACT ATTGCTGTGG GAA        33

( 2 ) INFORMATION FOR SEQ ID NO:23:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6514

( x i ) SEQUENCE DESCRIPTION: SEQ ID NO:23:

CGACGCGGAT CCTACGTACC TGCAGCCATG AGTTGGTCCT TGCAC        45

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6517

( x i ) SEQUENCE DESCRIPTION: SEQ ID NO:24:

GTCTCTGGTA GCAACATACT A        21

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6516

( x i ) SEQUENCE DESCRIPTION: SEQ ID NO:25:

GGGTTTCTAG CCCTACTAGT AG        22

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: zc6515

( x i ) SEQUENCE DESCRIPTION: SEQ ID NO:26:

```
GGGTTTCTAG CCCTACTAGT AG                                          22
```

( 2 ) INFORMATION FOR SEQ ID NO:27:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

```
AAGCTACGCG TCGATCGTCT AGAGTATATC GTCGACGCGT CGATCGG               47
```